(12) United States Patent
Ketchel, III et al.

(10) Patent No.: US 10,535,088 B2
(45) Date of Patent: Jan. 14, 2020

(54) NETWORK-BASED MARKETPLACE SERVICE FOR FACILITATING PURCHASES OF BUNDLED SERVICES AND PRODUCTS

(71) Applicant: MDSave Shared Services Inc., Brentwood, TN (US)

(72) Inventors: Paul J. Ketchel, III, Nashville, TN (US); Ani Osborne, Brentwood, TN (US)

(73) Assignee: MDSave Shared Services Inc., Brentwood, TN (US)

( * ) Notice: Subject to any disclaimer, the term of this patent is extended or adjusted under 35 U.S.C. 154(b) by 107 days.

(21) Appl. No.: 15/908,715

(22) Filed: Feb. 28, 2018

(65) Prior Publication Data
US 2018/0260870 A1 Sep. 13, 2018

Related U.S. Application Data

(63) Continuation of application No. 14/750,081, filed on Jun. 25, 2015, now abandoned, which is a
(Continued)

(51) Int. Cl.
*G06Q 30/00* (2012.01)
*G06F 17/30* (2006.01)
(Continued)

(52) U.S. Cl.
CPC ......... *G06Q 30/0621* (2013.01); *G06F 19/00* (2013.01); *G06F 19/325* (2013.01);
(Continued)

(58) Field of Classification Search
CPC .................................................. G06Q 30/0621
See application file for complete search history.

(56) References Cited

U.S. PATENT DOCUMENTS 7,895,061 B2 2/2011 Schoenberg
8,428,964 B2 4/2013 Picken
(Continued)

OTHER PUBLICATIONS

Medical instruments & supplies; MedAssets addresses payment reform with bundled reimbursement solution. (2010). Obesity, Fitness & Wellness Week, 1035. Retrieved from http://search.proquest.com/docview/732996687?accountid=14753, 2 pages.
(Continued)

*Primary Examiner* — Kathleen Palavecino
(74) *Attorney, Agent, or Firm* — Coastal IP LLC; Kelly Hollowell

(57) ABSTRACT

An apparatus for pricing offers of healthcare services includes an application server providing a pricing tool, and a service pricing information database and a cost adjustment information database that are accessible by the application server. The pricing tool is operable to receive an indication of a healthcare service set that is respectively associated with a service detail information record included in the service pricing information database, determine a base physician fee for a primary service of the indicated healthcare service set based on base pricing metrics for the primary service included in the service detail information record, receive an indication specifying a location for performing the primary service, calculate an adjusted physician fee for the primary service based on cost adjustment metrics for a geographic zone that corresponds to the specified location, and provide a recommended price for the indicated healthcare service set based on the calculated adjusted physician fee.

1 Claim, 13 Drawing Sheets

Related U.S. Application Data continuation-in-part of application No. 14/461,209, filed on Aug. 15, 2014, now Pat. No. 9,123,072.

(60) Provisional application No. 61/866,922, filed on Aug. 16, 2013.

(51) Int. Cl.

| | |
|---|---|
| *G06Q 30/06* | (2012.01) |
| *G06Q 50/22* | (2018.01) |
| *G06F 19/00* | (2018.01) |
| *G06Q 30/02* | (2012.01) |
| *G06Q 20/06* | (2012.01) |
| *G06Q 20/10* | (2012.01) |
| *G06Q 20/38* | (2012.01) |
| *G16H 40/20* | (2018.01) |
| *G16H 10/60* | (2018.01) |
| *G16H 20/00* | (2018.01) |

(52) U.S. Cl.
CPC ......... *G06F 19/328* (2013.01); *G06Q 20/065* (2013.01); *G06Q 20/10* (2013.01); *G06Q 20/381* (2013.01); *G06Q 30/0206* (2013.01); *G06Q 30/0239* (2013.01); *G06Q 30/0613* (2013.01); *G06Q 30/0629* (2013.01); *G06Q 30/0633* (2013.01); *G06Q 50/22* (2013.01); *G16H 10/60* (2018.01); *G16H 40/20* (2018.01); *G16H 20/00* (2018.01)

(56) References Cited

U.S. PATENT DOCUMENTS

| | | |
|---|---|---|
| 8,494,881 B1 | 7/2013 | Wizig |
| 8,612,267 B1 | 12/2013 | Shrivastava |
| 9,123,072 B2 | 9/2015 | Ketchel, III |
| 2003/0018530 A1 | 1/2003 | Walker et al. |
| 2007/0043595 A1 | 2/2007 | Pederson |
| 2007/0088580 A1 | 4/2007 | Richards, Jr. |
| 2010/0070295 A1 | 3/2010 | Kharraz Tavakol et al. |
| 2011/0106593 A1 | 5/2011 | Schoenberg |
| 2012/0054119 A1 | 3/2012 | Zecchini |
| 2012/0232936 A1 | 9/2012 | Bravata et al. |
| 2012/0239560 A1 | 9/2012 | Pourfallah et al. |
| 2012/0245953 A1 | 9/2012 | Morris |
| 2013/0096937 A1 | 4/2013 | Campbell et al. |
| 2013/0198025 A1 | 8/2013 | Picken |
| 2014/0067406 A1 | 3/2014 | Hyatt et al. |
| 2014/0149135 A1 | 5/2014 | Boerger et al. |
| 2015/0052009 A1 | 2/2015 | Ketchell, III |
| 2015/0178808 A1 | 6/2015 | Grossman et al. |
| 2015/0294338 A1 | 10/2015 | Ketchel, III et al. |
| 2015/0356663 A1 | 12/2015 | Ketchel, III et al. |
| 2016/0027085 A1 | 1/2016 | Ketchel, III et al. |
| 2016/0253731 A1 | 9/2016 | Ketchel, III et al. |

OTHER PUBLICATIONS

International Search Report and Written Opinion received for PCT Patent Application No. PCT/US2015/037751, dated Sep. 17, 2015, 15 pages.

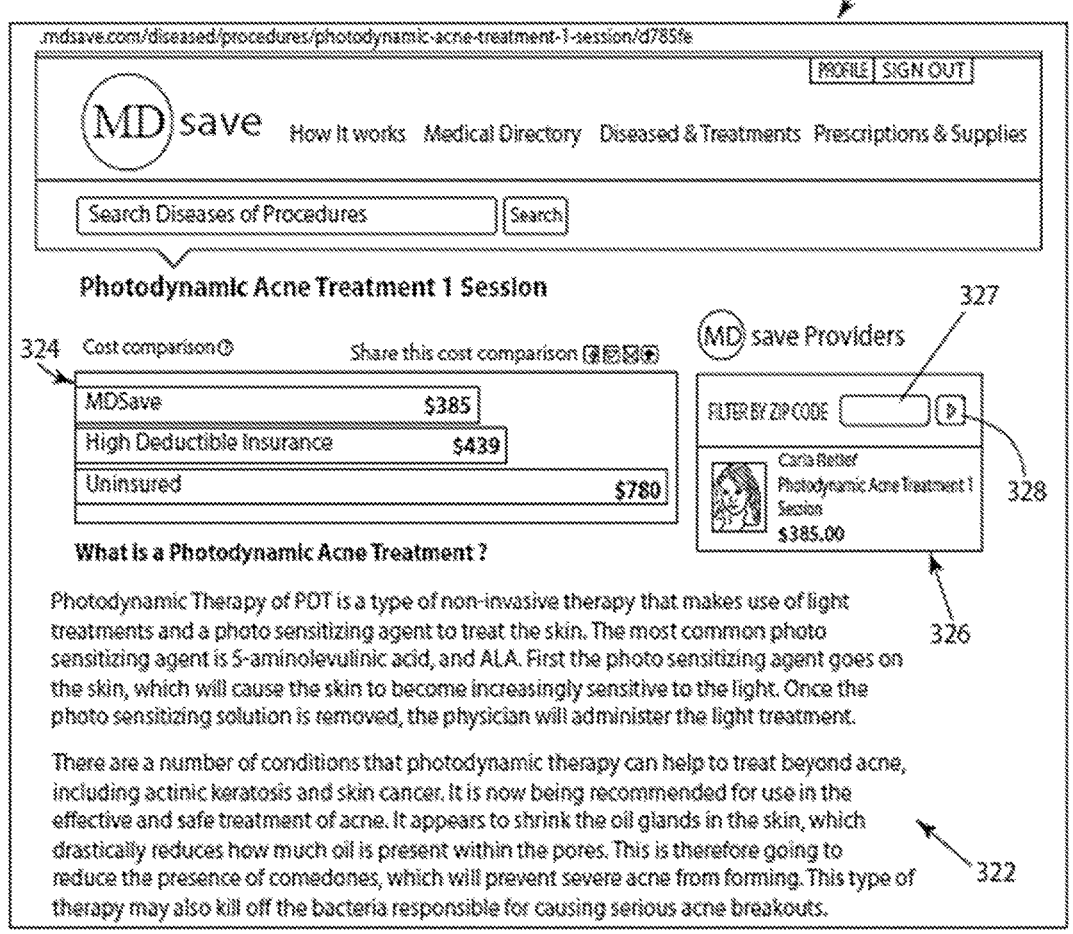

700 702

Radiology ▼

Payout rates listed are suggested rates only. All rates are to be determined by the hospital system.

Specific Locality 704c, 704d — 704 — 706 Recommended Rate

| Facility | Abilene Medical Center | 0.773 | 704b | 706b Facility | 130% |
| Physician | REST OF TEXAS | 0.97 | | 706a Physician | 130% |

704a — 713 — Advanced

☐ Select Mdsave Radiology Group Prking — 712    ∨ Expand all ∧ Collapse all ☐ Export to Excel — 715

| Procedure | Rec. Facility Price | Rec. Phys. Price | MDsave Fee | Total Amount |
|---|---|---|---|---|
| Bone Densiometry | | | 714 | |
| ∨ Bone Density DXA Extremity | $66.68 | $12.60 | $12.00 | $91.28 |

711  DESCRIPTION    CPT CODE    CMS FACILITY    CMS PHYSICIAN    FACILITY REC RATE 130%    PHYSICIAN REC RATE 130%    708

| Dxa bone density/peripheral | 77081 | $59.37 | $11.08 | $66.68 | $13.97 |
| Fracture assessment via dxa | 77086 | $59.37 | $8.90 | $66.68 | $11.22 |
| | | Averages $ | | 66.68 | 12.60 |

711b    711a

| > Bone Density DXA Scan | $103.99 | $16.24 | $12.00 | $132.23 |
| Flouroscopy | | | | |
| > Videofluoroscopic Swallowing Study | $114.21 | $126.69 | $60.00 | $300.90 |
| > Barium Enema with air | $169.58 | $64.02 | $60.00 | $293.60 |
| > Barium Swallow | $114.21 | $29.76 | $60.00 | $203.97 |
| > Cyscogram [VCYG] | $297.90 | $78.45 | $60.00 | $436.35 |
| > Fistulogram | $378.52 | $33.82 | $60.00 | $472.04 |
| > Hysterosalpingogram [HSG] Test | $378.52 | $99.64 | $60.00 | $538.16 |
| > Barium Enema | $169.58 | $44.64 | $60.00 | $274.22 |
| Radiology [X-ray] | | | | |
| > X-ray | $64.41 | $13.20 | $12.00 | $89.61 |
| > Complex X-ray | $102.08 | $18.49 | $12.00 | $132.57 |
| CT | | | | |
| > CT Scan With Contrast | $279.65 | $79.66 | $60.00 | $419.31 |
| > CT Scan With & Without Contrast | $314.92 | $84.62 | $60.00 | $459.54 |
| > CT Scan Without Contrast | $142.04 | $69.15 | $60.00 | $271.19 |
| > CT Scan of Abdomen & Pelvis Without Contrast | $271.55 | $112.03 | $60.00 | $443.58 |
| > CT Scan with Myelogram | $689.90 | $59.05 | $60.00 | $808.95 |
| > CT Scan of Abdomen & Pelvis With and Without Contrast | $438.15 | $129.19 | $60.00 | $627.34 |
| > CT Scan of Abdomen & Pelvis With Contrast | $438.15 | $117.00 | $60.00 | $615.15 |
| CTA | | | | |
| > CT Angiography Cardiac Assessment | $249.34 | $134.38 | $60.00 | $443.72 |
| > CT Coronary Angiography | $249.34 | $150.42 | $60.00 | $459.76 |
| > CT Angiography With and Without Contrast | $327.90 | $117.45 | $60.00 | $505.35 |

[ Email Prices ]  [ Save Changes ]  [ Take Live ]
710a    710b    710c

Fig. 7A 700 702

General Surgery

Payout rates listed are suggested rates only. All rates are to be determined by the hospital system.

| Specific Locality | 704e | 704f | Recommended Rate | |
|---|---|---|---|---|
| | | | 706c | |
| Anesthesia | NATIONAL RATE | 1 | Anesthesia | 100% |
| Facility | Abilene Medical Center | 0.773 | Facility | 130% |
| Physician | REST OF TEXAS | 0.97 | Physician | 130% |

716

☐ Anesthesis

Advanced
∨ Expand all ∧ Collapse all  ☐ Export to Excel

| Procedure | Rec. Facility Price | Rec. Phys. Price | Rec. Anesthesia. Price | MDsave Fee | Total Amount |
|---|---|---|---|---|---|
| General Surgery | | | | | |
| > Colonoscopy | $877.69 | $334.01 | $250.00 | $125.00 | $1,586.70 |
| ∨ Inguinal Hernia Repair | $3,004.76 | $787.49 | $250.00 | $125.00 | $4,167.25 |

| DESCRIPTION | CPT CODE | CMS FACILITY | CMS PHYSICIAN | CMS ANESTHESIA | FACILITY REC RATE 130% | PHYSICIAN REC RATE 130% | ANESTHESIA REC RATE 100% |
|---|---|---|---|---|---|---|---|
| Repair inguina hernia, sliding any age | 49525 | $2,675.43 | $590.67 | $250.00 | $3,004.76 | $744.83 | $250.00 |
| Surgical Repair of Inguinal Hernia | 49505 | $2,675.43 | $536.68 | $250.00 | $3,004.76 | $676.75 | $250.00 |
| Repair recurrent inguinal hernia | 49520 | $2,675.43 | $652.17 | $250.00 | $3,004.76 | $822.39 | $250.00 |
| incarcerated or strangulated | 49521 | $2,675.43 | $739.05 | $250.00 | $3,004.76 | $931.94 | $250.00 |
| incarcerated or strangulated | 49507 | $2,675.43 | $603.90 | $250.00 | $3,004.76 | $761.52 | $250.00 |
| | | | | Averages $ | 3004.76 | 787.49 | 250.00 |

711b  711a  711c

| > Laparoscopic-assisted vaginal hysterectomy | $6,153.59 | $1,047.82 | $250.00 | $125.00 | $7,576.41 |
|---|---|---|---|---|---|
| > Appendectomy | $2,567.30 | $836.81 | $250.00 | $125.00 | $3,779.11 |
| > Hysterectomy Ablation | $4,469.00 | $438.69 | $250.00 | $125.00 | $5,282.69 |
| > Total Abdominal Hysterectomy | $0.00 | $1,384.16 | $250.00 | $125.00 | $1,759.16 |
| > Upper Endoscopy (EGD) | $892.54 | $224.78 | $250.00 | $125.00 | $1,492.32 |
| > Vaginal Hysterectomy | $4,469.00 | $1,169.70 | $250.00 | $125.00 | $6,013.70 |
| > Laparoscopic Cholecystectomy (Laparoscopic Gall Bladder Removal) | $4,244.63 | $1,078.63 | $250.00 | $125.00 | $5,698.26 |
| > Laparoscopic Tubal Ligation | $4,244.63 | $914.81 | $250.00 | $125.00 | $5,534.44 |
| > Laparoscopic Appendectomy | $4,244.63 | $782.25 | $250.00 | $125.00 | $5,401.88 |

Email Prices    Save Changes    Take Live

Fig. 7B 700  702

| GI | |

Payout rates listed are suggested rates only. All rates are to be detemined by the hospital system.

Specific Locality                                    Recommended Rate

Facility   [Abilene Medical Center]  [0.773]          Facility   [130%]
Physician  [REST OF TEXAS]           [0.97]           Physician  [130%]

717

Advanced

○ Anesthesia ● Sedacian ☐ Pathology          ∨ Expand all ∧ Collapse all ☐ Export to Excell

| Procedure | | Rec. Facility Price | Rec. Phys. Price | Pathology Price | MDsave Fee | Total Amount |
|---|---|---|---|---|---|---|
| GI | | | | | | |
| › Colonosopy | | $877.69 | $334.01 | $130.00 | $125.00 | $1,466.70 |
| › Flexible Signoidoscopy | | $704.39 | $143.19 | $130.00 | $125.00 | $1,102.58 |
| ∨ Transnasal Esophagoscopy [TNE] | $837.38 | $119.03 | $0.00 | $125.00 | $1,081.41 | |

| DESCRIPTION | CPT CODE | CMS FACILITY | CMS PHYSICIAN | FACILITY REC. RATE 130% | PHYSICIAN REC. RATE 130% | PATHOLOGY REC. RATE |
|---|---|---|---|---|---|---|
| Esophagoscopy flex doc brush | 43197 | $745.60 | $85.81 | $837.38 | $108.21 | $0.00 |
| Esophagoscopy flex tmsn biopy | 43198 | $745.60 | $102.97 | $837.38 | $129.03 | $0.00 |
| | | | Averages $ | [837.38] | [119.03] | [0.00] |
| | | | | | $125.00 | 711d |

| | | | | | | |
|---|---|---|---|---|---|---|
| › Esophageal Manometry | | $369.20 | $91.98 | $0.00 | $125.00 | $586.18 |
| › Hemorrhoid Banding | | $496.98 | $249.32 | $0.00 | $125.00 | $871.30 |
| › Bravo 48 Hour PH Monitor | | $369.20 | $107.31 | $0.00 | $125.00 | $601.51 |
| › Abdominal Paracentesis | | $549.59 | $120.15 | $130.00 | $125.00 | $924.74 |
| › Hemorrhoidectomy | | $2,180.41 | $513.44 | $0.00 | $125.00 | $2,818.85 |
| › Feeding Tube Placement | | $219.23 | $62.22 | $0.00 | $125.00 | $406.45 |
| › Capsule Encloscopy | | $957.36 | $246.17 | $0.00 | $125.00 | $1,328.53 |
| › Feeding Tube Placement {PEG} | | $1,195.94 | $275.48 | $0.00 | $125.00 | $1,596.42 |
| › Upper Endoscopy [EGD} | | $892.54 | $224.78 | $0.00 | $125.00 | $1,242.32 |
| › EGD with Colonoscopy | | $1,203.96 | $736.42 | $0.00 | $125.00 | $2,065,38 |

[Email Prices]  [Save Changes]  [Take Live]

Fig. 7C

NETWORK-BASED MARKETPLACE SERVICE FOR FACILITATING PURCHASES OF BUNDLED SERVICES AND PRODUCTS

CROSS REFERENCE TO RELATED APPLICATIONS

This application is a continuation of U.S. patent application Ser. No. 14/750,081, filed Jun. 25, 2015, which is a continuation-in-part of U.S. patent application Ser. No. 14/461,209, filed Aug. 15, 2014, which claims the benefit of U.S. Provisional Patent Application Ser. No. 61/866,922, filed Aug. 16, 2013, the contents of all incorporated herein in their entirety by reference thereto.

BACKGROUND OF THE INVENTION

Exemplary embodiments of the present invention relate to the marketing and facilitating the sale of services and products. More specifically, exemplary embodiments relate to methods and apparatuses for providing a web-based mechanism allowing prospective patients to search for and compare healthcare services and products offered by local providers, including bundled sets of services, and facilitating prepaid purchases of such healthcare services and products by prospective patients at discounted rates.

The price of healthcare services varies depending on specialty, procedure, and physician practice. In the United States, many patients do not have access to a simple way to shop and compare the price of common medical procedures. Due to the current managed care based payor system in the US, the cost of treatment is often determined by managed care organizations. These managed care organizations have specific formularies for drugs and procedures designed specifically to patients' individual health plans, which restrict the drugs and procedures available to patients in their particular plans. Patients have historically had no access to these price lists or formularies and have had very few tools to assist them in finding and comparing health care services or predetermining the cost of a procedure. Currently prospective patients who chose to compare medical costs are forced to conduct extensive, often inefficient and time consuming research to compare medical procedures prior to treatment.

The rising cost of healthcare is having a dramatic effect on the U.S. healthcare system. Healthcare costs continue to outpace pace inflationary growth, provider reimbursement rates continue to fall, and the cost of patient insurance premiums are increasing. To lower monthly premium costs, many patients are choosing to purchase (and employers are choosing to offer) high deductible health plans as an alternative to traditional higher premium PPO health plans. These high deductible plans require patients to pay cash payments for medical services until the high deductible is satisfied, and once this deductible has been met, the insurance carrier begins to cover medical costs. As a result, many patients are seeing exponential increases in out-of-pocket expenses for medical procedures and services. In addition to more patients selecting high deductible plans, many patients cannot afford increased payments and are becoming uninsured or underinsured. As the number of patients who are uninsured, underinsured, or on high deductible plans grows, the need for a mechanism that allows patients to find discount medical services increases.

SUMMARY OF THE INVENTION

Exemplary embodiments of the present invention are related to an apparatus for facilitating purchases of services offered by service providers. The apparatus includes an application server providing a network service that is accessible to a plurality of users through a plurality of client systems communicatively coupled to the application server via a network and a data storage system storing a service offer database that is maintained by the application server. The service offer database comprises a plurality of service offer information records respectively associated with a plurality of service offers. The plurality of service offers includes at least one service offer for a bundled set of services. Each service offer information record comprises an indication of a primary service of the associated service offer, a purchase price for the associated service offer, a payment amount for the primary service, and compensation information for the primary service. Upon being accessed by a user of one of the client systems, the network service is operable to receive an indication from the client system of a selected service offer being selected from the plurality of service offers for purchase by the user. Upon receiving purchase information for the user specifying a funding source to use for purchasing the selected service offer from the client system, the network service is operable to issue a request to the funding source for funds corresponding to the purchase price included in the service offer information record associated with the selected service offer to process a purchase of the selected service offer by the user.

In exemplary embodiments, the application server implements a web application to provide the network service, and each client systems implements a client application configured to provide a web-based user interface for accessing the network service provided by the application server via the web application.

In exemplary embodiments, each service offer for a bundled set of services comprises a bundled set of healthcare services provided by corresponding healthcare service providers.

In exemplary embodiments, upon receiving a notification from one of the client systems that the primary service of the selected service offer has been performed, the network service operates to access a servicer for a financial account indicated by the compensation information for the primary service in the service offer information record associated with the selected service offer to direct a disbursement of funds corresponding to the payment amount for the primary service to the financial account.

In exemplary embodiments, each service offer information record associated with a service offer for a bundled set of services further comprises, for each of one or more secondary services associated with the primary service of the associated service offer, an indication of the secondary service, a payment amount for the secondary service, and corresponding compensation information for the secondary service. If the selected service offer is a service offer for a bundled set of services, upon receiving a notification from one of the client systems that any secondary service associated with the primary service of the selected service offer has been performed, the network service operates to access a servicer for a financial account indicated by the corresponding compensation information for the secondary service in the service offer information record associated with the selected service offer to direct a disbursement of funds corresponding to the payment amount for the secondary service to the financial account.

In exemplary embodiments, at least one service offer information record associated with a service offer for a bundled set of services further comprises an indication of a facility for performing the primary service, a facility fee for the facility, and compensation information for the facility fee. If the selected service offer is a service offer for a bundled set of services for which the associated service offer information record includes an indication of a facility for performing the primary service, upon receiving a notification from one of the client systems that the primary service of the selected service offer has been performed, the network service operates to access a servicer for a financial account indicated by the compensation information for the facility fee in the service offer information record to direct a disbursement of funds corresponding to the facility fee to the financial account.

In exemplary embodiments, at least one service offer information record associated with a service offer for a bundled set of services further comprises an indication that at least one of the secondary services associated with the primary service is an optional secondary service. If the selected service offer is a service offer for a bundled set of services for which at least one of the secondary services is an optional service, the network service is further operable to receive an indication from the user of the client system, for each optional secondary service of the service offer, of whether the optional secondary service is to be included in the purchase of the selected service offer.

In exemplary embodiments, the data storage system stores a profile database that is maintained by the application server. The profile database comprises a respective account information record for each of a plurality of user accounts registered with the application server. The plurality of user accounts include a plurality of customer accounts and a plurality of provider accounts. The account information record for each user account comprising information for authorizing a user accessing the network service from one of the client systems to access the network service in association with the user account.

In exemplary embodiments, the network service is operable to allow a user accessing the network service from one of the client systems in association with a provider account to create a service offer for purchase via the network service by submitting a set of information for the service offer to the network service and, in response to receiving the set of information for the service offer, establish a service offer information record associated with the service offer and the provider account within the service offer database.

In exemplary embodiments, each service offer information record further comprises an indication of a corresponding service provider for the primary service, and each service offer information record associated with a service offer for a bundled set of services further comprises, for each of the one or more secondary services associated with the primary service of the service offer, an indication of a corresponding service provider for the secondary service.

In exemplary embodiments, the plurality of provider accounts includes a plurality of physician accounts and a plurality of practice group accounts, the account information record for each practice group account comprises an indication of one or more of the physician accounts being affiliated with the practice group account, and the network service provides functionality for allowing a user accessing the network service from one of the client systems in association with a practice group account to create a service offer for purchase via the network service in which the set of information for the service offer submitted to the network service specifies one of the physician accounts affiliated with the practice group account as the corresponding service provider for the primary service.

In exemplary embodiments, the data storage system stores a transaction information database that is maintained by the application server. The transaction information database comprises a respective purchase information record for each processed purchase, by a user accessing the network service from one of the client systems in association with a customer account, of a service offer that has been created by a user accessing the network service from one of the client systems in association with a provider account, the respective purchase information record for each processed purchase comprising an indication of the service offer information record associated with the purchased service offer and, for each of the primary service and any secondary service of the service offer, and an indication of whether the purchase has been redeemed with respect to the service.

In exemplary embodiments, the network service, upon being accessed by a user of one of the client systems to process a purchase of a service offer, generates a voucher for the user that specifies a unique confirmation number for the purchase and the corresponding service provider for each of the primary service and any secondary service of the purchased service offer, and, for each of the primary service and any secondary service of the purchased service offer, sets the purchase information record for the processed purchase to indicate that the purchase has not been redeemed with respect to the service.

Exemplary embodiments of the present invention that are related to computer-implemented processes and computer systems corresponding to the above-summarized exemplary embodiments directed to an apparatus are also described and claimed herein.

The above-described and other features and advantages realized through the techniques of the present disclosure will be better appreciated and understood with reference to the following detailed description, drawings, and appended claims. Additional features and advantages are realized through the techniques of the present invention. Other embodiments and aspects of the invention are described in detail herein and are considered a part of the claimed invention.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description of exemplary embodiments of the present invention taken in conjunction with the accompanying drawings in which:

FIGS. 3A-3D are a number of screen shots illustrating examples of a graphical user interfaces that may be implemented by services provided within a customer portal in accordance with exemplary embodiments of the present invention;

FIGS. 7A-7C are a number of screen shots illustrating examples of a graphical user interfaces that may be implemented by services provided within a provider portal in accordance with exemplary embodiments of the present invention.

Figure 1:
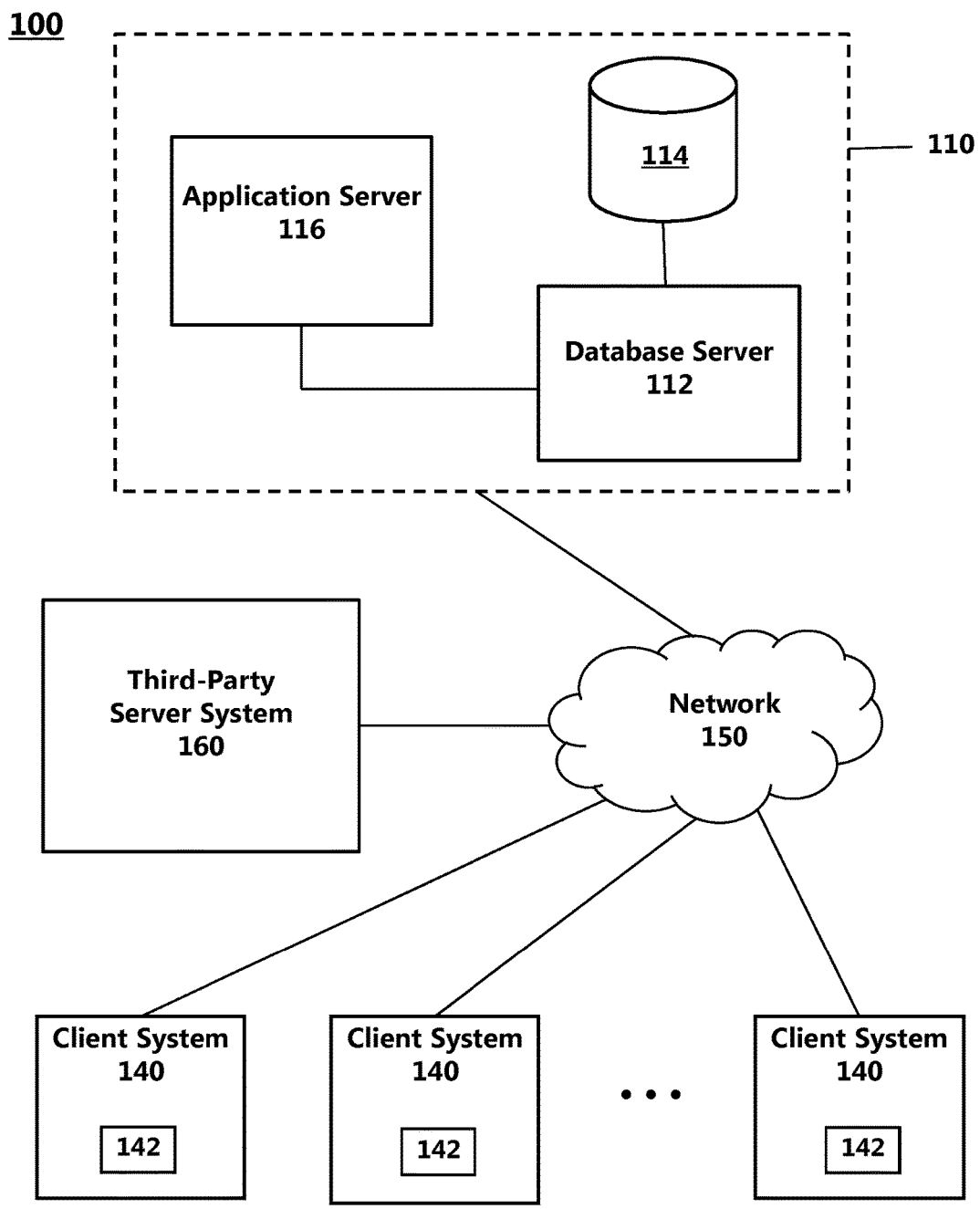
FIG. 1 is a schematic diagram illustrating an example network architecture for a healthcare marketplace system that can be configured to implement exemplary embodiments of the present invention.

The detailed description explains exemplary embodiments of the present invention, together with advantages and features, by way of example with reference to the drawings, in which similar numbers refer to similar parts throughout the drawings. The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered to be within the scope of the claimed invention.

DETAILED DESCRIPTION

While the specification concludes with claims defining the features of the invention that are regarded as novel, it is believed that the invention will be better understood from a consideration of the description of exemplary embodiments in conjunction with drawings. It is of course to be understood that the embodiments described herein are merely exemplary of the invention, which can be embodied in various forms. Therefore, specific structural and functional details disclosed in relation to the exemplary embodiments described herein are not to be interpreted as limiting, but merely as a representative basis for teaching one skilled in the art to variously employ the present invention in virtually any appropriate form, and it will be apparent to those skilled in the art that the present invention may be practiced without these specific details. Further, the terms and phrases used herein are not intended to be limiting but rather to provide an understandable description of the invention.

Exemplary embodiments of a transactional marketplace system in accordance with the present invention will now be described with reference to the drawings. Exemplary embodiments of the present invention may be implemented to provide healthcare service providers and pharmacies with a mechanism to remotely offer healthcare services and products to prospective patients at discounted rates in exchange for prepayment of the costs for the services and products via a network-based application (for example, a web-based application). In this regard, exemplary embodiments may further be implemented to provide prospective patients with a mechanism to remotely search, compare, and make pre-paid purchases of such healthcare services and products offered by local medical service providers and pharmacies via a network-connected device configured to access the network-based application. Exemplary embodiments may be further implemented to provide healthcare service providers with the ability to remotely offer a bundled set of healthcare services that are performed separately by multiple providers to prospective patients through such a network-based mechanism in which the patient is provided the opportunity to make a prepaid purchase of such a bundled set of services in a single transaction via the network-connected device, whereby the network-based application facilitates a disbursed distribution of the payment among the multiple healthcare service providers that perform services included in the bundled set of services.

Exemplary embodiments may be further implemented to provide various types of healthcare service providers, which may include individual physicians, practice groups, and hospital systems, with the ability to establish affiliations with one another through such a network-based mechanism and provide various options allowing the service providers to remotely offer healthcare services in association with these affiliations.

It should further be noted that various aspects of exemplary embodiments of the present invention described herein are not limited to healthcare services (also referred to herein as procedures) and products but, rather, may be implemented with respect to any suitable classes and types of services and products that may be offered by any suitable classes and types of service providers and retailers.

Referring now to FIG. 1, a schematic diagram illustrating an example network architecture for a healthcare marketplace system 100 that can be configured to implement exemplary embodiments of the present invention is provided. It should of course be understood that FIG. 1 is intended as an example, not as an architectural limitation for different embodiments of the present invention, and therefore, the particular elements depicted in FIG. 1 should not be considered limiting with regard to the environments within which exemplary embodiments of the present invention may be implemented.

In the example illustrated in FIG. 1, healthcare marketplace system 100 is implemented as a client/server system that includes a central server system 110 that is commonly accessed by each user of the system through operation of any of a plurality of client systems 140 that are operatively coupled to the central server system via a communication network 150. Central server system 110 further includes a database server 112 that is coupled to a data store 114 and an application server 116, and each client system 140 is a user terminal or other client device implementing software for and running a respective client application 142 for accessing services provided via a network-based application (also referred to herein as a network service) implemented by application server 116. Such client applications may also be referred to as client modules, or simply clients, and may be implemented in a variety of ways. In exemplary embodiments, such client applications can be implemented as any of a myriad of suitable client application types, which range from proprietary client applications (thick clients) to web-based interfaces in which the user agent function is provided by a web server and/or a back-end program (for example, a CGI program).

As further illustrated, exemplary marketplace system 100 may also include at least one third-party server system 160 to enable other functionality that may be accessed and utilized by server system 110 to provide and/or enhance the network service discussed herein. In exemplary embodiments, marketplace system 100 can include additional servers, clients, and other devices not shown in FIG. 1. The particular architecture depicted in FIG. 1 is provided as an example for illustrative purposes and, in exemplary embodiments, any number of client systems 140 may be connected to server system 110 at any given time via network 150, and server system 110 can comprise multiple server components and databases located within a single server system or within multiple server systems, where the multiple server systems are integrated with or accessible by users of client systems 140 as a distributed server system via network 150.

In exemplary embodiments, network 150 can be configured to facilitate communications between server system 110 and client systems 140, as well as communications with and between other devices and computers connected together within marketplace system 100, by any suitable wired (including optical fiber), wireless technology, or any suitable combination thereof, including, but not limited to, personal area networks (PANs), local area networks (LANs), wireless networks, wide-area networks (WAN), the Internet (a network of heterogeneous networks using the Internet Protocol, IP), and virtual private networks, and the network may also utilize any suitable hardware, software, and firmware technology to connect devices such as, for example, optical fiber, Ethernet, ISDN (Integrated Services Digital Network), T-1 or T-3 link, FDDI (Fiber Distributed Data Network), cable or wireless LMDS network, Wireless LAN, Wireless PAN (for example, IrDA, Bluetooth, Wireless USB, Z-Wave and ZigBee), HomePNA, Power line communication, or telephone line network. Such a network connection can include intranets, extranets, and the Internet, may contain any number of network infrastructure elements including routers, switches, gateways, etc., can comprise a circuit switched network, such as the Public Service Telephone Network (PSTN), a packet switched network, such as the global Internet, a private WAN or LAN, a telecommunications network, a broadcast network, or a point-to-point network, and may utilize a variety of networking protocols now available or later developed including, but not limited to the Transmission Control Protocol/Internet Protocol (TCP/IP) suite of protocols for communication.

In exemplary embodiments, application server 116, database server 112, and any other servers employed within server system 110 and third-party servers utilized within marketplace system 100 can be implemented within any suitable computing system or systems such as a workstation computer, a mainframe computer, a server system (for example, SUN ULTRA workstations running the SUN operating system, IBM RS/6000 workstations and servers running the AIX operating system, or an IBM zSeries eServer running z/OS, z/VM, or LINUX OS), a server cluster, a distributed computing system, a cloud based computing system, or the like, as well as any of the various types of computing systems and devices described below with reference to the client systems 140. Server system 110 may be implemented using any of a variety of architectures. For example, application server 116 and database server 112 may also be implemented independently or as a single, integrated device. While the exemplary embodiment illustrated in FIG. 1 depicts application server 116 and database server 112 as individual components, the applications provided by these servers, or various combinations of these applications, may actually be server applications running on separate physical devices. In this regard, server system 110 may comprise a number of computers connected together via a network and, therefore, may exist as multiple separate logical and/or physical units, and/or as multiple servers acting in concert or independently, wherein each server may be comprised of multiple separate logical and/or physical units. In exemplary embodiments, server system 110 can be connected to network 150 through a collection of suitable security appliances, which may be implemented in hardware, software, or a combination of hardware and software.

As illustrated in FIG. 1, application server 116 is communicatively coupled to database server 112. Database server 112 is connected to data store 114, which comprises a plurality of databases that are maintained by database server 112, accessed by application server 116 via database services provided at a front end by database server 112, and store information on a variety of matters that is utilized in providing the services offered via the network service provided by the application server, as described below in greater detail. As used herein, the term "data store," "data storage unit," storage device", and the like can to any suitable memory device that may be used for storing data, including manual files, machine-readable files, and databases. In exemplary embodiments, application server 116, database server 112, and data store 114 may implemented together a single computing device, implemented within a plurality of computing devices locally coupled to each other via a suitable communication medium, such as a serial port cable, telephone line or wireless frequency transceiver, implemented within a plurality of computing devices remotely coupled to each other via network 150, or any suitable combination thereof.

Client systems 140 are computer devices to which one or more users, which may be healthcare providers offering services or products or patients seeking to purchase healthcare services or products, or their human agents (for example, personal representatives or assistants), have access. It should be noted that the term "user" is used herein to refer to one who uses a computer system, such as one of client systems 140. As described in greater detail below, client systems 140 are each operable by such users to access server system 110 via network 150 and act as clients to access services offered by the network service provided by the server system within exemplary marketplace system 100. For this purpose, each client system includes a respective client application 142 that executes on the client system and allows a user to interact with server system 110 via application server 116.

In exemplary embodiments, the computer systems of client systems 140 can be any of a wide range of suitable computing devices such as one or more workstations, desktop computers, laptops, or other personal computers (PCs) (for example, IBM or compatible PC workstations running the MICROSOFT WINDOWS operating system or LINUX OS, MACINTOSH computers running the MAC OSX operating system, or equivalent), non-traditional-computer digital devices such as Personal Digital Assistants (PDAs) and other handheld or portable electronic devices, smart phones and other mobile handsets, tablet computers, netbook computers, game consoles, home theater PCs, desktop replacement computers, and the like, or any other suitable information processing devices. An exemplary computer system for client systems 140 is described in greater detail below with reference to FIG. 5.

In general, during operation of exemplary marketplace system 100, a client system 140 first establishes a connection to server system 110 via network 150. Once the connection has been established, the connected client system may directly or indirectly transmit data to and access content from the application server 116. A user accessing application server 116 through the connected client system can thereby to use a client application 142 to access services provided by the application server, which are described in greater detail below, via a user interface implemented by the client application within which the client application renders the information served by the application server.

In exemplary embodiments, application server 116 can implement network service as a non-web client application (such as a mobile application), a web client application, or both to provide the services accessed by client systems 140 within server system 110, and client applications 142 can correspondingly be implemented as non-web client applications, web client applications, or both for operation by users of the client systems to interact with application server 116 and access the services provided thereby. For example, application server 116 can comprise a web server configured to provide a web application for the respective client applications implemented on client systems 140 that are configured to provide web-based user interfaces for utilizing the services provided by the web server. For instance, the user interfaces of client applications implemented on client systems 140 can be configured to provide various options corresponding to the functionality offered in exemplary embodiments described herein through suitable user interface controls (for example, by way of menu selection, point-and-click, dialog box, or keyboard command). In one general example, the user interfaces may provide "send" or "submit" buttons that allow users of client applications to transmit requested information to application server 116. The user interfaces can be implemented, for example, as a graphical user interface (GUI) that renders a common display structure to represent the network service provided by application server 116 for a user of a client platform.

More specifically, in such an example, application server 116 can, for example, be configured to provide services via a web-based software application hosting a corresponding website that includes a number of web pages (e.g., screens), and client applications 142 can comprise a web browser executing on client systems 140, such that the services provided by application server 116 are accessible to client systems 114 using the Internet or an intranet. Users of client systems 140 may thereby access the website provided by application server 116 by, for example, inputting or following a link to the uniform resource locator (URL) for the website in the web browser, which then enable users to display and interact with information, media, and other content embedded within the web pages of the website provided by application server 116. The web-based software application can transmit information that can be processed by the web browsers to render a user interface using, for example, a browser-supported programming languages such as JavaScript, HTML, HTML5, and CSS, or the like, and can communicate with the web browsers using, for example, HTTPS, POST and/or GET requests. Client applications 142 and application server 116 may be configured so that information transmitted between client systems 140 and server system 110 can be encrypted and sent over a secure network connection to protect, for example, patient privacy.

Figure 2:
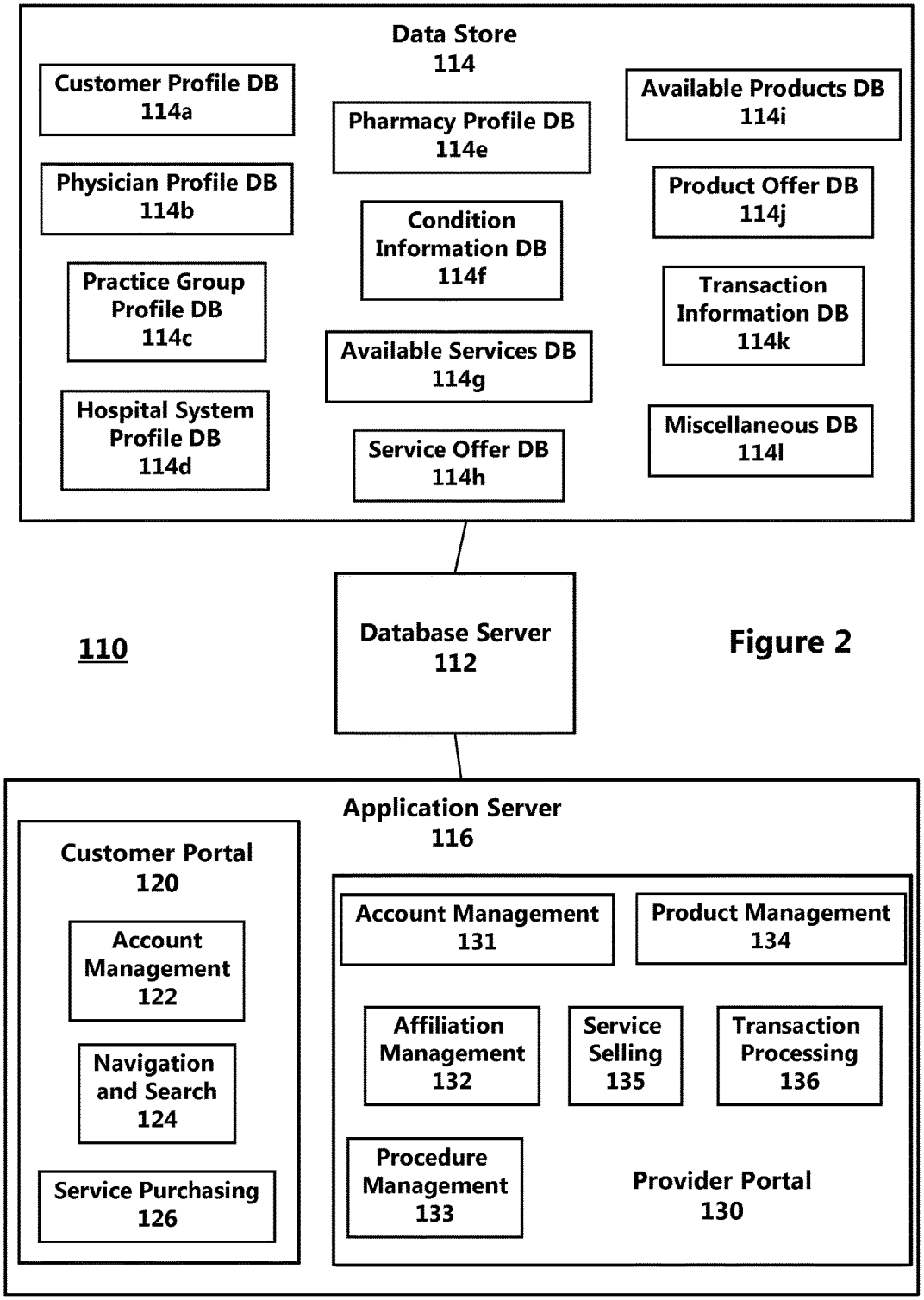
FIG. 2 is a block diagram illustrating a server system in accordance with an exemplary embodiment of the present invention.

Referring now to FIG. 2, a block diagram illustrating an exemplary embodiment of server system 110 is provided. As illustrated in FIG. 2, application server 116 is implemented to provide a plurality of services via a customer portal 120 and a plurality of services via a provider portal 130. As described herein, application server 116 can be implemented to provide a respective set services for each of various types of users (for example, unregistered guests, customers, individual physicians, nurses, office staff, practice group administrators, hospital system administrators, pharmacy administrators, and the like), and some of the services offered by application server 116 can be commonly applicable to and accessible by all types of users, while other services can be applicable to and accessible only by specific types of users. For purposes of description, the terms "providers" and "provider users" are used herein to refer to the general class of users that register with the system offer healthcare services or products for purchase by customer users registered with the system, which can include individual physician users, practice group administrators, hospital system administrators, pharmacy administrators, and the like. In addition, a user account for a particular provider can have any number of authorized users. As an example, an account established for a physician can have the physician as one of its users. It can also have nurses or office staff working for the physician as other authorized users. The other authorized users can log into the account and perform various actions with the permission and under the supervision of the physician. A single hospital system account may be established and shared by multiple staff members hospital system. For purpose of illustration, there can be a designated user (for example, an account administrator) who is responsible for managing the account. The administrator can be provided with greater access rights within server system 110 with respect to the account. In exemplary embodiments, the particular client applications 142 or the particular client systems 140 that are utilized for accessing application server 116 can be respective to and customized for each type of user account. For example, the particular client application that is utilized for each type of account can be implemented to a provide virtual computing platform that is specific to the services offered for that type of account.

As further illustrated in exemplary embodiment of FIG. 2, and as will described in greater detail below, the services provided via customer portal 120 include a registration and account management service 122, a navigation and search service 124, and a purchasing service 126, and the services provided via provider portal 130 include a registration and account management service 131, an affiliation management service 132, a procedure management service 133, a product management service 134, a service selling service 135, and a transaction processing service 136. As discussed above, application server 116 can implement a web-based application (for example, hosting a corresponding website that includes a number of web pages), and a client system 140 can include a web browser that renders a user interface implemented by the web-based application for allowing users access the services provided by the application server.

As further illustrated in exemplary embodiment of FIG. 2, and as will also be described in greater detail below, data store 114 comprises a plurality of databases that are maintained and accessible by application server 116 via database server 112, including a customer profile database 114a, a physician profile database 114b, a practice group profile database 114c, a hospital system profile database 114d, a pharmacy profile database 114e, a condition information database 114f, an available services database 114g, a service offer database 114h, an available products database 114i, a product offer database 114j, a transaction information database 114k, and one or more additional databases 114l that may be used for storing any other suitable information that may be utilized by server system 110 (for example, system usage data, audit trail data, data used internally within the system by application server 116, and the like). In exemplary embodiments, the various databases maintained within data store 114 can be maintained as groups within one or more larger databases or maintained individually. For example, customer profile database 114a, a physician profile database 114b, a practice group profile database 114c, hospital system profile database 114d, and pharmacy profile database 114e may be maintained a as a group within a general profile database that is maintained within data store 114.

As discussed below, application server 116 can be configured to maintain various types of information records within the plurality of databases. An information record may be, for example, a program and/or data structure that tracks various data related to a corresponding type of information record. As used herein, the terms "data," "content," "information" and similar terms may be used interchangeably to refer to data capable of being captured, transmitted, received, displayed, and/or stored in accordance with various example embodiments. Thus, use of any such terms should not be taken to limit the spirit and scope of the disclosure. Further, where a computing device is described herein to receive data from another computing device, it will be appreciated that the data may be received directly from the another computing device or may be received indirectly via one or more intermediary computing devices, such as, for example, one or more servers, relays, routers, network access points, base stations, and/or the like. Similarly, where a computing device is described herein to send data to another computing device, it will be appreciated that the data may be sent directly to the another computing device or may be sent indirectly via one or more intermediary computing devices, such as, for example, one or more servers, relays, routers, network access points, base stations, and/or the like.

As noted above, different types of users can access server system 110. As such, application server 116 can be configured to maintain and manage account information records for a variety of types of users that register with the system according to certain categories of accounts. In the present exemplary embodiment, customer profile database 114a is used to maintain account information records for customer users that register with server system 110 to purchase healthcare services and products being offered by provider users registered with the system. For each customer for which an account is registered with server system 110, various items of information relevant to the customer, such as name, address or location information, contact information, billing information, and any other suitable identifying information, as well as a unique user name and password associated with the account that can be used to log into the account, can be included in the respective account information record for the customer that is maintained within customer profile database 114a. The account information record for each customer can also be associated with a unique customer account identifier within customer profile database 114a that is used by application server 116 for performing various operations.

Physician profile database 114b is used to maintain account information records for individual physician users that register with server system 110 to offer healthcare services for purchase by customer users registered with the system, as well as account information records for individual physicians that are registered with the system in association with a practice group or hospital system (as described in greater detail below). For each physician for which an account is registered with server system 110, various items of information relevant to the physician, such as name, practice specialty, office location(s) and hours, a profile picture, contact information, biographical information (such as awards, honors, publications, patient testimonials, and other information that can be helpful for marketing the physician to customers accessing the system), URLs or references to websites and social media profiles, group practice and hospital affiliation(s), outside facilities that are used for particular procedures performed by the physician (for example, particular hospitals or clinics), compensation information (indicating a financial account for receiving payment for purchases of services offered by the physician via the system), and any other suitable identifying information, as well as a unique user name and password associated with the account that can be used to log into the account, may be included in the respective account information record for the physician that is maintained within physician profile database 114b. The account information record for each physician can also be associated with an account status and a unique physician account identifier within physician profile database 114b that is used by application server 116 for performing various operations.

Practice group profile database 114c is used to maintain account information records for practice group administrator users that register with server system 110 to offer healthcare services provided by physicians affiliated with a practice group for purchase by customer users registered with the system. For each practice group for which an account is registered with server system 110, various items of information relevant to the practice, such as practice group name, location and hours, contact information, URLs or references to websites and social media profiles for the practice group, physician and hospital affiliation(s), outside facilities that are used for particular procedures performed by physicians affiliated with the practice group, compensation information (indicating a financial account for receiving payment for purchases of services offered by affiliated physicians via the system), and any other suitable identifying information, as well as a unique user name and password associated with the account that can be used by the practice group administrator to log into the account, may be included in the respective account information record for the practice group that is maintained within practice group profile database 114c. The account information record for each practice group can also be associated with an account status and a unique practice group account identifier within practice group profile database 114c that may be used by physician users registered with the system for affiliating with the practice group and used by application server 116 for performing various operations.

Hospital system profile database 114d is used to maintain account information records for hospital system administrator users that register with server system 110 to make on-site, in-person sales of pre-paid healthcare services provided by physicians affiliated with a hospital system for purchase by patients operating client systems within marketplace system 100. For each hospital system for which an account is registered with server system 110, various items of information relevant to the hospital system, such as practice group and physician affiliation(s), facilities that are used for particular procedures performed by physicians affiliated with the hospital system, compensation information (indicating a financial account for receiving payment for purchases of services offered by affiliated physicians via the system), and any other suitable identifying information, as well as a unique user name and password associated with the account that can be used by the hospital system administrator to log into the account, may be included in the respective account information record for the hospital system that is maintained within hospital system profile database 114d. The respective account information record for the hospital system may further include a plurality of unique user names and passwords associated with the account that can be respectively used by hospital system staff members to log into the account The account information record for each hospital system can also be associated with an account status and a unique hospital system account identifier within hospital system profile database 114d that may be used by physician users registered with the system for affiliating with the hospital system and used by application server 116 for performing various operations.

Pharmacy profile database 114e is used to maintain account information records for pharmacy administrators that register with server system 110 to offer healthcare products, such as prescription drugs and medical supplies, for purchase by customer users registered with the system. For each pharmacy for which an account is registered with server system 110, various items of information relevant to the pharmacy, such as name, location(s) and hours, contact information, URLs or references to websites and social media profiles, compensation information (indicating a financial account for receiving payment for purchases of products offered by the pharmacy via the system), and any other suitable identifying information, as well as a unique user name and password associated with the account that can be used to log into the account, may be included in the respective account information record for the pharmacy that is maintained within pharmacy profile database 114e. The account information record for each pharmacy can also be associated with an account status and a unique pharmacy account identifier within pharmacy profile database 114e that is used by application server 116 for performing various operations.

Condition information database 114f is used to maintain information records for various health conditions and diseases for which corresponding healthcare services (for example, test and treatments) that can be offered by providers registered with server system 110 for purchase by customer users registered with the system. In exemplary embodiments, the various conditions and diseases for which respective information records are maintained in condition information database 114f and the information that populates the respective information record for each condition or disease can be created and maintained by a back-end administrator of server system 110. For each condition or disease for which an information record is created, various items of information relevant to the condition or disease, such as name, description, causes, risk factors, symptoms, common treatments, corresponding healthcare services that can be offered by providers registered with server system 110 (for example, each associated healthcare service may be identified within the information record using a unique procedure identifier that is used to identify an information record for the service within available services database 114g as discussed below), and any other suitable information may be included in the respective information record for the condition or disease that is maintained within condition information database 114f.

Available services database 114g is used to maintain information records for various healthcare services (for example, tests and treatments) that can be offered by providers registered with server system 110 for purchase by customer users registered with the server system. In exemplary embodiments, the respective information records for healthcare services that are maintained in available services database 114g and the information that populates the respective information record for each service can be created and maintained by a back-end administrator of server system 110. For each service for which an information record is created, various items of information relevant to the service, such as name, procedure detail, one or more medical specialties with which the procedure is commonly associated, cost information (for example, average prices for the service for patients that are uninsured and/or have a high deductible insurance plan and an average price for purchasing the service that is offered by providers registered with server system 110), a medical code number identifying the service according to the nomenclature used by a formal medical classification system (for example, a code that is used to identify the service according to the Current Procedural Terminology (CPT) code set), a procedure identifier that is used by application server 116 to uniquely identify the particular service, and any other suitable information may be included in the respective information record for the service that is maintained within available services database 114g.

Additionally, in exemplary embodiments, the information record for each service that is maintained within available services database 114g may further include an indication of whether the service can be offered by providers within marketplace system 100 as an individual primary service or as a primary service of a bundled set of a plurality of services (for which a single payment for the bundled set of services will be disbursed to different provider for each of the services in the bundled set). In such embodiments, for each service for which the information record includes an indication that the service is offered as a primary service of a bundled set of services, various items of additional information relevant to the bundled set of services associated with the service that is indicated to be a primary service may be included in the respective information record for the primary service that is maintained within available services database 114g. Such items of information relevant to the bundled set of services included in the respective information record for a primary service may include, for example, items of information describing one or more secondary services associated with the primary service (such as name, a medical code number such as a CPT code identifying the service according to the nomenclature used by a formal medical classification system, and a secondary procedure identifier that is used by application server 116 to uniquely identify the particular secondary service in association with the unique procedure identifier for the primary service), one or more procedure identifiers for other services for which an information record is maintained within available services database 114g that are considered to be secondary services associated with the primary service, an indication of whether performance of each of the one or more secondary services (for which a single customer payment for the bundled set of services will be disbursed among different respective providers for the services in the bundled set) is optional or required in association with performance of the primary service, and an indication of whether the primary service is required to be performed at an outside facility. In addition, in such embodiments, for each service for which the information record includes an indication that the service is offered as a primary service of a bundled set of services, the cost information that is included in the respective information record for the primary service that is maintained within available services database 114g can include respective cost information for each of the primary service, the one or secondary services, and, if required, the use of an outside facility for the primary service individually (for example, average prices for each service and facility of the bundled set of services for patients that are uninsured and/or have a high deductible insurance plan) in addition to an average price for purchasing the bundled set of services that is offered by providers registered with server system 110.

Service offer database 114h is used to maintain information records for healthcare services that are being offered by providers registered with the system for purchase by customer users registered with the system. In this regard, it should be noted that the same service may be separately offered by multiple different providers registered with the system and, thus, service offer database 114*h* can include multiple information records for the same service that are each associated with a different provider. For each offered service for which a respective information record is maintained within service offer database 114*h*, various items of information relevant to the service being offered, such as the unique procedure identifier for the information record within available services database 114*g* for the service, the unique account identifier for the account information record (within physician profile database 114*b*, practice group profile database 114*c*, or hospital system profile database 114*d*) of the provider that is offering the service through the system, the unique physician account identifier for the account information record within physician profile database 114*b* of the physician user that will perform the service, a location at which the service will be performed, a discounted price for purchasing the service within marketplace system 100, a regular price for the service when the service is purchased outside of the system, the unique account identifier for the account information record (within physician profile database 114*b*, practice group profile database 114*c*, or hospital system profile database 114*d*) of the provider for which payment for the service when purchased through the system is to be directed, a payment amount to be transferred to the provider for which payment for performing the service is to be directed, additional descriptive information that may be provided by the provider offering the service, a procedure offer identifier that is used by application server 116 to uniquely identify the offering of the particular service by the provider within the system, and any other suitable information may be included in the respective information record for the offered service that is maintained within service offer database 114*h*.

Additionally, in exemplary embodiments, the information records for offered services that are maintained within service offer database 114*h* can include information records that include additional information for services that are offered by providers registered with the system as a bundled set of services. In this regard, the information record for each offered service that is maintained within service offer database 114*h* may further include an indication of whether the offered service is being offered as an individual primary service or as a primary service of a bundled set of a plurality of services (for which a single customer payment for the bundled set of services will be disbursed among different respective providers for the services in the bundled set). In such embodiments, for each offered service for which the information record includes an indication that the service is being offered by a provider as a primary service of a bundled set of services, various items of additional information relevant to the bundled set of services associated with the offered service that is indicated to be a primary service may be included in the respective information record for the offered service that is maintained within service offer database 114*h*. Such items of information relevant to the bundled set of services included in the respective information record for an offered service within service offer database 114*h* that is indicated to be a primary service of a bundled set of services may include, for example, items of information for each secondary service such as the unique procedure identifier for the information record within available services database 114*g* for the secondary service (or the secondary procedure identifier that is included in the available services database 114*g* to uniquely identify the particular secondary service in association with the unique procedure identifier for the offered primary service where the information record for the primary service being offered in the available services database 114*g* includes an indication that the service is offered as a primary service of a bundled set of services), the unique physician account identifier for the account information record within physician profile database 114*b* of the physician user that will perform the secondary service, a location at which the service will be performed, a discounted price for purchasing the secondary service within marketplace system 100, a regular price for the secondary service when the service is purchased outside of the system, the unique account identifier for the account information record (within physician profile database 114*b*, practice group profile database 114*c*, or hospital system profile database 114*d*) of the provider for which payment for the secondary service when purchased through the system is to be directed, a payment amount to be transferred to the provider for which payment for performing the secondary service is to be directed, and an indication of whether performance of the secondary service is optional or required in association with performance of the primary service. The items of information relevant to the bundled set of services included in the respective information record for an offered service within service offer database 114*h* that is indicated to be a primary service of a bundled set of services may further include, for example, an indication of whether the primary service is to be performed at an outside facility and, if the primary service is to be performed at an outside facility, items of information pertaining to each of one or more facilities that may be used to perform the primary service such as, for example, name, address, contact information, facility fee, and compensation information indicating a financial account that is used by the facility for receiving a facility fee.

Available products database 114*i* is used to maintain information records for various healthcare products (for example, prescription drugs and medical supplies) that can be offered by pharmacies registered with server system 110 (that is, pharmacies for which an account information record is maintained within pharmacy profile database 114*e*) for purchase by customer users registered with the system. In exemplary embodiments, the respective information records for the healthcare products that are maintained in available products database 114*i* and the information that populates the respective information record for each product can be created and maintained by a back-end administrator of server system 110. For each product for which an information record is created, various items of information relevant to the product, such as name(s), a list of dosage level options (for prescription drugs), size options (for certain medical supplies), and the like, a description of the product, an indication of whether a prescription is required to purchase the product, information for rendering a respective predefined fillable form for submitting prescription information for the product within a user interface, cost information (for example, average prices for the product for patients that are uninsured and/or have a high deductible insurance plan and a lowest price for purchasing the product that is offered for the service by pharmacies registered with server system 110), a product identifier that is used by application server 116 to uniquely identify the particular product, and any other suitable information may be included in the respective information record for the product that is maintained within available products database 114*i*.

Product offer database 114*j* is used to maintain information records for healthcare products that are being offered by pharmacies registered with the system for purchase by customer users registered with the system. In this regard, it should be noted that the same product may be separately offered by multiple different pharmacies registered with the system and, thus, product offer database 114*j* can include multiple information records for the same product that are each associated with a different provider. For each product offered by a pharmacy for which a respective information record is maintained within product offer database 114*j*, various items of information relevant to the product being offered, such as the unique product identifier for the information record within available products database 114*i* for the product, the unique pharmacy account identifier for the account information record within pharmacy profile database 114*e* of the pharmacy that is offering the product, a discounted price for purchasing the product from the identified pharmacy within marketplace system 100, a regular price for the product when the service is purchased outside of the system from the identified pharmacy, a payment amount to be transferred to the pharmacy that is offering the product, additional descriptive information that may be provided by the pharmacy offering the product, a product offer identifier that is used by application server 116 to uniquely identify the information record for the offering of the particular product by the pharmacy within the system, and any other suitable information may be included in the respective information record for the offered product that is maintained within product offer database 114*j*.

Transaction information database 114*k* is used to maintain information records for purchases that have been made via the system by registered customer users of healthcare services and products being offered by registered providers. For each purchase of a service or product that has been made using the system, various items of information relevant to the purchase may be included in the respective information record for the purchase that is maintained within transaction information database 114*k*. In general, the items of information relevant to each purchase that is included in the respective information record for the purchase that is maintained within transaction information database 114*k* can include, for example, the unique customer account identifier of the account information record for the purchasing customer within customer profile database 114*a*, the unique procedure offer identifier of the information record for a purchased service within service offer database 114*h* or the unique product offer identifier of the information record for a purchased product within product offer database 114*j*, a purchase date, and a unique transaction identifier that is used by application server 116 to uniquely identify the information record for the purchase of the service or product within the system. For each purchase of a service that has been made using the system, the items of information relevant to the purchase included in the respective information record for the purchase that is maintained within transaction information database 114*k* may further include the unique physician account identifier for the account information record within physician profile database 114*b* of the physician user that is designated as performing the purchased service in the information record for the purchased service within service offer database 114*h*, an indication of whether the purchase has been redeemed and, if the purchase has been redeemed, a redemption date.

Additionally, in exemplary embodiments, the information records for purchased services that are maintained within transaction information database 114*k* can include information records that include additional information for purchases and services that are offered by providers registered with the system as a bundled set of services. In this regard, the information record for each purchased bundled set of services that is maintained within transaction information database 114*k* may include an indication of a particular outside facility that has been selected for performing the primary service of the bundled set of services and, for each service of the bundled set of services that is included within the purchase (for example, each required secondary service or each optional secondary service selected by the customer user to be included within the purchase, as well as the primary service), the unique physician account identifier for the account information record within physician profile database 114*b* of the physician user that is designated as performing the service in the information record for the purchased service within service offer database 114*h*, an indication of whether the purchase has been redeemed with respect to that particular service, and, if the purchase has been redeemed with respect to that particular service, a redemption date for that particular service.

As discussed above, application server 116 can implement a user interface so that users of connected client systems 140 can access various services provided by the application server with relative ease by operating a corresponding client application 142. In exemplary embodiments, the user interface can be a web-based user interface, implemented as a web-based software application hosting a corresponding website that provides a number of web pages (that is, screens) to offer the services implemented by application server 116 to users. For example, a user can access the corresponding website using a web browser implemented within a client application 142 executing on a client system 142.

In exemplary embodiments, when any user, regardless of whether the user is registered with system 110 with any type of user account or a non-registered user, operates a client system 140 to access application server 116 (for example, by launching a native client application or by using a web browser to submit a URL that provides a network address for application server 116), the application server can be configured with a default setting that directs the user to a home page for the services grouped within customer portal 120, at which the user is presented with various options through a search interface to access functions provided by navigation and search service 124.

Figure 3A:
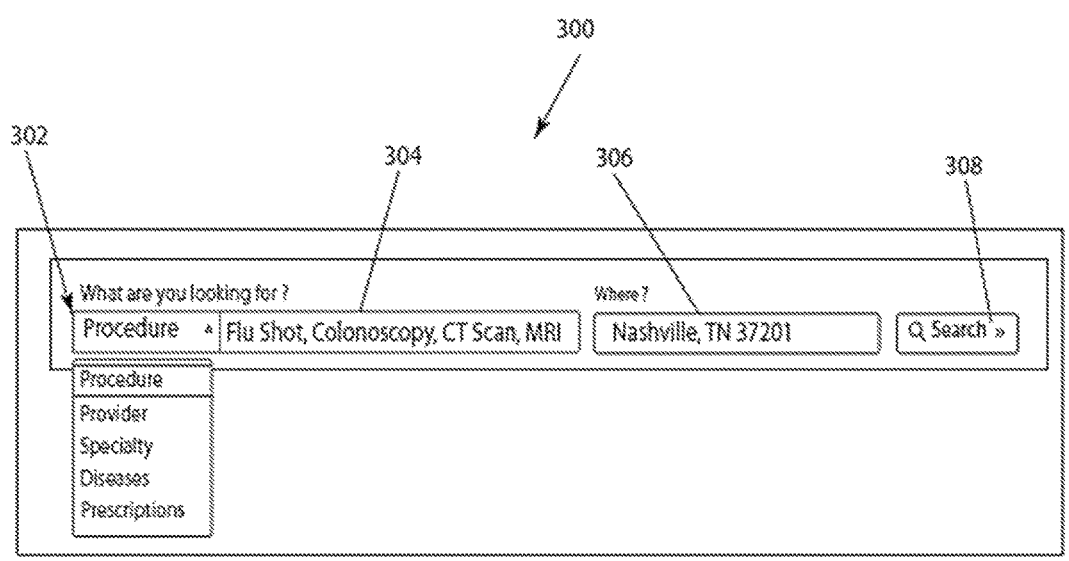

FIG. 3A is a screen shot illustrating an example of a graphical user interface provided by such a home page 300 for customer portal 120. In the illustrated example, the search interface provided at home page 300 can include a drop-down menu 302, a search entry field 304, a location entry field 306, and a search button 308. Drop-down menu 302 provides a set of selectable options that allow the user to search for particular procedures offered by provider users registered with the system, particular products offered by pharmacy users registered with the system, information on providers registered with the system, and information on health conditions that is maintained within system. In exemplary embodiments, navigation and search service 124 can be configured to use location information that may be gathered by any suitable location determining functionality implemented on the client system to provide a default location entry (for instance, city name and/or zip code) within location entry field 306. In such embodiments, navigation and search service 124 may be further configured to request permission from the user via the user interface to be able to access and utilize such location information for this purpose.

In one example, when the user selects the option within drop-down menu 302 to search for a particular service offered by provider users registered with the system, the user can then proceed to enter the name of the service within search entry field 304. In exemplary embodiments, navigation and search service 124 can be configured to, as the user enters the name of the service to be searched, identify and provide corresponding suggested entry completions in association with search entry field 304 (for instance, by comparing the entered characters with the various service names included in the respective information records for healthcare services that are maintained in available services database 114g). The user can then select one of the suggested entry completions at any point or continue to complete entry of the service name manually. In alternative exemplary embodiments, to allow a user to select a particular service to be included in search entry field 304, home page 100 may be configured to provide an additional drop-down menu in conjunction with a selection of the option within drop-down menu 302 to search for a particular service that allows a user to first select from a list of specialties, and, upon a selection of a particular specialty being made by the user, provides a list of services associated with the selected specialty (for example, based on information maintained in available services database 114g) from which the user can select the particular service to be included in search entry field 304. In conjunction with selecting the particular service, the user can also enter a city name and/or zip code or opt to utilize a default location entry within location entry field 306 to localize a search radius for providers offering the selected service for purchase via marketplace system 100.

Once the appropriate search information is entered, the user can then select the search button to direct navigation and search service 124 to conduct a search of local providers registered with server system 110 and offering the inputted healthcare service for purchase via marketplace system 100. Navigation and search service 124 can conduct such a location-based search by accessing, for example, service offer database 114h in conjunction with physician profile database 114b, practice group profile database 114c, hospital system profile database 114d, and/or any other suitable information and databases to which the application server has access to filter the information records included within available services database 114g for healthcare services that match the specified search criteria, and then present the results of the search to user within a search result listing page.

In exemplary embodiments, whenever navigation and search service 124 is directed to conduct a location-based search by a user (for example, for local providers offering the inputted healthcare service or, as discussed below, for local providers generally or for local pharmacy providers offering healthcare products), the navigation and search service can be configured to maintain the location specified within location entry field 306 for search within a data object for a session with application server 116 that is maintained for the user. As referred to herein, the term "session" can refer a series of transactions that can be performed sequentially by interacting with and navigating through various pages during a single, unbroken string of interactions. Such a session may end, for example, when the user terminates a native client application running on the client system and being operated by user, when the user terminates a web browser being used to access a web application provided by application server 116 or stops selecting or navigating through pages within the domain of the website provided by the application server and instead navigates to a web site at a different domain, or when the user logs out of a customer account being used to access services provided by the application server with respect to a particular customer account information record that is maintained within customer profile database 114a. In exemplary embodiments, the session data object for sessions with application server 116 that are presently being maintained for users can be stored and maintained locally to application server 116.

Figure 3B:
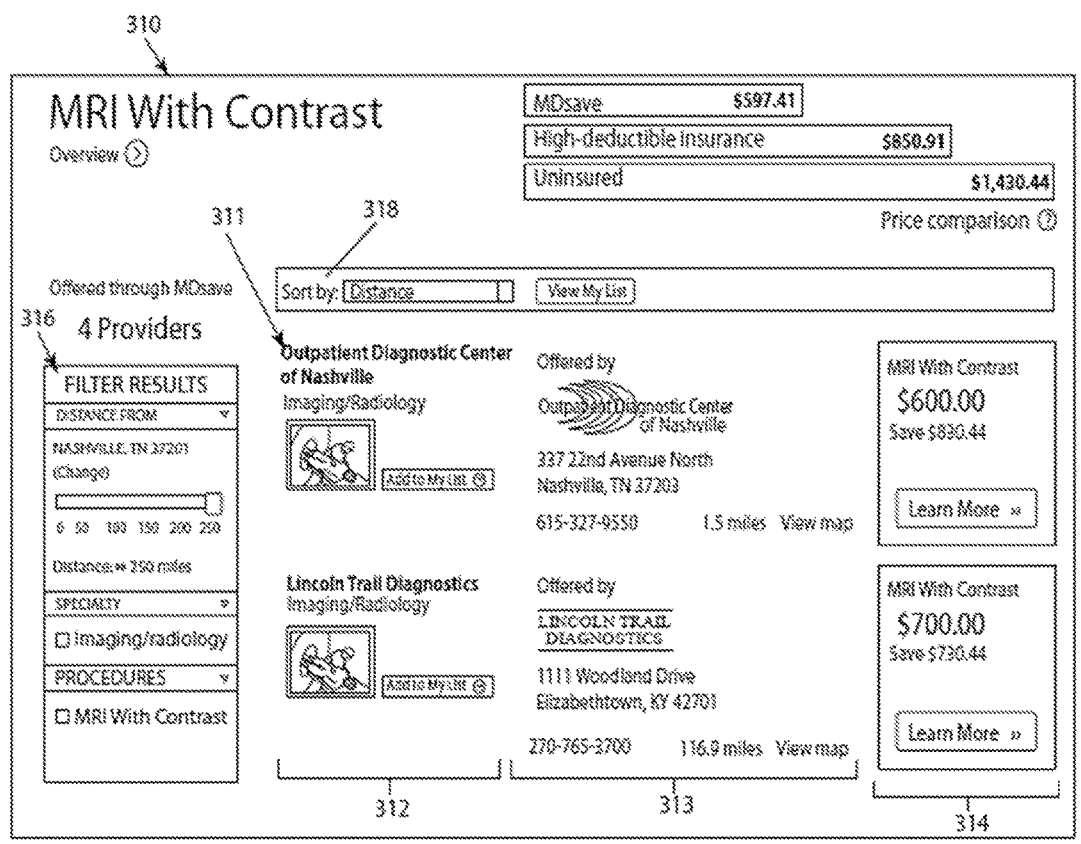

FIG. 3B is a screen shot illustrating an example of a GUI provided by a search result listing page 310 for customer portal 120 that presents a list of providers offering the service specified within search entry field 304 within a default search radius (for example, 50 miles) of the location specified within location entry field 306 returned in the search conducted by navigation and search service 124. In the illustrated example, search result listing page 310 includes a result listing section 311, a result filtering section 316, and a result sorting section 318. Result listing section 311 presents an entry for each offered service for which a respective information record is maintained within service offer database 114h that matches the specified search criteria. Result filtering section 316 provides various user interface controls for refining the results of the search presented within result listing section 311 by modifying the search criteria or inputting additional search criteria. In the illustrated example, result filtering section 316 includes a distance slide bar that is accessible to the user to increase or decrease the geographical search radius of searched providers offering the service specified within search entry field 302 and an option to refine the results according to one or more particular specialties of the physician that will perform the service. In this regard, navigation and search service 124 can be configured to, in response to a user accessing the user interface controls to modify the search criteria or input additional search criteria, conduct an updated search of the information records included within available services database 114g for healthcare services according to the newly-specified search criteria, and then update the entries for offered services within result listing section 311 according to the results returned in the updated search. Result sorting section 318 provides user interface controls that can be accessed by a user to direct navigation and search service 124 to order the list of entries for offered services within result listing section 311 according to a specified criteria (for example, according to the price for purchasing the offered service via server system 110 or the distance between the location of the offered service and the location specified within location entry field 306). In exemplary embodiments, such a search result listing page 310 can be implemented to present any other appropriate information relevant to the search criteria specified by the user, such as, for example, a graphic depicting the average cost information included in the information record for the service specified in the search criteria that is maintained in available services database 114g.

In the example screen shot depicted in FIG. 3B, each entry for an offered service listed in result listing section 311 includes a first portion 312 presenting information from the account information record within physician profile database 114b of the physician that will perform the service as specified in the information record for the offered service within service offer database 114h (for example, the physician's name, specialty, and profile picture), a second portion 313 presenting information from the account information record of the provider that is offering the service through the system (for example, provider name) and the location at which the offered service will be performed (for example, address and telephone number), and a third portion 314 presenting cost information for purchasing the offered service through application server 116 (for example, the discounted price for the service that is specified in the information record for the offered service within service offer database 114*h* and a cost savings difference between the discounted price and the regular price for the service when the service is purchased outside of the system from the provider as specified in the information record for the offered service within service offer database 114*h*), and an option to select to purchase the offered service listed in the entry (for example, via an "Add to Cart" button included within third portion 314). When a user selects the option to purchase an offered service listed in result listing section 311, navigation and search service 124 can be configured to update the session data object for the session with application server 116 that is presently being maintained for the user to include an indication that the user has selected the offered service for purchasing (for example, by including the procedure offer identifier that is maintained within service offer database 114*h* to uniquely identify the offering of the particular service by the provider). As will be described in greater detail below, upon selecting one or more services and/or products for purchase in association with a session with application server 116, the user will then have an option to navigate to a customer purchase page (for example, a "Check-Out" page) to proceed with purchasing the selected item(s) with respect to an account information record maintained within customer profile database 114*a* for a registered customer user.

In exemplary embodiments, result listing section 311 can be further implemented to present any other appropriate information relevant to the offered services included in the search results. Additionally, for each entry for an offered service listed in result listing section 311, first portion 312 can further include a hyperlink or other reference that is accessible by the user via the user interface to navigate to a physician profile page that presents information regarding the physician that will perform the offered service (an example of such a physician profile page will be described below with reference to FIG. 3D). Search result listing page 310 can be further implemented to include additional hyperlinks or other references to other relevant pages providing information that is relevant to the search criteria specified by the user, such as a reference to a healthcare service information page that presents information regarding the specified service (an example of such a healthcare service information page will be described below with reference to FIG. 3C).

Referring again to example home page 300 illustrated in FIG. 3A, in another example in which the user selects the option within drop-down menu 302 to search for a particular product offered by pharmacies registered with the system, the user can then proceed to enter the name of the particular product within search entry field 304. In exemplary embodiments, navigation and search service 124 can be configured to, as the user enters the name of the product to be searched, identify and provide corresponding suggested entry completions in association with search entry field 304 (for instance, by comparing the entered characters with the various product names included in the respective information records for healthcare products that are maintained in available product database 114*g*). The user can then select one of the suggested entry completions at any point or continue to complete entry of the product name manually. In exemplary embodiments, to allow a user to select a particular product to be included in search entry field 304, home page 100 may be configured to provide suitable user interface controls or a hyperlink or other reference that can be accessed by the user to present the user with an alphabetized list of product names from which the user can select the particular product to be included in search entry field 304. In this regard, navigation and search service 124 can be configured to provide separate alphabetized lists of product names for prescription drugs and medical supply products and allow the user to select the appropriate one of the lists to locate the particular product name desired.

Once the desired product name is entered by the user in search entry field 304, the user can then select the search button to direct navigation and search service 124 to initiate a search of pharmacies registered with server system 110 and offering the inputted healthcare product for purchase via marketplace system 100. If further information is required regarding the particular product entered by the user prior to conducting the search (for example, a particular dosage level and quantity for a prescription drug according to a prescription written for the user, a particular size option for a medical supply product, and the like), navigation and search service 124 can be configured to implement suitable user interface controls to allow the user to specify the additionally required information. For example, navigation and search service 124 can be configured to direct the user interface to a page at which the additionally required information can be specified by a user selection of the appropriate information from a list of selectable options. The information and options provided at such a page can be generated based on the respective information record for the particular healthcare product that is maintained in available products database 114*i* and may further include a presentation of various items of information relevant to the product for the user to review, such as a description of the product and an indication of whether a written prescription from a medical specialist is required to purchase the product.

Upon any additional required information being specified by user, navigation and search service 124 can then conduct such a search by accessing, for example, product offer database 114*j* in conjunction with pharmacy profile database and/or any other suitable information and databases to which application server 116 has access to filter the information records included within product offer database 114*j* for healthcare products that match the specified search criteria, and then present the results of the search to user within a product search result listing page that presents a list of pharmacies offering the product specified within search entry field 304. Such a product search result listing page can present an entry for each offered service for which a respective information record is maintained within product offer database 114*j* that matches the specified search criteria. The product search result listing page may also provide user interface controls that can be accessed by a user to direct navigation and search service 124 to order the list of entries for offered products within the page according to a specified criteria (for example, according to the price for purchasing the offered product via server system 110).

In exemplary embodiments, such a search result listing page 310 can be implemented to present any other appropriate information relevant to the search criteria specified by the user, such as, for example, a graphic depicting the average cost information included in the information record for the particular product specified in the search criteria that is maintained in available products database 114*j* (for prescription drug products, the average cost information can be provided for a default quantity of the prescription drug or, alternatively, based on a calculation performed by navigation and search service 124 for the quantity specified by the user using the average cost information for a default quantity as a reference). Each entry for an offered product listed in the product search result listing page can include portions presenting information from the account information record of the pharmacy that is offering the product through the system (for example, pharmacy name, address, and contact information), cost information for purchasing the offered product through marketplace system 100 (for example, the discounted price for the product that is specified in the information record for the offered product within product offer database 114j or, for prescription drugs, a price that is calculated based on the specified discounted price in relation to the quantity specified by the user) and a cost savings difference between the discounted price and the regular price for the product when the product is purchased outside of the system as specified in the information record for the offered product), and an option to select to purchase the offered product listed in the entry (for example, via an "Add to Cart" button). When a user selects the option to purchase an offered product listed in the product search result listing page, navigation and search service 124 can be configured to update the session data object for the session with application server 116 that is presently being maintained for the user to include an indication that the user has selected the offered product for purchasing (for example, by including the product offer identifier that is maintained within product offer database 114j to uniquely identify the offering of the particular product by the pharmacy) in association with any other required information (for example, in the case of a prescription drug, the quantity that is specified by the user and the price that is calculated based on the discounted price for the product that is specified in the information record for the offered product within product offer database 114j in relation to the quantity specified by the user). As noted above and described in greater detail below, upon selecting one or more services and/or products for purchase in association with a session with application server 116, the user will then have an option to navigate to a customer purchase page (for example, a "Check-Out" page) to proceed with purchasing the selected item(s) with respect to an account information record maintained within customer profile database 114a for a registered customer user.

In exemplary embodiments, the product search result listing page can be further implemented to present any other appropriate information relevant to the offered product included in the search results. For instance, the product search result listing page can be implemented to include additional hyperlinks or other references to other relevant pages providing information that is relevant to the search criteria specified by the user, such as a reference to a healthcare product information page that presents information regarding the specified product.

Referring again to example home page 300 illustrated in FIG. 3A, in another example in which the user selects the option within drop-down menu 302 to search for information on health conditions maintained within server system 110, the user can then proceed to enter the name of a particular health condition within search entry field 304. In exemplary embodiments, navigation and search service 124 can be configured to, as the user enters the name of the condition to be searched, identify and provide corresponding suggested entry completions in association with search entry field 304 (for instance, by comparing the entered characters with the various condition names included in the respective information records for conditions that are maintained in condition information database 114O. The user can then select one of the suggested entry completions at any point or continue to complete entry of the condition name manually. In exemplary embodiments, to allow a user to select a particular condition to be included in search entry field 304, home page 100 may be configured to provide suitable user interface controls or a hyperlink or other reference that can be accessed by the user to present the user with an alphabetized list of condition names from which the user can select the particular condition to be included in search entry field 304.

Once the desired condition is entered by the user in search entry field 304, the user can then select the search button to direct navigation and search service 124 to navigate the user interface to a condition information page for the specified condition. In this regard, navigation and search service 124 may be configured to require that the text entered in search entry field 304 correspond to a condition for which a corresponding information record is maintained in condition information database 114f. For example, upon the user selecting the search button, navigation and search service 124 can be configured to provide a list of suggested condition names that are determined to be similar to the text entered in search entry field 304 from which the user can select upon making a determination that the text entered in search entry field 304 does not more closely correspond to a particular condition for which a corresponding information record is maintained in condition information database 114f.

Upon the user selecting the search button with an appropriate condition specified in search entry field 304, navigation and search service 124 can render the information page for the specified condition in the user interface. The condition information page for a particular condition can be implemented to present a set of appropriate information relevant to condition based on the information that is maintained in the respective information record for the condition that is maintained in condition information database 114f such as, for example, name, description, causes, risk factors, symptoms, and common treatments. In exemplary embodiments, the condition information page for a particular condition can be implemented to provide a list of corresponding healthcare services that can be offered by providers registered with server system 110 in conjunction with a respective hyperlink (or other reference) for each corresponding service that is accessible by the user within the user interface to navigate to a healthcare service information page that presents information regarding the specified service.

Referring now to FIG. 3C, a screen shot illustrating an example of a GUI provided by a healthcare service information page 320 implemented by navigation and search service 124 for a particular healthcare service is provided. In the illustrated example, healthcare service information page 320 includes a procedure overview section 322, a cost comparison graphic 324, and a provider listing section 326. The information presented in procedure overview section 322 can be generated based on the procedure detail information included in the respective information record that is maintained for the particular service in available services database 114g. Likewise, information that is presented in cost comparison graphic 324 can be generated based on the average cost information included in the respective information record that is maintained for the particular service in available services database 114g (for example, to present a display of average prices the service for patients that are uninsured and/or have a high deductible insurance plan in comparison with an average price for purchasing the bundled set of services that is offered by providers registered with server system 110).

As noted above, for a particular healthcare service that is being offered as a bundled set of services, the cost information that is included in the respective information record for the primary service that is maintained within available services database 114g can include respective cost information for each of the primary service, the one or secondary services, and, if required, the use of an outside facility for the primary service individually. In this regard, the information that is presented in cost comparison graphic 324 for such a bundled set of services can be generated to present a display of the aggregate sum of the respective individual prices for each of the primary service, the one or secondary services, and, if required, the use of an outside facility for the primary service individually for patients that are uninsured and/or have a high deductible insurance plan in comparison with an average price for purchasing the bundled set of services that is offered by providers registered with server system 110. In this manner, the cost information for the entire bundled set of services, rather than simply for the primary service alone, can be made transparent to a user visiting the healthcare service information page for a particular healthcare service that is being offered as a bundled set of services. A healthcare service information page that is implemented by navigation and search service 124 for a particular healthcare service that is being offered as a bundled set of services may also present additional information relevant to the bundled set of services.

The information presented in provider listing section 326 can be generated in a manner similar to the information included in result listing section 311 of example search result listing page 310 depicted in FIG. 3B to present a list of providers offering the particular service within a default search radius (for example, 50 miles) of a location determined by navigation and search service 124. The particular location that is utilized for this purpose may be determined using, for example, a location that is stored within the session data object for the session with application server 116 that is presently being maintained for the user or location information that is gathered by any suitable location determining functionality implemented on the client system to provide a default location entry. In the present example, provider listing section 326 presents an entry for each offered service for which a respective information record is maintained within service offer database 114h that matches the particular service for which healthcare service information page 320 is generated and along with the determined location. Each entry for an offered service listed in provider listing section 326 presents information from the account information record within physician profile database 114b of the physician that will perform the service as specified in the information record for the offered service within service offer database 114h (for example, the physician's name and profile picture) and cost information for purchasing the offered service through application server 116 (for example, the discounted price for the service that is specified in the information record for the offered service within service offer database 114h). In the present example, provider listing section further includes a location entry field 327 that, in conjunction with a "submit" button 328, allows a user to specify a particular location (for example, a city name and/or zip code) and submit a request for navigation and search service 124 to conduct a search and update the information presented in provider listing section 326 to present a list of providers offering the particular service within the default search radius of the newly specified location. Navigation and search service 124 can also be configured to, in response to such a request, update the location that is maintained within the session data object for the session with application server 116 that is presently being maintained for the user.

In exemplary embodiments, provider listing section 326 can be further implemented to present any other appropriate information relevant to the offered services included in the search results. Additionally, each entry for an offered service listed in provider listing section 326 can further include a hyperlink or other reference that is accessible by the user via the user interface to navigate to a physician profile page that presents information regarding the physician that will perform the offered service specified in the entry. A screen shot illustrating an example of a GUI provided by a physician profile page 330 implemented by navigation and search service 124 for a particular physician user registered with server system 110 is provided in FIG. 3D.

In the illustrated example, physician profile page 330 includes a physician information section 332 and an offered procedures section 336. The information presented in physician information section 332 can be generated based on the information that is included in the respective account information record that is maintained for the particular physician user in physician profile database 114b and may include various items of information relevant to the physician, such as name, practice specialty, office location(s) and hours, a profile picture, contact information, biographical information (such as awards, honors, publications, patient testimonials, and other information that may be of interest to prospective customers accessing the system), URLs or references to websites and social media profiles, and group practice and hospital affiliation(s).

Figure 3D:

In exemplary embodiments, as further illustrated in FIG. 3D, physician information section 332 can further include additional user interface elements such as a "Leave a review" button 333, a "Request an appointment" button 334, and a map element 335 depicting a mapped location of an office location included within respective account information record that is maintained for the particular physician user in physician profile database 114b (which navigation and search service 124 may be configured to generate by remotely accessing a third-party mapping service). In response to a user selecting "Leave a review" button 333, navigation and search service 124 can be configured to implement suitable user interface controls for allowing the user to post or submit a review of the particular physician to server system 110. In response to receiving such a review, navigation and search service 124 can be configured to, for example, include information pertaining to the review within the respective account information record that is maintained for the particular physician user in physician profile database 114b or send an electronic message to the physician user pertaining to the review, for example, by way of email utilizing the contact information specified in the respective account information record for the physician.

In response to a user selecting "Request an appointment" button 334, navigation and search service 124 can be configured to implement suitable user interface controls for allowing the user to submit a request for scheduling an appointment to the particular physician user (for example, by sending a notification to the physician user by utilizing the contact information specified in the respective account information record for the physician that includes contact information for the user). Navigation and search service 124 may also be configured to implement suitable user interface controls for allowing the user to schedule an appointment with the particular physician user. Navigation and search service 124 may provide this functionality by, for example, accessing a service with which the particular physician user is associated, which may be a service offered by application server 116 or offered by a third-party service provider.

In the present example, as illustrated in FIG. 3D, the information presented in offered procedures section 336 of physician profile page 330 can include a listing of healthcare services offered by the particular physician for purchase through marketplace system 100. More specifically, offered procedures section 336 presents an entry for each offered service for which a respective information record is maintained within service offer database 114*h* that identifies, as the physician that performs the service, the unique physician account identifier for the account information record within physician profile database 114*b* of the particular physician. In the example screen shot depicted in FIG. 3D, each entry for an offered service listed in offered procedures section 336, which may be generated based on the respective information record that is maintained within service offer database 114*h* for the offered service and the respective information record for the service that is maintained in available services database 114*g*, includes a service name (which may be provided in conjunction with in conjunction with a hyperlink or other reference that is accessible by the user within the user interface to navigate to the healthcare service information page that presents information regarding the named service, as described above with reference to FIG. 3C), average cost information for the service, and the discounted price for purchasing the offered service that is specified in the information record for the offered service within service offer database 114*h*. In exemplary embodiments, each entry for an offered service listed in offered procedures section 336 can be implemented to further include a user interface element that is accessible by the user to direct navigation and search service 124 to present additional information regarding the offered service listed in the entry along with an option to select to purchase the offered service (for example, via an "Add to Cart" button) within the user interface. Upon a user selecting such an option to purchase an offered service, navigation and search service 124 can be configured to update the session data object for the session with application server 116 that is presently being maintained for the user to include an indication that the user has selected the offered service for purchasing.

Referring again to example home page 300 illustrated in FIG. 3A, in another example in which the user selects the option within drop-down menu 302 to search for providers registered with the system, the user can then proceed to enter the name of a particular provider within search entry field 304. In exemplary embodiments, navigation and search service 124 can be configured to, as the user enters the name of a provider to be searched, identify and provide corresponding suggested entry completions in association with search entry field 304 (for instance, by comparing the entered characters with the various provider names included in the respective information records for various providers that are maintained in physician profile database 114*b*, practice group profile database 114*c*, and hospital system profile database 114*d*. The user can then select one of the suggested entry completions at any point or continue to complete entry of the service name manually.

Once the desired provider name is entered by the user in search entry field 304, the user can then select the search button to direct navigation and search service 124 to navigate the user interface to provider profile page for the specified provider. In this regard, navigation and search service 124 may be configured to require that the text entered in search entry field 304 correspond to a provider for which a corresponding account information record is in physician profile database 114*b*, practice group profile database 114*c*, and hospital system profile database 114*d*. For example, upon the user selecting the search button, navigation and search service 124 can be configured to provide a list of suggested provider names that are determined to be similar to the text entered in search entry field 304 from which the user can select upon making a determination that the text entered in search entry field 304 does not more closely correspond to a particular provider for which a corresponding account information record is maintained by database server 112.

Upon the user selecting the search button with an appropriate provider name specified in search entry field 304, navigation and search service 124 can render the provider profile page for the specified provider name in the user interface. For example, if the provider profile name corresponds to a physician user registered with server system 110, navigation and search service 124 can render the respective physician profile page (as discussed above with reference to FIG. 3D) for the corresponding physician in the user interface. Alternatively, if the provider profile name corresponds to a practice group registered with server system 110, navigation and search service 124 can render a respective practice group profile page for the corresponding practice group in the user interface, which may include information generated based on the respective account information record that is maintained for the particular practice group in practice group profile database 114*c* and may include various items of information relevant to the practice group, such as practice group name, location and hours, contact information, URLs or references to websites and social media profiles for the practice group, and a list of affiliated physicians. The respective practice group profile page for the corresponding practice group may further include a listing of healthcare services offered by the particular practice group for purchase through marketplace system 100 that presents an entry for each offered service for which a respective information record is maintained within service offer database 114*h* that identifies, as the provider that is offering the service through the system, the unique account identifier for the account information record within practice group profile database 114*c* of the particular practice group. Likewise, if the provider profile name corresponds to a hospital system registered with server system 110, navigation and search service 124 can the render a respective hospital system profile page for the corresponding hospital system in the user interface, which may include information generated based on the respective account information record that is maintained for the particular hospital system in hospital system profile database 114*d* and may include various items of information relevant to the hospital system, such as hospital system name, a list of practice group and physician affiliation(s), facilities that are used for particular procedures performed by physicians affiliated with the hospital system, and URLs or references to websites and social media profiles for the hospital system. The respective hospital system profile page for the corresponding hospital system may further include a listing of healthcare services offered by the particular hospital system for purchase through marketplace system 100 that presents an entry for each offered service for which a respective information record is maintained within service offer database 114*h* that identifies, as the provider that is offering the service through the system, the unique account identifier for the account information record within hospital system profile database 114*d* of the particular hospital system.

Alternatively, when a user selects the option within drop-down menu 302 to search for providers registered with the system, the user, rather than searching for a specific provider by name, can opt to leave search entry field 304 blank and, instead, conduct a search for local providers by entering a city name and/or zip code or opt to utilize a default location entry within location entry field 306 to localize a search radius. Once the appropriate search information is entered, the user can then select the search button to direct navigation and search service 124 to conduct a search of local providers registered with server system 110. Navigation and search service 124 can conduct such a location-based search by accessing physician profile database 114b, practice group profile database 114c, and hospital system profile database 114d to filter the account information records for providers maintained by database server 112 for local providers, and then present the results of the search to user within a provider search result listing page. Such a provider search result listing page can present a list of registered providers within a default search radius (for example, 50 miles) of the location specified within location entry field 306 returned in the search conducted by navigation and search service 124 that includes an entry for each registered provider for which a respective account information record maintained by database server 112 indicates a location for the provider that is within the default search radius. In exemplary embodiments, such a provider search result listing page can also provide various user interface controls for refining the results of the search presented by modifying the search radius or inputting additional search criteria (in a manner similar to that described above with reference to FIG. 3B for search result listing page 310). Each entry provided within the list of registered providers returned in the provider search result listing page can further include a hyperlink or other reference within the user interface that is accessible by the user to direct navigation and search service 124 to render the provider profile page for the corresponding provider.

Similarly, and referring again to FIG. 3A, when a user selects the option within drop-down menu 302 to conduct a search with respect to a particular specialty, the user can then proceed to enter the name of a particular practice specialty within search entry field 304. In exemplary embodiments, navigation and search service 124 can be configured to provide a drop-down within search entry field 304 that allows the user to select one of a plurality of specialties recognized by server system 110. Once the desired specialty is entered by the user in search entry field 304, the user can then conduct a search for local providers having the specified practice specialty by entering a city name and/or zip code or opt to utilize a default location entry within location entry field 306 to localize a search radius. Once the appropriate search information is entered, the user can then select the search button to direct navigation and search service 124 to conduct a search of local providers registered with server system 110. Navigation and search service 124 can conduct such a location-based search by accessing physician profile database 114b and practice group profile database 114c to filter the account information records for providers maintained by database server 112 for local providers having the specified practice specialty, and then present the results of the search to user within a provider search result listing page, which may be presented in a manner similar to the provider search result listing page described above with reference to the situation in which a user selects the option within drop-down menu 302 to search for providers registered with the system.

As discussed above, in exemplary embodiments, when a user operating a client system selects an option that is presented within a user interface implemented by application server 116 within the corresponding client application executing on the client system to purchase an offered healthcare service or an offered healthcare product, navigation and search service 124 can be configured to update a session data object for the session with application server 116 that is presently being maintained for the user to include an indication that the user has selected the offered service or product for purchasing. As will be described in greater detail below, in exemplary embodiments, upon selecting one or more services and/or products for purchase in association with a session with application server 116, the user will have an option to navigate to a customer purchase page (for example, a "Check-Out" page) to proceed with purchasing the selected item(s) with respect to an account information record maintained within customer profile database 114a for a registered customer user.

In such embodiments, a customer user is required to first register with server system 110 and thereby establish a respective account information record within customer profile database 114a to be able to make prepaid purchases of healthcare services and products via marketplace system 100. In exemplary embodiments, a user operating a client system to access application server 116 via a corresponding client application executing on the client system may be provided with a user interface element within the user interface implemented by application server 116 that is accessible by the user to initiate a registration with server system 110. Such a user interface element may be, for example, provided as a "Create an account" button included within the user interface of any page implemented by navigation and search service 124 and rendered at the client application, and navigation and search service 124 may be configured to, in response a user accessing the user interface element, provide further user interface controls for allowing the user to specify a type of user account that the user intends to register with server system 110.

Upon the user indicating an intention to register as a customer user, the user will be able to initiate a registration session with account management service 122 to register with a customer account with server system 110. Account management service 122 may be configured, for example, to implement a user interface that includes a series of pages with user interface controls accessible by the user to guide the user through the account registration process and prompt the user to input various types of information to be maintained by database server 112 within a respective account information record that is established for the user within customer profile database 114a such as, for example, name, address or location information, contact information (such as an email address and/or a telephone number), billing information for purchases (such as bank account information, credit card information, or information specifying any other funding source to use for purchases made by the user), and any other suitable identifying or descriptive information. Account management service 122 can be configured to access database server 112 to create the respective account information record for the user within customer profile database 114a based on the information input by the user during the registration process. Account management service 122 can be further configured to generate the unique customer account identifier for the created account information record, which may be used, for example, to index and reference the created account information record within database server 112. The created account information record can also be identified with a unique user name and protected by a password, which can be used by the user to log into the associated customer account when accessing application server 116.

In exemplary embodiments, the user interface implemented by account management service 122 may be further configured to provide user interface controls for requesting authorization for payment of a predetermined fee to gain access to the ability to make prepaid purchases of healthcare services and products offered within marketplace system 100. Such a fee may be, for example, a one-time charge or a periodic charge (such as a monthly, biannual, or annual fee). In conjunction with such a payment authorization request, the user interface controls provided by account management service 122 may also be implemented to prompt the user to input the payment information specifying the funding source the user will use for payment of the predetermined access fee. The payment information input by the user may be an instruction to use the billing information included within the respective account information record established for the user within customer profile database 114a or submission of alternative payment information such as, for example, bank account information, credit or debit card information, or other electronic payment information (such as information for utilizing an account the user has with PayPal or any another entity facilitating payments and money transfers to be made through the Internet), which may be for an account maintained for the user or an account maintained for another person or entity that the user is authorized to utilize for this purpose. Account management service 122 can be configured to, upon the authorization and appropriate payment information being provided by the user, access a corresponding third-party payment servicing system and utilize the payment information to direct the payment servicing system to transfer the amount for the payment authorized by the user from the account servicer of the user to a financial account maintained by the providers of marketplace system 100. In this regard, the respective account information record established for the user within customer profile database 114a can further include an account status that is managed by account management service 122 for the user indicating whether the user is presently provided with the ability to make prepaid purchases of healthcare services and products offered within marketplace system 100.

Upon a user registering a customer account with server system 110 to establish an account information record within customer profile database 114a and logging into his or her customer account (for example, by accessing a login user interface element or a login screen within the user interface implemented by customer portal 120 to provide the user name and password associated with the account), the user then proceeds with purchasing any offered service or product for which the session data object for the session with application server 116 that is being maintained for the user includes an indication that the user has selected for purchasing. For example, upon the user selecting an option within the user interface implemented by navigation and search services 124 to navigate to a customer purchase page and initiate a purchasing session with purchasing service 126 to purchase one or more of the offered items indicated as having been selected by the user in the session data object in association with the registered customer account for the user.

Purchasing service 126 may be configured, for example, to implement a user interface that includes one or more pages with user interface controls accessible by the user to guide the user through the purchasing process and prompt the user to input and make selections of various types of information. For example, a purchase information section may be included within a payment page provided within the user interface that includes a respective entry for each offered item indicated as having been selected by the user in the session data object. For each offered product for which a respective entry is included in the purchase information section, the entry may include, for example, information retrieved from pharmacy profile database 114e, available products database 114i, product offer database 114j, and the session data object such as pharmacy name, product name along with any dosage level, form of the medicine, and quantity for a prescription drug or size option for a medical supply, and an indication of whether a prescription is required to purchase the product. Each entry for an offered product that is included in the purchase information section may further include user interface controls accessible by the user to remove the offered product from the purchase information section (and correspondingly direct purchasing service 126 to remove the indication the offered product as having been selected in the session data object) and/or to adjust a product quantity to be purchased by the user, and a price for purchasing the offered product that is calculated based on the product quantity specified by the user and the discounted price for the product that is specified in the information record for the offered product within product offer database 114j or, for prescription drugs, a price that is calculated based on the specified discounted price in relation to the quantity specified by the user).

For each offered service for which a respective entry is included in the purchase information section, the entry may include, for example, information retrieved from physician profile database 114b, available services database 114g, service offer database 114h, and the session data object such as the name of the physician that will perform the service, a service name, and an indication of whether the service is being offered as a primary service of a bundled set of services. Each entry for an offered service that is included in the purchase information section may further include user interface controls accessible by the user to remove the offered service from the purchase information section (and correspondingly direct purchasing service 126 to remove the indication the offered service as having been selected in the session data object) and/or to adjust a service quantity to be purchased by the user, and a price for purchasing the offered service that is calculated based on the service quantity specified by the user and the discounted price for the service that is specified in the information record for the offered service within service offer database 114h in relation to the quantity specified by the user.

In addition, for each entry for an offered service included in the purchase information section that is being offered as a primary service of a bundled set of services, the entry may further include user interface controls accessible by the user to present additional information about the bundled set of services and make additional selections regarding the offered service. The additional information may include, for example, information retrieved from physician profile database 114b, available services database 114g, and service offer database 114h, such as the name of physician that will perform each secondary service, a service name for each secondary service, an indication of whether each secondary service is required or optional, and an indication of whether the primary service is required to be performed at an outside facility. In association with each secondary service for which an indication that the secondary service is optional is presented, the additional information may further include the discounted price for the secondary service that is specified in the information record for the offered service within service offer database 114h, and an associated user interface control may be provided that allows the user to select whether to purchase the optional secondary service in association with the offered service. In association with an indication that the primary service is required to be performed at an outside facility, the additional information may further include name and location information for each facility for which information is specified in the information record for the offered service within service offer database 114h, and, if information is specified for more than one facility in the information record for the offered service, the facility fee for each specified facility may be presented in association with a user interface control that is provided to allow the user to select one of the facilities at which to have the primary service performed. Purchasing service 126 can be configured to, based on any optional secondary service and facility selections that are made by the user with respect to an entry for an offered service included in the purchase information section that is being offered as a primary service of a bundled set of services, recalculate and update the price for purchasing the offered service that is presented in the entry for the offered service. In exemplary embodiments, the default initial settings for any optional secondary service and multiple facility selections for a service being offered as a primary service of a bundled set of services and, thereby, the default initial price for purchasing the offered service that is presented in the entry for the offered service, may be based on a selection to purchase each optional secondary service and a selection of the facility having the lowest facility fee.

The purchase information section included within the user interface implemented for the payment page may further include a total price for the purchase that is equal to a sum of the respective price for purchasing the corresponding offered item included for each entry included in the purchasing information section. In exemplary embodiments, purchasing service 126 may be configured to adjust the total price based on any applicable state taxes or any discount codes submitted by the user. In this regard, purchasing service 126 may be further implemented to provide a user interface element allowing a user to submit any application discount codes to application server 116.

Upon the user reviewing the information provided in the purchase information section and making any desired modifications and selections via the user interface controls implemented within the payment page, the user may then proceed to access further user interface controls implemented within a payment section of the payment page to make a prepaid purchase of the one or more offered items for which respective entries are included in the purchase information section in a single transaction with purchasing service 126 by submitting customer purchase information specifying a funding source to use for purchasing the selected service offer and providing an authorization for server system 110 to issue a request to the funding source for funds in the amount of the total price for the purchase listed in the purchase information section. For this purpose, the user interface controls implemented within a payment section may include a button that is accessible by the user to provide authorization for the request to be issued to the specified funding source (for example, a "Submit" or "Purchase" button) along suitable user interface elements accessible by the user to input the purchase information specifying the funding source to use for the purchase. The purchase information input by the user may be an instruction to use the billing information included within the respective account information record for the customer account of the user within customer profile database 114a or submission of alternative purchase information such as, for example, bank account information, credit or debit card information, or other electronic payment information (such as information for utilizing an account the user has with PayPal or any another entity facilitating payments and money transfers to be made through the Internet). The purchase information may, for example, specify an account maintained for the user, an account maintained for another person or entity that the user is authorized to utilize for this purpose, or an entity that has arranged to be invoiced and provide reimbursement for purchases of healthcare services and products made by the user within marketplace system 100.

As described in greater detail below, upon the authorization and appropriate customer purchase information being provided by the user, for each offered item included within the purchase, the manner in which the purchase by the user is processed by purchasing service 126, as well as any further operations need to be performed by the user, may vary depending on whether the offered item is a service or product, whether a prescription is required to purchase an offered product, and whether an offered service is offered as a primary service of a bundled set of services. As also described below, the manner in which the purchase is processed by purchasing service 126 may also depend on the particular type of customer purchase information provided by the user.

More particularly, for processing payment for each offered product for which a prescription is not required for the purchase, purchasing service 126 may be configured to utilize the customer purchase information provided by the user to issue a request for the portion of the payment amount authorized by the user that is allocated for the offered product to the funding source specified in the purchase information. For example, for situations in which the purchase information specifies an entity that has agreed to be invoiced and provide reimbursement for purchases of healthcare services and products made by the user within marketplace system 100 as the funding source to use, purchasing service 126 may issue the request in the form of an invoice that is generated to be submitted to the funding source. In this example, purchasing service 126 may be further configured to electronically transmit the generated invoice to the specified funding source for reimbursement (for instance, via email to an email account maintained for this purpose by the specified funding source or to a third-party servicing system that is maintained on behalf of or by the funding source for receiving invoices of this type) or, alternatively, the generated invoice may be made available for an administrator of server system 110 to access and manually submit to the funding source for reimbursement. The information regarding how such an invoice is to be submitted to the funding source may be specified in conjunction with the purchase information provided by the user or, alternatively, may be maintained within server system 110 based on a pre-established agreement between the providers of marketplace system 100 and the funding source for this purpose. Purchasing service 126 can be further configured to credit or otherwise direct a disbursement of funds to be made to the financial account specified by the compensation information included in the account information record within pharmacy profile database 114e of the pharmacy that is offering the product with the corresponding payment amount that is specified to be transferred to the pharmacy indicated by the respective information record in product offer database 114j for the offered product. Upon receiving reimbursement for the invoiced amount being receiving from the funding source, a financial account maintained by the providers of marketplace system 100 can be credited with any negotiated or contracted commission fee for offering the product for purchase via the system (which may be, for example, a fixed percentage of the payment amount and/or a flat fee).

In another example, for situations in which the customer purchase information specifies an account maintained for the user or an account maintained for another person or entity that the user is authorized to utilize for this purpose, purchasing service 126 may be configured to access a corresponding third-party payment servicing system provided by or on behalf of the specified funding source and utilize the customer purchase information to issue a request directing the payment servicing system to transfer the portion of the payment amount authorized by the user that is allocated for the offered product from a corresponding financial account, credit or otherwise direct a disbursement of funds to be made to the financial account specified by the compensation information included in the account information record within pharmacy profile database 114e of the pharmacy that is offering the product with the corresponding payment amount that is specified to be transferred to the pharmacy in the respective information record in product offer database 114j for the offered product, and credit a financial account maintained by the providers of marketplace system 100 with any negotiated or contracted commission fee for offering the product for purchase via the system (which may be, for example, a fixed percentage of the payment amount and/or a flat fee).

Purchasing server 126 can be configured to, upon processing the payment for the purchase of the offered product, navigate the user interface to a purchase confirmation page and send an electronic confirmation message to the customer user and an electronic notification to the pharmacy administrator, for example, by way of email utilizing the contact information specified in the respective account information records for the customer and the pharmacy. Purchasing server 126 can be also be configured to generate a respective information record for the completed purchase with corresponding information within transaction information database 114k.

It should be noted that while the additional examples provided below describing the various manners in which payment may be processed by purchasing service 126 for different types of healthcare products and services are described in terms of circumstances in which the customer purchase information specifies an account maintained for the user or an account maintained for another person or entity that the user is authorized to utilize for this purpose, the payment processing that is performed in these examples should not considered to be limited to these circumstances and may also be performed, for instance, for circumstances in which the customer purchase information specifies an entity that has agreed to be invoiced and provide reimbursement for purchases of healthcare services and products made by the user within marketplace system 100 in a manner similar to that described above in relation to payment processing for offered products for which a prescription is not required for the purchase.

For processing payment for each offered product for which a prescription is required for the purchase, purchasing service 126 may be configured to, upon the user accessing the user interface on the payment page to provide authorization for payment, navigate the user interface to a prescription submission page prior to processing the payment for the offered prescription product. Prescription submission page can be implemented by purchasing service 126 to provide user interface controls for allowing the user to submit the required prescription information for purchasing the offered product. For example, prescription submission page may be implemented to provide a drop-down menu accessible by the user to select from a plurality of options for submitting the required prescription information. The plurality of options may include, for example, emailing an image of a prescription document to an email address for an account maintained in association with server system 110 for such a purpose, faxing a copy of a prescription document to a fax number utilized in association with server system 110 for such a purpose, uploading a copy of a prescription document to application server 116, and complete information fields of a respective predefined fillable form for generating a prescription document for the particular product within the user interface. If the user selects either the option to email an image of a prescription document or the option to fax a copy of the prescription document, prescription submission page can be implemented to present a display of instructions for the user to follow to submit the prescription document according to the selected option. If the user selects the option to uploading a copy of a prescription document, prescription submission page can be implemented to provide suitable user interface controls for allowing the user to perform this operation.

If the user selects the option to complete a respective predefined fillable form for generating a prescription document, purchasing system 126 can be configured access the information for rendering such a respective predefined fillable form that is maintained within available products database 114i for the corresponding product and render the form within the user interface. Such a form may include a number of fields for receiving various pieces of information concerning the user (such as name, address, and other relevant information), the prescription product (such as name, dosage, form of the medicine, quantity, a recommended frequency for administering the product or other instructions, and refill information for a continuing prescription), and the medical specialist that prescribed the product (such as name, practice group, a phone number or other preferred contact information, and a date on the product was prescribed) for the user as input. In exemplary embodiments, purchasing system 126 may be configured to automatically populate certain fields (for example, fields for receiving information concerning the user may be automatically populated based on information included in the respective account information records that is maintained for the user within customer profile database 114a), which the information for other fields can be manually input by the user via the user interface. Upon the appropriate fields of the fillable form being suitably populated, the user can select user interface element to submit the form to purchasing service 126, which can be configured to then generate a prescription document based on the information submitted.

Upon the prescription document being received from the user or generated based on information provided by the user, the prescription document can be released to the pharmacy specified for the offered product within product offer database 114j (which may be performed manually by an administrator for marketplace system 100, such as by fax or postal mail, or automatically by server system 110 by electronic transmission, such as within an email message to the pharmacy, according to contact information specified in the account information record for the pharmacy maintain within pharmacy profile database 114e). Upon receiving the prescription document, the pharmacy can perform a verification of the prescription document, for example, by contacting the medical specialist listed as having prescribed the product.

While awaiting verification of the prescription document, purchasing service 126 may be configured to utilize the purchase information provided by the user to issue a request for the portion of the payment amount authorized by the user that is allocated for the offered product to the funding source specified in the purchase information. For example, purchasing service 126 may be configured to access a corresponding third-party payment servicing system provided by or on behalf of the specified funding source and utilize the purchase information to issue a request directing the account servicer for a corresponding financial account to place a hold on funds for the portion of the payment amount authorized by the user that is allocated for the offered product. Upon a notification of verification of the prescription document being received from the pharmacy, purchasing service can be configured to access the corresponding third-party payment servicing system and utilize the purchase information specified by the user to direct the account servicer for the corresponding financial account to release the hold and direct the payment servicing system to transfer the portion of the payment amount authorized by the user that is allocated for the offered product from the corresponding financial account, credit or otherwise direct a disbursement of funds to be made to the financial account specified by the compensation information included in the account information record within pharmacy profile database 114e of the pharmacy with the corresponding payment amount that is specified to be transferred to the pharmacy in the respective information record in product offer database 114j for the offered product, and credit a financial account maintained by the providers of marketplace system 100 with any negotiated or contracted commission fee for offering the product for purchase via the system. Purchasing server 126 can be configured to, upon processing the payment for the purchase of the offered product, navigate the user interface to a purchase confirmation page and send an electronic confirmation message to the customer user and an electronic notification to the pharmacy administrator, for example, by way of email utilizing the contact information specified in the respective account information records for the customer and the pharmacy. Purchasing server 126 can be also be configured to generate a respective information record for the completed purchase with corresponding information within transaction information database 114k.

For processing payment for each offered service that is not being offered in conjunction with a bundled set of services, purchasing service 126 may be configured to utilize the purchase information provided by the user to issue a request for the portion of the payment amount authorized by the user that is allocated for the offered service to the funding source specified in the purchase information. For example, purchasing service 126 may be configured to access a corresponding third-party payment servicing system provided by or on behalf of the specified funding source and utilize the purchase information to issue a request directing the payment servicing system to transfer the portion of the payment amount authorized by the user that is allocated for the offered service from the account servicer of a corresponding financial account to a financial account maintained by the providers of marketplace system 100, at which point the financial account is credited with any negotiated or contracted commission fee for handling the purchase and holds the payment amount to be transferred to the provider for which payment for the service is to be directed (as specified in service offer database 114h) until an indication is received that the purchased service has been performed by the physician that is specified in service offer database 114h for performing the service (as described in greater detail below).

Purchasing server 126 can be configured to, upon processing the payment for the purchase of the offered service, navigate the user interface to a purchase confirmation page and send an electronic confirmation message to the customer user and electronic notifications to the physician user that will be performing the service and the provider user for the offered service (as specified according to the information record for the offered service within service offer database 114h), for example, by way of email utilizing the contact information specified in the respective account information records for the customer, the physician, and the provider for the offered service. Purchasing server 126 can be also be configured to generate a respective information record for the completed purchase with corresponding information within transaction information database 114k, which initially indicates that the purchase has not yet been redeemed.

Figure 4A:
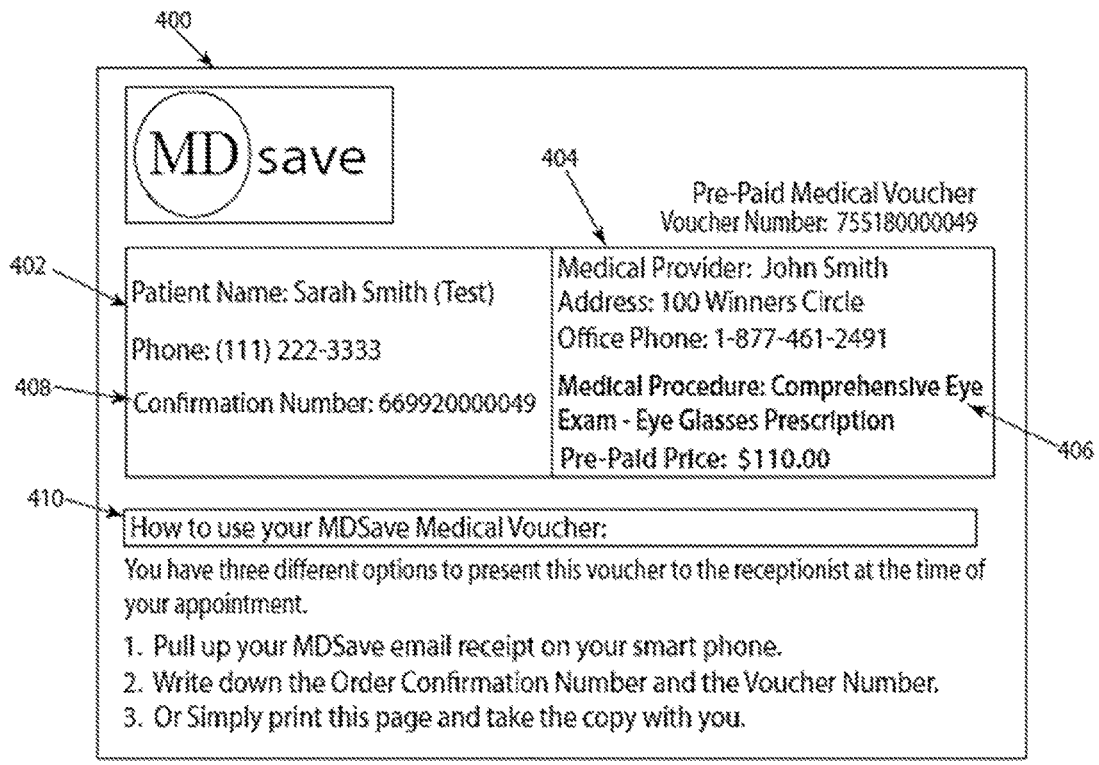
FIG. 4A is an illustration of an example voucher that may be generated within a user interface by functions provided within a customer portal for a purchased service in accordance with exemplary embodiments of the present invention.

Purchasing server 126 can also be configured to, upon processing the payment for the purchase of the offered service, generate a voucher for the customer user within the user interface for the purchased service that can be utilized by the customer user to redeem the purchase and receive the service from the physician specified for the offered service (the providers of marketplace system 100 can have pre-arranged agreements with providers registered with the system that the providers will agree to honor such vouchers generated by purchasing server 126 for purchased services). An example of such a voucher is illustrated in FIG. 4A. As depicted in the example, example voucher 400 can be generated to include identifying information for the customer user 402, identifying and contact information for the physician specified for the offered service 404, a description of the purchased service 406, a confirmation number 408 for the purchase, which may be generated by purchasing server 126 based on the unique transaction identifier that is included in the respective information record for the purchase that is maintained within transaction information database 114k, and instructions for redeeming the voucher 410. The confirmation number may also be provided in the electronic confirmation message to the customer user and electronic notifications to the physician user that will be performing the service and the provider user for the offered service sent by purchasing system 126 to the customer user. The voucher can be presented to the user within the user interface, for example, as printable and/or machine readable form.

Similarly, for processing payment for each offered service that is being offered as a primary service in conjunction with a bundled set of services, purchasing service 126 may be configured to utilize the purchase information provided by the user to issue a request for the portion of the payment amount authorized by the user that is allocated for the offered service to the funding source specified in the purchase information. For example, purchasing service 126 may be configured to access a corresponding third-party payment servicing system provided by or on behalf of the specified funding source and utilize the purchase information to issue a request directing the payment servicing system to transfer the portion of the payment amount authorized by the user that is allocated for the offered service from the account servicer of a corresponding financial account to a financial account maintained by the providers of marketplace system 100, at which point the financial account is credited with any negotiated or contracted commission fee for handling the purchase and holds the remainder of the payment amount portion. In contrast to the processing performed by purchasing service 126 for offered services that are not being offered in conjunction with a bundled set of services, however, a respective sub-portion of the payment amount for the offered service is held separately with respect to the primary service, each secondary service, and any facility specified for the purchased offered service (according to the payment amount specified to be transferred to the respective provider or facility for which payment for the service is to be directed for each particular aspect of the bundled set of services as specified in service offer database 114*h*), and each sub-portion is held until an indication is received that the corresponding service has been performed by the physician that is specified in service offer database 114*h* for performing the procedure or the corresponding facility has been used with respect to the primary service (as described in greater detail below).

Purchasing server 126 can be configured to, upon processing the payment for the purchase of the offered service that is being offered as a primary service in conjunction with a bundled set of services, navigate the user interface to a purchase confirmation page and send an electronic confirmation message to the customer user and electronic notifications to the each physician that will perform a service of the bundled set of services and the provider user for the offered service (as specified according to the information record for the offered service within service offer database 114*h*), for example, by way of email utilizing the contact information specified in the respective account information records for the customer, the physicians, and the provider for the offered service. Purchasing server 126 can be also be configured to generate a respective information record for the completed purchase with corresponding information within transaction information database 114*k*, which initially indicates that the purchase has not yet been redeemed with respect to the primary service, each secondary service, and any facility specified for the purchased offered service.

Figure 4B:
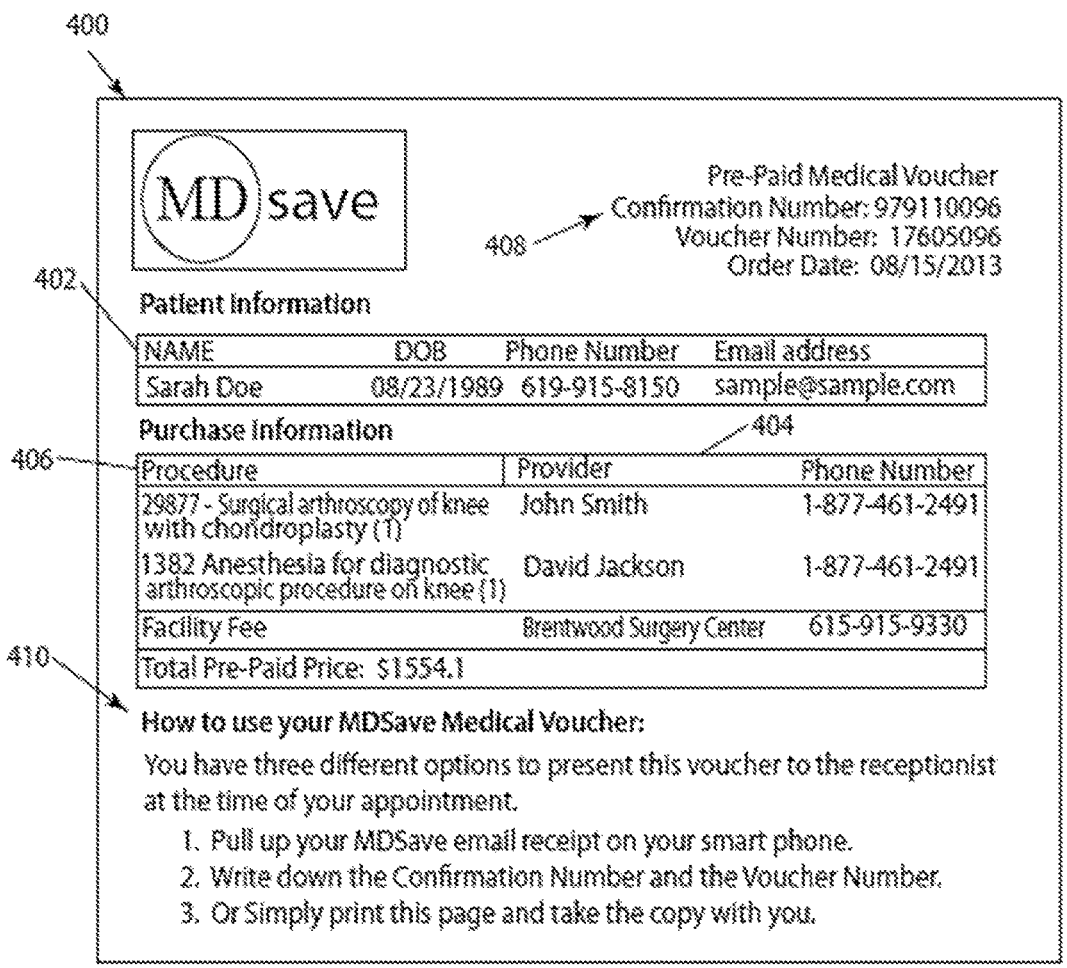
FIG. 4B is an illustration of an example voucher that may be generated within a user interface by functions provided within a customer portal for a purchased service that is offered as a bundled set of services in accordance with exemplary embodiments of the present invention.

Purchasing server 126 can also be configured to, upon processing the payment for the purchase of the offered service that is being offered as a primary service in conjunction with a bundled set of services, generate a voucher for the customer user within the user interface for the purchased service that can be utilized by the customer user to redeem the purchase and receive the service from the corresponding physician specified for each of the services of the bundled set of services (the providers of marketplace system 100 can have pre-arranged agreements with providers registered with the system that the providers will agree to honor such vouchers generated by purchasing server 126 for purchased services). An example of such a voucher for a bundled set of services is illustrated in FIG. 4B. As depicted in the example, example voucher 400 can be generated to include identifying information for the customer user 402, identifying and contact information for each physician specified for a service and any facility included in the offered service 404, a description of each service of the purchased service 406, a confirmation number 408 for the purchase, which may be generated by purchasing server 126 based on the unique transaction identifier that is included in the respective information record for the purchase that is maintained within transaction information database 114*k*, and instructions for redeeming the voucher 410. The confirmation number (or any other suitable redemption information such as a one or two dimensional bar code, a QR code, or any other form of machine readable information) may also be provided in the electronic confirmation message to the customer user and electronic notifications to the physician user that will be performing the service and the provider user for the offered service sent by purchasing system 126 to the customer user. The voucher can be presented to the user within the user interface, for example, as printable and/or machine readable form.

Referring again to the exemplary embodiment illustrated in FIG. 2, customer portal 120 may also be configured to, upon a user having a customer account registered with server system 110 logging into his or her customer account (for example, by accessing a login user interface element or a login screen within the user interface implemented by application server 116 to provide the user name and password associated with the account), provide a user interface element within the user interface that is accessible by the user to access various account management functions through a profile management interface provided by account management service 122. For example, such a profile management interface may be implemented to allow the customer user to manage personal information, view a history of purchase transactions performed by the user within server system 110 (and relevant information for each purchase including voucher redemption status), manage and review any continuing prescriptions, and print vouchers generated for services purchased and otherwise access voucher redemption information.

As noted above, in exemplary embodiments, a user operating a client system to access application server 116 via a corresponding client application executing on the client system may be provided with a user interface element on any page implemented by navigation and search service 124 that is accessible by the user to initiate a registration with server system 110, and navigation and search service 124 may be configured to, in response a user accessing the user interface element, provide further user interface controls for allowing the user to specify a type of user account that the user intends to register with server system 110.

Upon the user indicating an intention to register as a physician user, the user will be able to initiate a registration session with account management service 131 to register a physician account with server system 110. Account management service 131 may be configured, for example, to implement a user interface that includes a series of pages with user interface controls accessible by the user to guide the user through the account registration process and prompt the user to input various types of information or media to be maintained by database server 112 within a respective account information record that is established for the user within physician profile database 114*b* such as, for example, name, practice specialty, office location(s) and hours, a profile picture, contact information (such as an email address and/or a telephone number), biographical information (such as awards, honors, publications, patient testimonials, and other information that can be helpful for marketing the physician to customers accessing the system), URLs or references to websites and social media profiles, compensation information (indicating a financial account for receiving payment for purchases of services offered by the physician via the system), information pertaining to outside facilities that are used for particular services performed by the physician (for example, information pertaining to particular hospitals or clinics such as name, address, contact information, facility fee, and compensation information indicating a financial account that is used by the facility for receiving a facility fee), and any other suitable identifying or descriptive information. The user interface may also be implemented by account management service 131 to prompt the user for any group affiliation codes or hospital affiliation codes.

Account management service 131 can be configured to access database server 112 to create the respective account information record for the user within physician profile database 114*b* based on the information input by the user during the registration process. Account management service 131 can be further configured to generate the unique physician account identifier for the created account information record, which may be used, for example, to index and reference the created account information record within database server 112. For any group affiliation codes or hospital affiliation codes submitted by the user, account management service 131 can be configured to include the unique physician account identifier for the created account information record in the account information record for the practice group that is maintained within practice group profile database 114*c* for each practice group corresponding to a submitted group affiliation code and in the account information record for the hospital system that is maintained within hospital system profile database 114*d* for each hospital system corresponding to a submitted hospital affiliation code, as well as include the corresponding hospital system and group practice account identifiers within the account information record for the user within physician profile database 114*b*. The created account information record can also be identified with a unique user name and protected by a password, which can be used by the user to log into the associated physician account when accessing application server 116.

In exemplary embodiments, the user interface implemented by account management service 131 may be further configured to provide user interface controls for requesting authorization for payment of a predetermined fee to gain access to the ability to offer healthcare services for purchase within marketplace system 100. Such a fee may be, for example, a onetime charge or a periodic charge (such as a monthly, biannual, or annual fee). In conjunction with such a payment authorization request, the user interface controls provided by account management service 131 may also be implemented to prompt the user to input the payment information specifying the funding source the user will use for payment of the predetermined access fee. The payment information input by the user may be an instruction to use the compensation information included within the respective account information record established for the user within physician profile database 114*a* or submission of alternative payment information such as, for example, bank account information, credit or debit card information, or other electronic payment information (such as information for utilizing an account the user has with PayPal or any another entity facilitating payments and money transfers to be made through the Internet). Account management service 131 can be configured to, upon the authorization and appropriate payment information being provided by the user, access a corresponding third-party payment servicing system and utilize the payment information to direct the payment servicing system to transfer the amount for the payment authorized by the user from the account servicer of the user to a financial account maintained by the providers of marketplace system 100. Alternatively, the user interface implemented by account management service 131 may be configured to provide user interface controls for receiving an activation code to gain access to the ability to offer healthcare services for purchase within marketplace system 100 or may be configured to provide such access to the user in response to receiving a particular group or hospital affiliation code from the user. In this regard, the respective account information record established for the user within physician profile database 114*b* can further include an account status that is managed by account management service 131 for the user indicating whether the user is presently provided with the ability to offer healthcare services for purchase within marketplace system 100.

Upon a user registering a physician account with server system 110 to establish an account information record within physician profile database 114*b* and logging into his or her physician account (for example, by accessing a login user interface element or a login screen within the user interface implemented by navigation and search service 124 to provide the user name and password associated with the account), the user may be directed to a physician account page implemented by provider portal 130 that provides a set of user interface controls that can be accessed by the user to access functionality provided by procedure management service 133 to offer healthcare services for purchase by customer users registered with the system, functionality provided by transaction processing service 136 to request payment for purchased services that have been performed, and to access various account management functions provided by account management service 131.

Upon the user indicating an intention to offer a healthcare service for purchase (for example, by selecting a "Offer Service" tab within the physician account page implemented by provider portal 130), the user will be able to initiate a service offering with procedure management service 133 to offer a healthcare service for purchase via server system 110. Procedure management service 133 may be configured, for example, to implement a user interface that includes a series of pages with user interface controls accessible by the user to guide the user through the service offering process and prompt the user to input various types of information to be maintained by database server 112 within a respective information record that is established in association with the unique physician account identifier for the physician within service offer database 114*h*. For example, the user may be provided with a drop-down menu providing a list of selectable medical specialties and, upon selecting a particular medical specialty, the user can be presented with a list of selectable healthcare services for which an information record for the service is maintained within available services database 114*g* in association with the specialty.

Upon the user selecting a particular service from this list, procedure management service 133 can assist the user with offering the service for purchase and establish the respective information record for the offered service within service offer database 114*h* by populating the information record with the unique procedure identifier for the information record within available services database 114*g* for the selected service, the unique account identifier for the account information record for the physician user within physician profile database 114*b* as both the provider that is offering the service through the system and the physician user will perform the service, a location at which the service will be performed, the unique account identifier for the account information record (within physician profile database 114*b*, practice group profile database 114*c*, or hospital system profile database 114*d*) of the provider for which payment for the service when purchased through the system is to be directed (or, alternatively, other financial account information) as indicated by user input received from the physician user, a payment amount to be transferred to the provider or other financial account for which payment for the service is to be directed as specified by user input received from the physician user, a discounted price for purchasing the service within marketplace system 100 (which may be calculated, for example, by adding a negotiated commission fee to the payment amount specified by the physician user), a regular price for the service when the service is purchased outside of the system, additional descriptive information that may be provided via input received from the physician user, a procedure offer identifier, and any other suitable information (such as an indication that the service is required to be performed at an outside facility and relevant facility information as specified by user input received from the physician user).

As discussed above, when a payment for an offered service is processed by purchasing service 126, a financial account maintained by the providers of marketplace system 100 holds the payment amount to be transferred to the provider for which payment for the service is to be directed until an indication is received that the purchased service has been performed by the physician that is specified in service offer database 114*h* for performing the service. Purchasing server 126 can also generate a respective information record for the completed purchase within transaction information database 114*k*, which initially indicates that the purchase has not yet been redeemed with respect to a purchase of an individual service or with respect to each service for a purchase of a bundled set of services, and generate a voucher for the customer user to use with respect to the purchased service to redeem the purchase by receiving the service from the physician specified for each service included in the purchase. Such a voucher can include a confirmation number or other redemption code for the purchase.

Upon the user indicating an intention to request payment for a purchased service that have been performed (for example, by selecting a "Voucher Processing" tab within the physician account page implemented by provider portal 130), the user will be able to initiate a voucher processing session with transaction processing service 136. In particular, transaction processing service 136 may be configured, for example, to implement a voucher history page within the user interface that presents information relevant to the physician user for a list of purchases for which the respective information record for the purchase that is maintained within transaction information database 114*k* includes the unique physician account identifier for the physician user within physician profile database 114*b* as the physician user that is designated as performing a service included the purchase (for example, a primary or secondary service for a bundled set of services). The relevant information for each listed purchase may include, for example, the voucher confirmation number or redemption code, name and contact information for the customer user, a description of the service the physician user is designated as performing for the purchase, a purchase date, and a voucher redemption status. Such a voucher history page may also be accessed in association with the user account for the physician user to verify vouchers presented customers requesting to have a service performed in association with a voucher.

The voucher history page can also provide a user interface element in association with each of the listed purchases for which the voucher redemption status for the service the physician user is designated as performing indicates the service has not been performed that is accessible by the physician user to submit a verification to application server 116 that the physician user has performed the service for the customer user in accordance with the purchase. Transaction processing service 136 can be configured to, upon such a verification being submitted, initiate a transfer of the payment amount specified for the service performed by the physician user in service offer database 114*h* and held in the financial account maintained by the providers of marketplace system 100 to the financial account listed for receiving the payment amount for service that is specified in service offer database 114*h*. Additionally, if the service performed by the physician is a primary service of a bundled set of services for which a particular outside facility that has been selected for performing the primary service, transaction processing service 136 can be configured to initiate a transfer or otherwise direct a disbursement of the facility fee specified for the service performed by the physician user in service offer database 114*h* and held in the financial account maintained by the providers of marketplace system 100 to the financial account for the facility that is indicated by the compensation information for the facility. Transaction processing service 136 can be configured to update the indication of whether the purchase has been redeemed with respect to that particular service (and facility if one is associated with the service in the purchase) and include the redemption date for that particular service in the information record for the purchased service that is maintained within transaction information database 114*k*. In addition, transaction processing service can further be configured to send electronic notifications to the customer user, the physician user, and the provider user for the offered service (as specified according to the corresponding information records within service offer database 114*h* and transaction information database 114*k*), for example, by way of email utilizing the contact information specified in the respective account information records for the customer, the physician, and the provider for the offered service.

Upon the user indicating an intention within the physician account page implemented by provider portal 130 to access various account management functions, the user can access various user interface elements provided by account management service 131 to, for example, manage personal and payment or purchase information, manage information pertaining to services offered for purchase by the physician user, manage group practice and hospital affiliations, and view a history of transactions performed for services offered for purchase by the physician user within server system 110 (and relevant information for each purchase including voucher redemption status).

Referring again to FIG. 2, in exemplary embodiments, when a user operating a client system to access application server 116 via a corresponding client application executing on the client system initiates a registration with server system 110 and specifies an intention to register as a practice group administrator (for example, via a user interface element on any page implemented by navigation and search service 124), the user will be able to initiate a registration session with account management service 131 to register a practice group account with server system 110. Account management service 131 may be configured, for example, to implement a user interface that includes a series of pages with user interface controls accessible by the user to guide the user through the account registration process and prompt the user to input various types of information or media to be maintained by database server 112 within a respective account information record that is established for the user within practice group profile database 114*c* such as, for example, practice group name, location and hours, contact information (such as an email address and/or a telephone number), URLs or references to websites and social media profiles for the practice group, information pertaining to outside facilities that are used for particular procedures by physicians affiliated with the practice group, (for example, information pertaining to particular hospitals or clinics such as name, address, contact information, facility fee, and compensation information indicating a financial account that is used by the facility for receiving a facility fee), compensation information (indicating a financial account for receiving payment for purchases of services that are performed by affiliated physicians via the system), and any other suitable identifying or descriptive information.

The user interface may also be implemented by account management service 131 to prompt the user to specify affiliated physician users and enter any hospital affiliation codes. In this regard, account management service 131 may be implemented to provide user interface controls allowing the user to search for physician users registered with server system 110 (for example, by name and/or email address), access physician profile database 114a to locate account information records for physician users matching the search criteria, and provide user interface controls allowing the user to register an affiliation within server system 110 with any physician user returned in the search. Account management service 131 may be implemented to provide user interface controls allowing the user to register a new physician account for an affiliated physician with server system 110 in a manner similar to that described above for physician users registration and may also provide an option for the user to indicate whether electronic messages sent by server system 110 in association with services offered the practice group and performed by the physician user should be delivered to an email address for the physician, an email address for the practice group, or both.

Account management service 131 can be configured to access database server 112 to create the respective account information record for the user within practice group profile database 114a based on the information input by the user during the registration process. Account management service 131 can be further configured to generate the unique practice group account identifier for the created account information record, which may be used, for example, to index and reference the created account information record within database server 112. For any affiliated physician users or hospital affiliation codes specified by the user, account management service 131 can be configured to include the unique practice group account identifier for the created account information record in the account information record for the physician that is maintained within physician profile database 114a for each specified physician user and in the account information record for the hospital system that is maintained within hospital system profile database 114d for each hospital system corresponding to a submitted hospital affiliation code, as well as include the corresponding hospital system and physician account identifiers within the account information record for the user within practice group profile database 114c. The created account information record can also be identified with a unique user name and protected by a password, which can be used by the user to log into the associated practice group account when accessing application server 116.

In exemplary embodiments, the user interface implemented by account management service 131 may be further configured to provide user interface controls for requesting authorization for payment of a predetermined fee to gain access to the ability to offer healthcare services for purchase within marketplace system 100. Such a fee may be, for example, a one-time charge or a periodic charge (such as a monthly, biannual, or annual fee). The fee may also be assessed for each new physician account registered with server system 110 by the user as an affiliated physician of the practice group. Account management service 131 can be configured to, upon the authorization and appropriate payment information being provided by the user via the user interface controls provided by account management service 131, access a corresponding third-party payment servicing system and utilize the payment information to direct the payment servicing system to transfer the amount for the payment authorized by the user from the account servicer of the user to a financial account maintained by the providers of marketplace system 100. Alternatively, the user interface implemented by account management service 131 may be configured to provide user interface controls for receiving an activation code to gain access to the ability to offer healthcare services for purchase within marketplace system 100 or may be configured to provide such access to the user (and/or any new physician accounts registered for affiliated physicians by the user with server system 110) in response to receiving a particular group or hospital affiliation code from the user. In this regard, the respective account information record established for the user within practice group profile database 114c can further include an account status that is managed by account management service 131 for the user indicating whether the practice group is presently provided with the ability to offer healthcare services for purchase within marketplace system 100.

Upon a user registering a practice group account with server system 110 to establish an account information record within practice group profile database 114c and logging into his or her practice group account (for example, by accessing a login user interface element or a login screen within the user interface implemented by navigation and search service 124 to provide the user name and password associated with the account), the user may be directed to a practice group account page implemented by provider portal 130 that provides a set of user interface controls that can be accessed by the user to access functionality provided by procedure management service 133 to offer healthcare services performed by affiliated physicians for purchase by customer users registered with the system, functionality provided by transaction processing service 136 to request payment for purchased services that have been performed, and to access various account management functions provided by account management service 131.

Upon the user indicating an intention to offer a healthcare service for purchase (for example, by selecting a "Offer Service" tab within the practice group account page implemented by provider portal 130), the user will be able to initiate a service offering with procedure management service 133 to offer a healthcare service performed by affiliated physicians for purchase via server system 110. Procedure management service 133 may be configured, for example, to implement a user interface that includes a series of pages with user interface controls accessible by the user to guide the user through the service offering process and prompt the user to input various types of information to be maintained by database server 112 within a respective information record that is established within service offer database 114h in association with the unique practice group account identifier for the practice group. For example, the user may be provided with a drop-down menu providing a list of selectable medical specialties and, upon selecting a particular medical specialty, the user can be presented with a list of selectable healthcare services for which an information record for the service is maintained within available services database 114g in association with the specialty.

Upon the user selecting a particular service from this list, procedure management service 133 can assist the user with offering the service for purchase and establish the respective information record for the offered service within service offer database 114h. In particular, procedure management service 133 can present the user with a selectable list of the physician users affiliated with the practice group from which the user can submit an indication one or more of the affiliated physicians with which to offer the service in conjunction with the practice group account. For each selected affiliated physician user, procedure management service 133 can establish a respective information record for the offered service within service offer database 114h by populating the information record with the unique procedure identifier for the information record within available services database 114g for the selected service, the unique account identifier for the account information record for the practice group within physician profile database 114b as the provider that is offering the service through the system, the unique account identifier for the account information record for the physician user within physician profile database 114b as the physician user will perform the service, a location at which the service will be performed, the unique account identifier for the account information record (within physician profile database 114b, practice group profile database 114c, or hospital system profile database 114d) of the provider for which payment for the service when purchased through the system is to be directed (or, alternatively, other financial account information) as indicated by user input received from the practice group administrator, a payment amount to be transferred to the provider or other financial account for which payment for the service is to be directed as specified by user input received from the practice group administrator, a discounted price for purchasing the service within marketplace system 100 (which may be calculated, for example, by adding a negotiated commission fee to the payment amount specified by the practice group administrator), a regular price for the service when the service is purchased outside of the system, additional descriptive information that may be provided via input received from the practice group administrator, a procedure offer identifier, and any other suitable information (such as an indication that the service is required to be performed at an outside facility and relevant facility information as specified by user input received from the practice group administrator).

In exemplary embodiments, procedure management service 133 can also assist the practice group administrator with offering services for purchase as a bundled set of services within marketplace system 100 and establishing the respective information record for the service offered as a bundled set of services within service offer database 114h. In particular, procedure management service 133 can present the user with an option to indicate that a particular service selected by the user should be offered as a primary service of a bundled set of services or, alternatively, the information record for a particular service selected by the user that is maintained within available services database 114g can include an indication that the service can be offered by providers within marketplace system 100 as a primary service of a bundled set of a plurality of services.

For a selected service for which such an indication is provided, procedure management service 133 may be configured, for example, to implement user interface controls accessible by the user to guide the user through the process for offering the selected service as a primary service of a bundled set of services and prompt the user to input various types of information to populate a respective information record that is established in association with the unique practice group account identifier for the practice group within service offer database 114h. Procedure management service 133 can first present the user with a selectable list of the physician users affiliated with the practice group from which the user can submit an indication of affiliated physicians with which to offer the primary service in conjunction with the practice group account and then populate the information pertaining to the primary service in the information record with the unique procedure identifier for the information record within available services database 114g for the selected service, the unique account identifier for the account information record for the practice group within physician profile database 114b as the provider that is offering the primary service through the system, the unique account identifier for the account information record for the physician user within physician profile database 114b as the physician user will perform the primary service, a location at which the primary service will be performed, the unique account identifier for the account information record (within physician profile database 114b, practice group profile database 114c, or hospital system profile database 114d) of the provider for which payment for the primary service when purchased through the system is to be directed (or, alternatively, other financial account information) as indicated by user input received from the practice group administrator, a payment amount to be transferred to the provider or other financial account for which payment for the primary service is to be directed as specified by user input received from the practice group administrator, a discounted price for purchasing the primary service within marketplace system 100 (which may be calculated, for example, by adding a negotiated commission fee to the payment amount for the primary service specified by the practice group administrator), a regular price for the primary service when the primary service is purchased outside of the system, additional descriptive information that may be provided via input received from the practice group administrator, a procedure offer identifier, and any other suitable information.

Procedure management service 133 can then receive an indication, either from the information record for a particular service selected by the user that is maintained within available services database 114g or through selections made by the user of services offered by affiliated physicians for which an information record for the service is maintained within available services database 114g, of one or more secondary services to be included in the bundled set of services. Procedure management service can then populate the information pertaining to each secondary service in the information record with the unique procedure identifier for the information record within available services database 114g for the secondary service (or the secondary procedure identifier that is included in the available services database 114g to uniquely identify the particular secondary service in association with the unique procedure identifier for the offered primary service where the information record for the primary service being offered in the available services database 114g includes an indication that the service is offered as a primary service of a bundled set of services), the unique physician account identifier for the account information record within physician profile database 114b of the physician user that will perform the secondary service, a location at which the service will be performed, the unique account identifier for the account information record (within physician profile database 114b, practice group profile database 114c, or hospital system profile database 114d) of the provider for which payment for the primary service when purchased through the system is to be directed (or, alternatively, other financial account information) as indicated by user input received from the practice group administrator, a payment amount to be transferred to the provider or other financial account for which payment for the secondary service is to be directed as specified by user input received from the practice group administrator, a discounted price for purchasing the secondary service within marketplace system 100 (which may be calculated, for example, by adding a negotiated commission fee to the payment amount for the secondary service specified by the practice group administrator), a regular price for the secondary service when the secondary service is purchased outside of the system, and an indication of whether performance of the secondary service is optional or required in association with performance of the primary service. Procedure management service can further populate the information in the information record with an indication of whether the primary service is to be performed at an outside facility and, if the primary service is to be performed at an outside facility, items of information pertaining to each of one or more facilities that may be used to perform the primary service such as, for example, name, address, contact information, facility fee, and compensation information indicating a financial account that is used by the facility for receiving a facility fee (as specified by user input received from the practice group administrator).

Upon the user indicating an intention to request payment for a purchased service that have been performed (for example, by selecting a "Voucher Processing" tab within the practice group account page implemented by provider portal 130), the user will be able to initiate a voucher processing session with transaction processing service 136. In particular, transaction processing service 136 may be configured, for example, to implement a voucher history page within the user interface that presents information relevant to the practice group administrator for a list of purchases for which the respective information record for the purchase that is maintained within transaction information database 114*k* includes the unique practice group account identifier for the practice group within practice group profile database 114*c* as the provider that is offering the service for purchase (for example, a primary or secondary service for a bundled set of services). The relevant information for each listed purchase may include, for example, the voucher confirmation number or redemption code, name and contact information for the customer user, a description of the service the physician user is designated as performing for the purchase, a purchase date, and a voucher redemption status.

The voucher history page can also provide a user interface element in association with each of the listed purchases for which the voucher redemption status for the service indicates the service has not been performed that is accessible by the practice group user to submit a verification to application server 116 that the affiliated physician user specified as performing the service has performed the service for the customer user in accordance with the purchase. Transaction processing service 136 can be configured to, upon such a verification being submitted, initiate a transfer of the payment amount specified for the service performed by the affiliated physician user in service offer database 114*h* and held in the financial account maintained by the providers of marketplace system 100 to the financial account listed for receiving the payment amount for service that is specified in service offer database 114*h*. Additionally, if the service performed by the physician is a primary service of a bundled set of services for which a particular outside facility that has been selected for performing the primary service, transaction processing service 136 can be configured to initiate a transfer of the facility fee specified for the service performed by the physician user in service offer database 114*h* and held in the financial account maintained by the providers of marketplace system 100 to the financial account for the facility that is indicated by the compensation information for the facility. Transaction processing service 136 can be configured to update the indication of whether the purchase has been redeemed with respect to that particular service (and facility if one is associated with the service in the purchase) and include the redemption date for that particular service in the information record for the purchased service that is maintained within transaction information database 114*k*. In addition, transaction processing service can further be configured to send electronic notifications to the customer user, the physician user, and the provider user for the offered service (as specified according to the corresponding information records within service offer database 114*h* and transaction information database 114*k*), for example, by way of email utilizing the contact information specified in the respective account information records for the customer, the physician, and the provider for the offered service.

Upon the user indicating an intention within the practice group account page implemented by provider portal 130 to access various account management functions, the user can access various user interface elements provided by account management service 131 to, for example, manage profile and payment or compensation information for both the practice group and affiliated physicians, manage information pertaining to services offered for purchase by both the practice group and affiliated physicians, manage physician and hospital system affiliations, and view a history of transactions performed for services offered for purchase by the practice group within server system 110 (and relevant information for each purchase including voucher redemption status).

In exemplary embodiments, when a user operating a client system to access application server 116 via a corresponding client application executing on the client system initiates a registration with server system 110 and specifies an intention to register as a hospital system administrator (for example, via a user interface element on any page implemented by navigation and search service 124), the user will be able to initiate a registration session with account management service 131 to register a hospital system account with server system 110. Account management service 131 may be configured, for example, to implement a user interface that includes a series of pages with user interface controls accessible by the user to guide the user through the account registration process and prompt the user to input various types of information or media to be maintained by database server 112 within a respective account information record that is established for the user within hospital system profile database 114*d* such as, for example, contact information (such as an email address and/or a telephone number), information pertaining to outside facilities that can be used for particular procedures by physicians affiliated with the hospital system (for example, information pertaining to particular hospitals or clinics such as name, address, contact information, facility fee, and compensation information indicating a financial account for that is used by the facility for receiving a facility fee), compensation information (indicating a financial account for receiving payment for purchases of services performed by affiliated physicians via the system), and any other suitable identifying or descriptive information.

The user interface may also be implemented by account management service 131 to prompt the user to specify affiliated physician users and enter any practice group affiliation codes. In this regard, account management service 131 may be implemented to provide user interface controls allowing the user to search for physician users registered with server system 110 (for example, by name and/or email address), access physician profile database 114*a* to locate account information records for physician users matching the search criteria, and provide user interface controls allowing the user to register an affiliation within server system 110 with any physician user returned in the search. Account management service 131 may also provide an option for the user to indicate whether electronic messages sent by server system 110 in association with services offered (or sold on-site) by the hospital system and performed by the affiliated physician user should be delivered to an email address for the physician, an email address for the hospital system, or both.

Account management service 131 can be configured to access database server 112 to create the respective account information record for the user within hospital system profile database 114*d* based on the information input by the user during the registration process. Account management service 131 can be further configured to generate the unique hospital system account identifier for the created account information record, which may be used, for example, to index and reference the created account information record within database server 112. For any affiliated physician users or group practice affiliation codes specified by the user, account management service 131 can be configured to include the unique hospital system account identifier for the created account information record in the account information record for the physician that is maintained within physician profile database 114*a* for each affiliated physician user and in the account information record for the practice group that is maintained within practice group profile database 114*c* for each practice group corresponding to a submitted hospital affiliation code, as well as include the corresponding practice group and physician account identifiers within the account information record for the user within hospital system profile database 114*d*. The created account information record can also be identified with a unique user name and protected by a password, which can be used by the user to log into the associated hospital system account when accessing application server 116. Moreover, the created account information record can also be identified with a respective unique user name and protected by a password for any other users authorized to access the associated hospital system account when accessing application server 116. As noted above, a hospital system account may be associated with and accessible by a plurality of users having different levels of access rights to the various functionality provided within provider portal 130 for hospital system accounts.

In exemplary embodiments, the user interface implemented by account management service 131 may be further configured to provide user interface controls for requesting authorization for payment of a predetermined fee to gain access to the ability to offer healthcare services for purchase within marketplace system 100. Such a fee may be, for example, a onetime charge or a periodic charge (such as a monthly, biannual, or annual fee). Account management service 131 can be configured to, upon the authorization and appropriate payment information being provided by the user via the user interface controls provided by account management service 131, access a corresponding third-party payment servicing system and utilize the payment information to direct the payment servicing system to transfer the amount for the payment authorized by the user from the account servicer of the user to a financial account maintained by the providers of marketplace system 100. Alternatively, the user interface implemented by account management service 131 may be configured to provide user interface controls for receiving an activation code to gain access to the ability to offer healthcare services for purchase within marketplace system 100 or may be configured to provide such access to the user in response to receiving a particular hospital affiliation code from the user. In this regard, the respective account information record established for the user within hospital system profile database 114*d* can further include an account status that is managed by account management service 131 for the user indicating whether the hospital system is presently provided with the ability to offer healthcare services for purchase within marketplace system 100.

Upon a hospital system administrator registering a hospital system account with server system 110 to establish an account information record within practice group profile database 114*c* and an authorized user logging into the hospital system account (for example, by accessing a login user interface element or a login screen within the user interface implemented by navigation and search service 124 to provide the user name and password associated with the account), the user may be directed to a hospital system account page implemented by provider portal 130 that provides a set of user interface controls that can be accessed by the user to access functionality provided for users of hospital system accounts.

In exemplary embodiments, the functionality that is provided within provider portal 130 for users of hospital system accounts can be substantially similar to the functionality that may be provided within provider portal 130 for users of practice group accounts as described for the non-limiting examples discussed above. For instance, provider portal 130 can implement functionality within the user interface allowing a user of a hospital system account to offer a healthcare service for purchase within marketplace system 100 (in association with an affiliated physician or a physician that is affiliated with an affiliated practice group), offering services for purchase as a bundled set of services within marketplace system 100, access a voucher history page within the user interface that presents information relevant to the hospital group user for a list of purchases for which the respective information record for the purchase that is maintained within transaction information database 114*k* includes the unique hospital system account identifier for the hospital system within hospital system profile database 114*d* as the provider that is offering the service for purpose (for example, a primary or secondary service for a bundled set of services), initiate a voucher processing session to submit a verification and request payment processing for a purchased service that have been performed, and access various account management functions to, for example, manage profile and payment or compensation information for both the hospital system and affiliated physicians, manage information pertaining to services offered by both the hospital system and affiliated physicians for purchase, manage physician and group practice affiliations, and view a history of transactions performed for services offered for purchase by the hospital system within server system 110 (and relevant information for each purchase including voucher redemption status).

In exemplary embodiments, the functionality that is provided within provider portal 130 for users of hospital system accounts can vary in certain respects from the functionality that may be provided within provider portal 130 for users of practice group accounts. For example, with respect to physicians that are affiliated with the hospital system account, users of hospital system accounts may only be provided with access rights (for example, to view, modify, and specify in a service being offered by the hospital system for purchase) to services offered for purchase by affiliated physician users that have been specified by the physician users as being hospital procedures with respect to the physician accounts. Hospital system users may also be provided with functionality to, as an alternative to selecting a service by accessing a list of selectable medical specialties when initiating a service offering with procedure management service 133 to offer a service performed by affiliated physicians for purchase via server system 110, submit a search query for a service by inputting descriptive terms or a medical code number that is used to identify the service (for example, according to the CPT code set) or access a list of affiliated physicians and, upon selecting a particular affiliated physician from the list, be presented with a list of selectable healthcare services for which an information record for the service is maintained within service offer database 114*h* that indicates the selected physician as the physician that will perform the service. In addition, because a hospital system may be more likely to offer a higher quantity of services for purchase as a bundled set of services within marketplace system 100 than other types of provider users, the functionality implemented by provider portal 130 within the user interface for allowing a user of a hospital system account to manage information pertaining to services offered by the hospital system for purchase and to view a history of transactions performed for services offered for purchase by the hospital system within server system 110 may include an additional user interface element that is accessible by a user for the hospital system account manage and view information pertaining to only services that are offered by the hospital system as a bundled set of services.

In exemplary embodiments, healthcare marketplace system 100 may be further implemented to provide an interactive pricing tool for use by healthcare service providers in setting prices for healthcare services being offered to prospective patients through the system, including bundled sets of services for which the network-based application facilitates a disbursed distribution of the payment among multiple service providers that perform services (or provide use of a health care facility for performing a service) included in a bundled set of services. Such exemplary embodiments, as described in greater detail below, can provide mechanisms for assisting providers with determining a fee schedule for services to be offered for purchase via server system 110 and provide interactive features to help ensure that providers will be able to receive compensation amounts that are accurately reflective of the business costs, desired returns, and value placed by providers for services they provide for patients, taking into account factors that may include training costs, utilizing up-to-date technologies, qualifications, length of time in practice, reputation, skills, amount of charity care given, geographic area, and other relevant factors. Exemplary embodiments can thereby assist in reducing the amount of overhead necessary to establish and monitor a well-developed and maintained fee schedule that is market sensitive, fiscally responsible, and organizationally sound, particularly for bundled payment arrangements for services that are delivered by two or more providers during a single episode of care for a patient.

Figure 6:
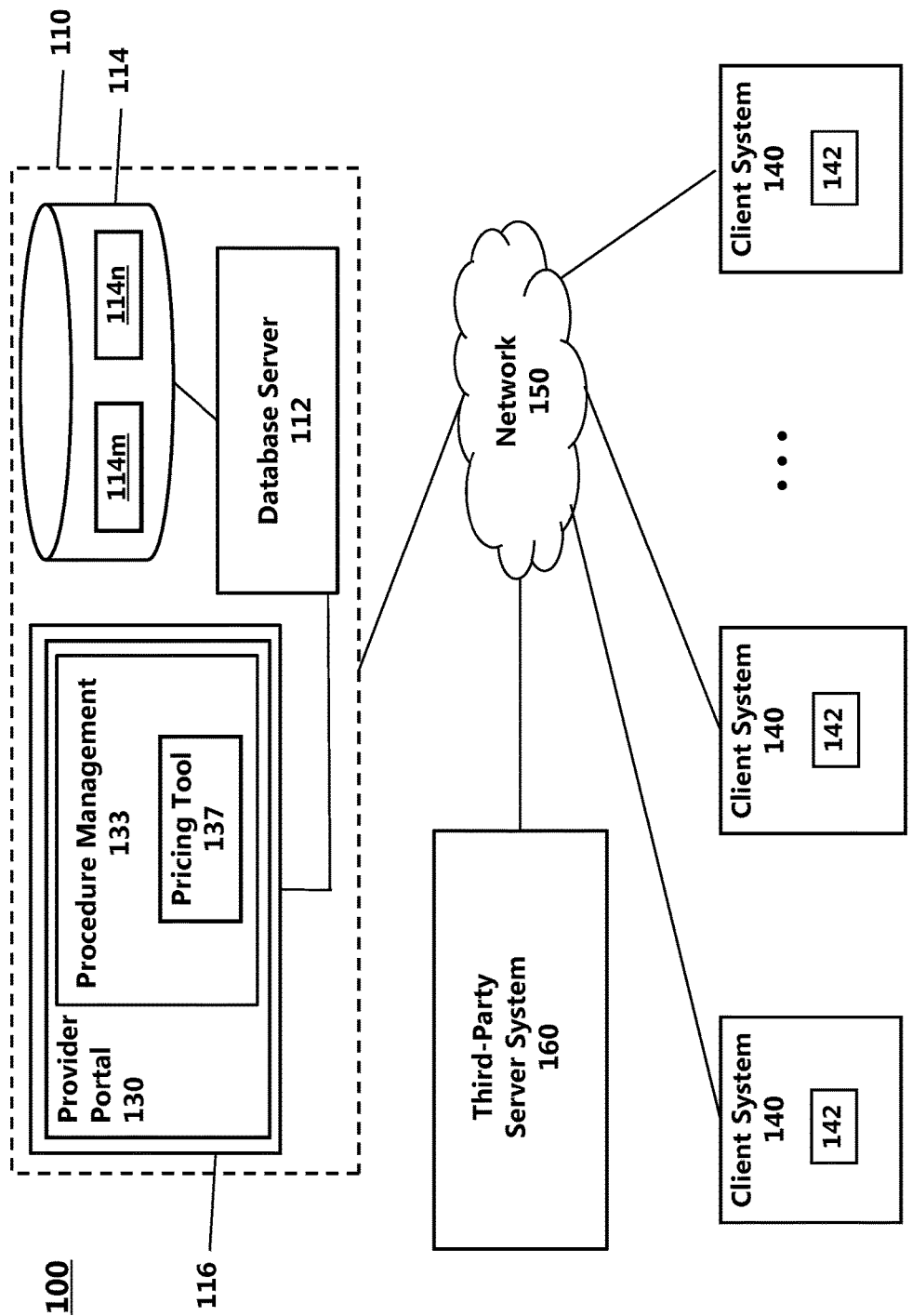
FIG. 6 is a schematic diagram illustrating a second example network architecture for a healthcare marketplace system that can be configured to implement exemplary embodiments of the present invention.

Referring now to FIG. 6, a schematic diagram illustrating an example network architecture for healthcare marketplace system 100 within which an exemplary embodiment of a provider pricing tool in accordance with the present invention is implemented. It should of course be understood that FIG. 6 is intended as an example, not as an architectural limitation for different embodiments of the present invention, and therefore, the particular elements depicted in FIG. 6 should not be considered limiting with regard to the environments within which exemplary embodiments of the present invention may be implemented.

In the example illustrated in FIG. 6, the particular components that are utilized for providing the provider pricing tool are integrated within system 100 in conjunction with the components of the system as described above with reference to the exemplary embodiments illustrated FIGS. 1 and 2. More specifically, the pricing tool 137 is shown in FIG. 6 as being implemented within procedure management service 133 included within provider portal 130, and data store 114 further comprises a service pricing information database 114*m* and a cost adjustment information database 114*n* that are maintained by database server 112, are accessed by application server 116 via database services provided at a front end by database server 112, and retain information collected from a variety of data sources that is utilized in providing the services offered via the provider pricing tool within the network service provided by the application server, as described below in greater detail.

In the present exemplary embodiment, service pricing information database 114*m* is used to maintain information records with extensive medical cost data for an exhaustive set of healthcare services that can be offered by providers registered with server system 110 for purchase by customer users registered with the server system, and cost adjustment information database 114*n* is used to maintain a comprehensive set of data pertaining to location-based pricing adjustments that can be applied to the medical cost data maintained in service pricing information database 114*m* based on, for example, geographic zones or particular facilities within which healthcare services may be performed. In exemplary embodiments, the respective information records for healthcare services that are maintained in service pricing information database 114*m* and the information that populates the respective information record for each service can be created and maintained by a back-end administrator of server system 110. Likewise, the information that populates cost adjustment information database 114*n* can also be compiled and maintained by such a back-end administrator. The information used to populate the information maintained in service pricing information database 114*m* and cost adjustment information database 114*n* can be compiled based on medical information and cost data sourced from a number of public and private healthcare information sources and can be continually updated in response to updates to the information sources to ensure that the underlying medical pricing and cost adjustment data upon which the information compiled in service pricing information database 114*m* and cost adjustment information database 114*n* is based is up-to-date.

While service pricing information database 114*m* is being described in the present exemplary embodiment as being a separate database that is maintained within data store 114, in view of the overlap between the sets of information maintained within service pricing information database 114*m* and available services database 114*g*, in exemplary embodiments, the information records maintained in service pricing information database 114*m* can be maintained by database server 112 in a group with or otherwise integrated with available services database 114g. In particular, as with available services database 114g, for each service for which an information record is maintained within service pricing information database 114m, various items of information relevant to the service, such as name, procedure detail, one or more medical specialties with which the procedure is commonly associated, one or more medical code numbers identifying the service according to nomenclature used by formal medical classification systems (for example, one or more codes that are used to identify or correspond to the service according to the CPT code set and/or one or more codes that is used to identify or correspond to the service according to the Healthcare Common Procedure Coding Systems (HCPCS) code set), a service identifier that is used by application server 116 to uniquely identify the particular service, and any other suitable information may be included in the respective information record for the service that is maintained within service pricing information database 114m. Moreover, for purposes of utilization by pricing tool 137 as will be described below, the items of information included within the respective information record for each service that is maintained within service pricing information database 114m can further include a procedure category within which the service is determined to be categorized as a sub-procedure (for example, according to formal or typical medical classifications for procedures or otherwise configured in any suitable manner by a back-end administrator of server system 110) and a set of pricing information that is more comprehensive than the examples of cost information described above with reference to available services database 114g.

Additionally, in exemplary embodiments, in a manner that is similar to available services database 114g, the information record for each service that is maintained within service pricing information database 114m may further include an indication of whether the service can be (or is required to be) offered by providers within marketplace system 100 as an individual primary service or as a primary service of a bundled set of a plurality of services (for which a single payment for the bundled set of services will be disbursed to different provider for each of the services in the bundled set). In such embodiments, for each service for which the information record includes an indication that the service is offered as a primary service of a bundled set of services, various items of additional information relevant to the bundled set of services associated with the service that is indicated to be a primary service may be included in the respective information record for the primary service that is maintained within service pricing information database 114m.

Such items of information relevant to the bundled set of services included in the respective information record for a primary service within service pricing information database 114m may include, for example, items of information describing one or more secondary services associated with the primary service (such as name, a medical code number such as a CPT code identifying the service according to the nomenclature used by a formal medical classification system, and a secondary procedure identifier that is used by application server 116 to uniquely identify the particular secondary service in association with the unique procedure identifier for the primary service), one or more procedure or service identifiers for other services for which an information record is maintained within available services database 114g and/or service pricing information database 114m that are considered to be secondary services associated with the primary service, an indication of whether performance of each of the one or more secondary services is optional or required in association with performance of the primary service, an indication of whether the primary service is required to be performed at an outside facility, and, if the primary service is a procedure that is required to be performed at an outside facility, a medical code number identifying the use of the facility in association with the primary service according to the nomenclature used by a formal medical classification system (for example, an Ambulatory Payment Classification (APC) code for a service that is considered to be a facility outpatient service or a diagnosis related group (DRG) code for a service that is considered to be a facility inpatient service). In addition, in such embodiments, for each service for which the information record includes an indication that the service is offered as a primary service of a bundled set of services, the pricing information that is included in the respective information record for the primary service that is maintained within service pricing information database 114m can include respective pricing information for each of the primary service, the one or more secondary services, and, if required, the use of an outside facility for the primary service individually. In exemplary embodiments, the items of information relevant to the bundled set of services included in the respective information record for a primary service may further include an indication of whether each of one or more secondary services associated with the primary service is an anesthesia procedure or a pathology procedure.

As noted above, the information used to populate the information records within service pricing information database 114m can be compiled based on medical information and cost data sourced from a number of public and private healthcare information sources. In exemplary embodiments, the set of pricing information that is maintained for the primary service of each information record within service pricing information database 114m can be compiled based on data available from the Centers for Medicare & Medicaid Services (CMS) associated with the CMS's Resource-Based Relative Value Scale (RBRVS) and its underlying Relative Value Units (RVUs) and conversion factors (CFs) in conjunction with other reference sources, such as, for example, current versions of the AMA CPT book, HCPCS information, Medicare RBRVS, RBRVS Data Manager, and Medicare's National Correct Coding Initiative (NCCI), and similar resources.

For example, the information used to populate the set of pricing information included within the respective information record for each service that is maintained within service pricing information database 114m can be obtained from CMS standardized physician payment schedule data as determined by the RBRVS and the underlying RVUs and CFs that are associated with the CPT code and/or HCPCS code assigned to the service. In general, the CMS uses the RBRVS to measure the total amount of physician resources required to provide a specific physician service such that, in the RBRVS system, payments for services are determined by the resource costs needed to provide them. The total amount of physician resources is referred to as the service's "relative value" and is divided into three "relative value unit" (RVU) components: physician work, practice expense, and professional liability insurance. The RBRVS determines each service's work, practice expense and professional liability insurance RVUs. The physician work RVUs are updated each year to account for changes in medical practice and are determined based on factors that include the time it takes to perform the service; the technical skill, physical effort, mental effort, and judgment required to perform the service; and the stress on the physician resulting from the service's potential risk to the patient. The practice expense RVU measures physician resources used to provide a particular service, which can include expenses associated with the physician's use of nonclinical personnel to provide the service and expenses for office space, equipment, and supplies. In this regard, the value of the practice expense RVU component for a particular service will depend upon whether an outside facility would be used by the physician providing the service. For this reason, with respect to procedures that may require the use of an outside facility, the RBRVS provides both a facility practice expense RVU measure and a non-facility practice expense RVU measure for each of these procedures. In exemplary embodiments, for each such procedure for which the RBRVS provides both a facility practice expense RVU measure and a non-facility practice expense RVU measure, respective information records can be maintained for the service as a facility service and for the service as a non-facility service within service pricing information database 114m. The professional liability insurance RVU component is designed to reflect the cost of obtaining medical liability insurance. The relative value for a particular service is derived by summing the values of the three RVU components determined for the service, and a standard national rate for the service is then calculated by multiplying this combined relative value for the service by a conversion factor (a monetary amount that is determined and updated on a quarterly basis by the CMS and may vary between particular services or service categories, for example, in relation to CPT code ranges). In exemplary embodiments, the standard national rate derived in this manner for each service and the underlying RVUs and CFs that are associated with the CPT code and/or HCPCS code assigned to the service can be included in the set of pricing information of the respective information record for the service within service pricing information database 114m.

In the present exemplary embodiments, for use in conjunction with the physician service pricing information within service pricing information database 114m, a corresponding set of cost adjustment data can be compiled and maintained within cost adjustment information database 114n that can be applied to account for geographical variances in physician costs. The cost adjustment data can, for instance, be compiled from and/or determined based upon the Geographic Practice Cost Indices (GPCIs), which is used along with RVUs in Medicare Physician Fee Schedule (PFS) provided by CMS to determine allowable payment amounts for medical procedures in a manner that reflects geographical variations in practice cost. GPCIs are used to help standardize the differences in resource costs incurred in operating a private medical practice across geographic areas when those costs are compared with the national average costs for the physician work, practice expense, and malpractice insurance components of the fee schedule. More specifically, the CMS has established a GPCI for every Medicare payment locality for each of the three relative value unit components for a procedure (that is, the RVUs for work, practice expense, and malpractice), and the GPCIs are applied in the calculation of a fee schedule payment amount by multiplying the RVU for each component times the GPCI for that component. A listing of the current GPCI locality structure, including state, locality area (and when applicable, counties assigned to each locality area), and the corresponding GPCIs for each locality, can be obtained from the CMS website, and this information can be compiled and maintained within cost adjustment information database 114n by a back-end administrator of server system 110. In exemplary embodiments, a specific cost adjustment factor can be determined based on the GPCI information for each designated locality area and maintained within cost adjustment information database 114n. For example, a standard rate adjustment factor for each designated locality area can be determined by calculating an average (or any other suitable aggregate- or composite-based) factor by which the corresponding GPCIs for the locality impact the standard national rate derived for each service. As another example, such a standard rate adjustment factor for each designated locality area can be derived directly from the Geographic Adjustment Factor (GAF) that is determined for the locality by CMS. The GAF for each designated locality area is calculated as the weighted average of the three GPCIs, where the weights are the percentage of RVUs nationally made up by the PW, PE, and MP RVUs.

In another example, for each service for which the information record within service pricing information database 114m includes an indication that the service is offered as a primary service of a bundled set of services along with an indication that the primary service is required to be performed at an outside facility, the respective pricing information that is included in the information record for the use of the outside facility can be determined by whether the use of the outside facility is classified as a facility outpatient service or a facility inpatient service. For instance, for each facility outpatient service, the respective pricing information that is included in the information record for the use of the outside facility can be obtained from the APC price data that is maintained in association with CPT or HCPCS procedure codes by CMS. CMS assigns individual services classified according to HCPCS codes to APCs based on similar clinical characteristics and similar costs. Thus, APCs are essentially line-level fee schedules in which each HCPCS code for a service is assigned to one of hundreds of individual APCs, and for almost every APC, the fee is determined by multiplying a prospectively established scaled relative weight for the service's clinical APC by a conversion factor (CF) to arrive at a national unadjusted payment rate for the APC. National unadjusted payment rates for each HCPCS code for which separate payment is made that applies to the date of service can be compiled from the published addendums located at www.cms.gov/Medicare/Medicare-Fee-forService-Payment/HospitalOutpatientPPS/HospitalOutpatient-Regulations-and-Notices.html on the CMS website.

Accordingly, in exemplary embodiments, for each service for which a respective information record is maintained within service pricing information database 114m and a corresponding APC is provided by CMS, the corresponding national unadjusted payment rate for the facility outpatient service can be included in the set of pricing information of the respective information record for the service within service pricing information database 114m. In this regard, while the identification of such corresponding national unadjusted payment rates for services for which the respective information record within service pricing information database 114m includes a HCPCS medical code for identifying the service will be straightforward, identifying of such corresponding national unadjusted payment rates for services for which the respective information record within service pricing information database 114m includes another medical code number, such as a CPT code, for identifying the service will require an additional mapping step. For example, the particular national unadjusted payment rate for an facility outpatient service that is included in the pricing information of a respective information record maintained within service pricing information database 114m that includes a CPT code identifying the service may be determined by mapping the CPT code for the service to a corresponding HCPCS code, and then identifying the national unadjusted payment rate that corresponds to the mapped HCPCS code. For this purpose, in exemplary embodiments, for each service for which an information record is maintained within service pricing information database 114m, the items of information relevant to the service can further include a mapping between a CPT code identifier for the service and an HCPCS code identifier for the service. In exemplary embodiments, such mapping information can be determined and compiled within the information records of service pricing information database 114m by a back-end administrator of system 110.

In the present exemplary embodiment, for use in conjunction with the facility outpatient service pricing information within service pricing information database 114m discussed above, a corresponding set of cost adjustment data can be compiled and maintained within cost adjustment information database 114n that can be applied to account for geographic differences. The cost adjustment data for the facility outpatient service pricing information can, for instance, be compiled from and/or determined based upon the facility wage index that is maintained by the CMS. To account for geographic differences in input prices in determining allowable payment amounts for facility outpatient services, CMS further adjusts a labor portion of the national unadjusted payment rate (60 percent) by a facility wage index for the area where payment is being made (the remaining 40 percent non-labor portion is not adjusted). Presently, the wage index that is used by the CMS for this purpose is the inpatient prospective payment system (IPPS) wage index with all adjustments. In exemplary embodiments, the facility wage index information can be obtained from CMS and maintained within cost adjustment information database 114n.

In a similar manner, the respective pricing information that is included in information record for the use of the outside facility for each facility inpatient service can be obtained from the Medicare Severity-DRG (MS-DRG) price data that is maintained by CMS. Under the IPPS payment system for the operating costs of acute care hospital inpatient stays that is based on prospectively set rates, each case is categorized into a diagnosis-related group (DRG), which is a group of patients with similar clinical problems that are expected to require similar amounts of hospital resources, and whereby diagnoses and procedures assigned according to ICD-9-CM codes determine the MS-DRG assignment. Each DRG has a payment weight assigned to it that is based on the average resources used to treat Medicare patients in that DRG, and this payment weight is multiplied by an associated base payment rate that consists of a labor component and a non-labor component. These base payment rates, which are also known as standardized payment amounts for operating payments and the Federal rate for capital payments, are set by CMS for the operating and capital costs that efficient facilities would be expected to incur in furnishing covered inpatient services. Operating payments cover labor and supply costs. Capital payments cover costs for depreciation, interest, rent, and property-related insurance and taxes. The IPPS sets a national operating base rate and a national capital base rate each fiscal year.

As there is not a one-to-one match between MS-DRG assignment and CPT or HSPCS codes, compiling the facility inpatient service pricing information within service pricing information database 114m based on the MS-DRG price data requires an additional data mapping step. For example, the particular DRG payment rate information that is included in the respective pricing information of an information record for the use of the outside facility for each facility inpatient service may be determined by identifying the CPT code or HCPCS code for the services and then mapping the identified code for the service to a corresponding MS-DRG assignment. This mapping operation can be performed by a back-end administrator of system 110 based on information available from various sources, such as private insurance medical policy websites, coverage decision information available from CMS, published technology assessment reports, IPPS information available from CMS, and the like. In this regard, because there will not be a one-to-one correspondence between services identified by CPT or HCPCs codes and the MS-DRG assignments such that many services will correspond to multiple MS-DRG assignments, the facility inpatient service pricing information to be included in the respective information record for each such service within service pricing information database 114m can be derived from the price data for the multiple corresponding MS-DRG assignments. For example, the facility inpatient service pricing information included in the respective information record for such a service can be determined by calculating an average of the payment weights for the multiple corresponding MS-DRG assignments. In another example, the facility inpatient service pricing information included in the respective information record for such a service can be determined by simply selecting the lowest of the payment weights for the multiple corresponding MS-DRG assignments.

Upon such a mapping being performed for each service for which the information record within service pricing information database 114m includes an indication that the service is offered as a primary service of a bundled set of services along with an indication that the primary service is performed as a facility inpatient service, the DRG payment weight derived for the MS-DRG(s) mapped to the particular service, along with the current national operating base rate and a national capital base rate set by IPPS, can be included in the set of pricing information of the respective information record for the service within service pricing information database 114m.

In the present exemplary embodiment, for use in conjunction with the facility inpatient service pricing information within service pricing information database 114m discussed above, a corresponding set of cost adjustment data can be compiled and maintained within cost adjustment information database 114n that can be applied to account for geographic differences. Similar to the example discussed above with regard to the cost adjustment data for the facility outpatient service pricing information, the cost adjustment data for the facility inpatient service pricing information can, for instance, be compiled from and/or determined based upon the facility wage index that is maintained by the CMS. As noted above, in exemplary embodiments, the facility wage index information can be obtained from CMS and maintained within cost adjustment information database 114n.

In this regard, it should be noted that certain services for which the respective information record within service pricing information database 114m includes an indication that the service is offered as a primary service of a bundled set of services along with an indication that the primary service is required to be performed at an outside facility may facilitate a mapping of the use of the outside facility to both facility outpatient service price data and facility inpatient service price data. In exemplary embodiments, for such services, a back-end administrator of server system 110 can make a determination of which set of facility price data is more suitable to include in the set of pricing information of the information record. For example, such a determination may be based upon whether the particular service is more typically performed as a facility outpatient service or a facility inpatient service. In alternative exemplary embodiments, for each service for which the respective information record within service pricing information database 114*m* includes an indication that the service is offered as a primary service of a bundled set of services along with an indication that the primary service is required to be performed at an outside facility for which the use of the outside facility can be mapped to both facility outpatient service price data and facility inpatient service price data, respective information records can be maintained for the service as an outpatient facility service and for the service as an inpatient facility service within service pricing information database 114*m*.

In some exemplary embodiments, for each service for which the information record within service pricing information database 114*m* includes an indication that the service is offered as a primary service of a bundled set of services along with an indication that the primary service is required to be performed at an outside facility, the respective pricing information that is included in the information record for the use of the outside facility can include, in addition to or as an alternative to the facility pricing information discussed above, corresponding facility pricing information that is applicable for situations in which the use of the outside facility is classified as, rather than a facility outpatient service or a facility inpatient service, an Ambulatory Surgical Center (ASC) service. An ASC is a distinct type of facility entity that operates exclusively for the purpose of furnishing surgical services to patients who do not require hospitalization and in which the expected duration of services does not exceed 24 hours following admission.

In such exemplary embodiments, the respective pricing information that is included in each information record for which an indicated use of the outside facility may be provided as an ASC service, the respective pricing information that is included in the information record for the use of the outside facility as an ASC service can be obtained from the Ambulatory Surgical Center Fee Schedule (ASCFS) that is maintained by CMS, under which each procedure that is approved by CMS for payment as an ASC service is classified into one of nine payment groups based on their cost similarity (rather than clinical similarity). For most procedures covered under the ASC system, the payment rate is the product of a relative weight and an ASC conversion factor, which is set lower than the conversion factor that is used with respect to facility outpatient services, and CMS sets the national payment rate for each of the nine payment groups equal to an estimated median cost of procedures in that group. Accordingly, in exemplary embodiments, for each service for which a respective information record is maintained within service pricing information database 114*m* that includes an indication that the primary service is required to be performed at an outside facility and for which the primary service can be mapped to corresponding procedure that is approved by CMS for payment as an ASC service, the corresponding national payment rate for the payment group under which the ASC service is classified can be included in the set of pricing information of the respective information record for the service. As the CMS classifies procedures in the ASC system according to HCPCS codes, such a mapping can be implemented, for example, in a manner similar to that described above with reference to facility outpatient services to identify ASC national payment rates for corresponding services.

Additionally, in such exemplary embodiments, for use in conjunction with the ASC service pricing information within service pricing information database 114*m* discussed above, a corresponding set of cost adjustment data can be compiled and maintained within cost adjustment information database 114*n* that can be applied to account for geographic differences. The cost adjustment data for the ASC service pricing information can, for instance, be compiled, in a manner similar to the cost adjustment data for the facility outpatient service pricing information described above, from and/or determined based upon the ASC wage index information that is maintained by the CMS. To account for geographic differences in input prices in determining allowable payment amounts for ASC services, CMS further adjusts a labor portion of the national unadjusted payment rate (50 percent) by an ASC wage index for the area where payment is being made (the remaining 50 percent non-labor portion is not adjusted). Thus, in exemplary embodiments, the ASC wage index information can be obtained from CMS and maintained within cost adjustment information database 114*n*.

In another example, for each service for which the information record within service pricing information database 114*m* includes an indication that the service is offered as a primary service of a bundled set of services along with an indication that a secondary service associated with the primary service is an anesthesia procedure, the respective pricing information that is the anesthesia pricing information that is maintained by CMS. For this purpose, different types of services involving administration of anesthesia are assigned corresponding CPT codes, and each anesthesia code is assigned a base unit that reflects the difficulty of the procedure and inherent risks. For determining allowable payment amounts for anesthesia services, CMS utilizes the following formula: (Time Units+Base Units)×Conversion Factor=Anesthesia Fee Amount.

In this regard, anesthesia time is a continuous time period from the start of anesthesia to the end of an anesthesia service, and one time unit corresponds to a 15-minute interval, or fraction thereof, starting from the time the physician begins to prepare the patient for induction and ending when the patient may safely be placed under postoperative supervision and the physician is no longer in personal attendance. The conversion factors are listed by the CMS according to locality. Thus, the conversion factor in the formula listed above will correspond to the locality of the performing provider.

Accordingly, in exemplary embodiments, for each service for which the respective information record within service pricing information database 114*m* includes an indication that the service is offered as a primary service of a bundled set of services along with an indication that a secondary service associated with the primary service is an anesthesia procedure, corresponding anesthesia base rate information for the anesthesia service that is derived from the anesthesia pricing information maintained by CMS can be included in the set of pricing information of the respective information record for the service within service pricing information database 114*m*. For use in conjunction with the anesthesia service pricing information within service pricing information database 114*m*, the corresponding locality anesthesia conversion factors can be compiled and maintained within cost adjustment information database 114*n*. In this regard, it should be noted that while certain primary services will have associated anesthesia procedures that correspond to a specific anesthesia CPT code, other primary services may have associated procedures that correspond to multiple anesthesia CPT codes. Thus, for each service for which the respective information record within service pricing information database 114m includes an indication that a secondary service associated with the primary service is an anesthesia procedure for which a respective anesthesia CPT code is provided, the corresponding anesthesia base rate information for the anesthesia service to be included in the set of pricing information of the respective information record can be derived, for example, by multiplying the corresponding base unit assigned the anesthesia code by a typical or expected number of time units for performing the particular type of anesthesia procedure. Such a typical or expected number of time units can be determined, for example, by a back-end administrator of server system 110. For each service for which the respective information record within service pricing information database 114m includes an indication that a secondary service associated with the primary service is an anesthesia procedure for which there is not a one-to-one correspondence between the primary service and an anesthesia code assignment for the associated anesthesia procedure, the corresponding anesthesia base rate information for the anesthesia service to be included in the set of pricing information of the respective information record can be derived, for example, from the base rate for each of multiple corresponding anesthesia code assignments. For example, the corresponding anesthesia base rate information included in the respective information record for such a service can be determined by calculating an average of the base rates for the multiple corresponding anesthesia code assignments and then multiplying the calculated average base unit by a typical or expected number of time units for performing the particular type of anesthesia procedure. In another example, the corresponding anesthesia base rate information included in the respective information record for such a service can be determined by simply selecting the lowest of the base rates for the multiple corresponding anesthesia code assignments and then and then multiplying the selected lowest base unit by a typical or expected number of time units for performing the particular type of anesthesia procedure.

In another example, for each service for which the information record within service pricing information database 114m includes an indication that the service is offered as a primary service of a bundled set of services along with an indication that a secondary service associated with the primary service is a pathology procedure, the pricing information that is included in the respective information record for the pathology service can be obtained from the Clinical Laboratory Fee Schedule (CLFS) maintained by CMS in association with the CPT coding for surgical pathology. More specifically, in exemplary embodiments, for each service for which the information record includes an indication that a secondary service associated with the primary service is a pathology procedure, the corresponding CPT code can be identified for the pathology service, and the laboratory fee that corresponds to the identified CPT code can be identified from the CLFS and included as a pathology rate in the set of pricing information of the respective information record for the service within service pricing information database 114m.

As described above, healthcare marketplace system 100 is implemented as a client/server system that includes central server system 110, which is commonly accessed by each user of the system through operation of any of client systems 140 that are operatively coupled to the central server system via a communication network 150. Each client system 140 is a user terminal or other client device implementing software for and running a respective client application 142 for accessing services provided via a network-based application (also referred to herein as a network service) implemented by application server 116, and application server 116 can implement a user interface on the client application within which the client application renders the information served by the application server so that users of connected client systems 140 can access various services provided by the application server with relative ease by operating a corresponding client application 142. In exemplary embodiments, the user interface can be a web-based user interface, implemented as a web-based software application hosting a corresponding website that provides a number of web pages (that is, screens) to offer the services implemented by application server 116 to users. For example, a user can access the corresponding website and, thereby, the services provided by the application server using a web browser implemented within a client application 142 executing on a client system 142.

In exemplary embodiments, to access the functionality provided by pricing tool 137, a provider user, upon registering a provider account with server system 110 (for example, a physician, practice group, or hospital system account) to establish an account information record within the corresponding profile database maintained within data store 114 and logging into his or her physician account, the user may be directed to a provider account page implemented by provider portal 130 that provides a set of user interface controls that can be accessed by the user to access functionality provided by procedure management service 133 to offer healthcare services for purchase by customer users registered with the system. As noted above, in the present exemplary embodiment, the accessible functionality provided by procedure management service 133 in this regard includes the functionality provided by pricing tool 137.

In particular, upon the provider user indicating an intention to utilize pricing tool in conjunction with offering healthcare services for purchase via server system 110 (for example, by selecting a "Service Pricing Tool" tab within the provider account page implemented by provider portal 130), the user will be directed to an interactive service pricing page with information that is generated based on the information maintained in the respective information record for the provider within the corresponding profile database maintained within data store 114 and the respective information records for healthcare services that are maintained in service pricing information database 114m. Price setting tool 137 may be configured, for example, to implement the interactive service pricing page to provide the provider user with detailed pricing information and recommended rates for services that may be offered by the provider for purchase via server system 110, as well as various user interface controls accessible by the user to perform adjustments to the recommended rates as desired.

FIG. 7A is a screen shot illustrating a first example of a graphical user interface provided by such a service pricing page 700 for a user accessing provider portal 130 in association with a registered hospital system account. In the example illustrated in FIG. 7A, the user interface provided at service pricing page 700 includes a medical specialty drop-down menu 702, a locality adjustment section 704, a recommended rate adjustment section 706, a detailed pricing information section 708, and a set of selectable buttons 710a ("Email Prices"), 710b ("Save Changes"), and 710c ("Take Live"), the use of which will be described in greater detail below. Drop-down menu 702 provides a list of selectable medical specialties (for example, orthopedics, general surgery, cardiac imaging, etc.), and pricing tool is implemented to, in response to the user selecting a particular medical specialty using drop-down menu 702, configure the user interface options and populate the information displayed within locality adjustment section 704, recommended rate adjustment section 706, and detailed pricing information section 708 in accordance with the selected medical specialty and further based on information maintained in the respective information record for the provider that is maintained within hospital system profile database 114d, information that is maintained in the respective information records for each service indicated as being commonly associated with the selected medical specialty within service pricing information database 114m, and information maintained within cost adjustment information database 114n, which, as discussed above, can be accessed by pricing tool 137 via database services provided at a front end by database server 112.

For instance, in the example screen shot illustrated in FIG. 7A, the user has selected "Radiology" from medical specialty drop-down menu 702, and pricing tool 137 has, in response to this selection, configured the user interface options and populated the information displayed within locality adjustment section 704, recommended rate adjustment section 706, and detailed pricing information section 708 in accordance with the selection of "Radiology" from drop-down menu 702. More specifically, as shown in FIG. 7A, locality adjustment section 704 has been configured to include a physician locality section and a facility section in response to the for making pricing adjustments based on the locality of a physician that is affiliated with the hospital system and would be performing the radiology services being priced. The facility section is included within locality adjustment section 704 in response to pricing tool 137 recognizing that the respective information records for services indicated as being commonly associated with the selected medical specialty of radiology within service pricing information database 114m include information records having an indication that the service is a primary service of a bundled set of services that is required to be performed at an outside facility and is provided for making pricing adjustments based on the facility that is affiliated with the hospital system at which the radiology services being priced would be performed.

In the present example, the physician locality section includes a physician location field 704a and a physician location rate field 704b, and the facility section includes a facility field 704c and a facility rate field 704d. The physician location field 704a is for receiving and displaying an entry specifying the location of a physician that would be performing the services indicated as being commonly associated with the selected medical specialty of radiology within service pricing information database 114m, and the physician location rate field 704b is configured to provide a rate adjustment factor for the pricing information included in detailed pricing information section 708 for the services indicated as being commonly associated with radiology. In exemplary embodiments, pricing tool 137 can be configured to derive an initial physician location entry based on the location associated with physician affiliation(s) included in hospital system profile database 114d and include this derived physician location entry as a default value within physician location field 704a. Physician location rate field 704b is provided for receiving and displaying a geographic adjustment rate for physician services that, by default, is derived based on information maintained in cost adjustment information database 114n and provided by pricing tool 137 in correspondence with the physician location entry that is currently specified within physician location field 704a. More particularly, in exemplary embodiments, pricing tool 137 can be configured to access the physician rate cost adjustment data in cost adjustment information database 114n that corresponds to the physician location entry that is currently specified within physician location field 704a (for example, a standard rate adjustment factor determined for a designated locality area that encompasses the specified physician location entry) and derive a corresponding geographic adjustment rate that is displayed as a default value within physician location rate field 704b.

In the present example, pricing tool 137 is further configured to allow the provider user accessing service pricing page 700 to proceed to enter text corresponding to a desired location of the physician that would perform the services associated with the selected medical specialty within physician location field 704a. In this regard, pricing tool 137 may be configured to require that the text entered by the user in physician location field 704a correspond to a particular locality area for which corresponding physician rate adjustments are maintained in cost adjustment information database 114n. In exemplary embodiments, pricing tool 137 can be configured to, in response to the provider user accessing physician location field 704a to specify a particular physician location, provide a list of suggested physician locations that correspond to designated locality areas for which cost adjustment data is maintained in cost adjustment information database 114n and are determined to be similar to the text being entered by the user in physician location field 704a from which the user can select a desired value for the location of the physician that would be performed the services associated with the medical specialty selected from drop-down menu 702. The list of suggested physician locations provided by pricing tool 137 can further include an option for the user to select a standard, national physician rate rather than a particular geographic location. In response to a specification of a new physician location within physician location field 704a, pricing tool 137 can be configured to dynamically access the physician rate cost adjustment data in cost adjustment information database 114n that corresponds to the newly-specified physician location entry that is currently specified within physician location field 704a and derive a corresponding geographic adjustment rate that is displayed as the current value within physician location rate field 704b. In the present example, pricing tool 137 is also configured to allow the provider user to directly access physician location rate field 704b and specify a desired value for the geographic adjustment rate that will override the particular geographic adjustment rate that is derived by pricing tool 137 based on the physician location entry within physician location field 704a and displayed as the current value within physician location rate field 704b. The effect of such an entry being submitted within physician rate field 704b will be described below with reference to detailed pricing information section 708.

Similarly, with reference to the facility section of locality adjustment section 704 in the present example, facility field 704c is for receiving and displaying an entry specifying the name of a particular outside facility that would be used to perform services that are indicated as being commonly associated with the selected medical specialty of radiology and as being a primary service of a bundled set of services that is required to be performed at an outside facility within service pricing information database 114*m*, and the facility rate field 704*d* is configured to provide a rate adjustment factor for the pricing information included in detailed pricing information section 708 for the facility fee for services indicated as being commonly associated with radiology. In exemplary embodiments, pricing tool 137 can be configured to derive an initial outside facility entry based on the facility affiliation(s) included the respective information record for the hospital system account in hospital system profile database 114*d* being used to access the pricing tool 137 functionality via provider portal 130 and include this derived facility entry as a default value within facility field 704*c*. Facility rate field 704*d* is provided for receiving and displaying an adjustment rate for facility services that, by default, is derived and provided by pricing tool 137 in correspondence with the characteristics of the facility that is currently specified as the entry within facility field 704*c*. In exemplary embodiments, pricing tool 137 can be configured to retrieve the characteristic information for the facility that is currently specified as the entry within facility field 704*c* from the information included for affiliated facilities within the respective information record for the hospital system account within hospital system profile database 114*d*, and pricing tool 137 can be configured to access the cost adjustment data pertaining to facility services in cost adjustment information database 114*n* corresponding to the characteristics of the facility that is currently specified as the entry within facility field 704*c* and apply to the corresponding facility cost adjustment data to derive a corresponding facility adjustment rate that is displayed as a default value within facility rate field 704*d*.

In the present example, pricing tool 137 is further configured to allow the provider user accessing service pricing page 700 to proceed to enter text corresponding to a name of a desired outside facility at which the services associated with the selected medical specialty would be performed within facility field 704*c*. In this regard, pricing tool 137 may be configured to require that the text entered by the user in facility field 704*c* correspond to the name of a particular facility specified in the facility affiliations included the respective information record for the hospital system account in hospital system profile database 114*d* being used to access the pricing tool 137 functionality via provider portal 130. In exemplary embodiments, pricing tool 137 can be configured to, in response to the provider user accessing facility field 704*c* to specify a particular facility name, provide a list of names of suggested facilities that are determined to be similar to the text being entered by the user in facility field 704*c* from which the user can select a desired value for the name of the facility at which the services associated with the medical specialty selected from drop-down menu 702 would be performed. The list of suggested facility names provided by pricing tool 137 can further include an option for the user to select a standard, national facility rate rather than an adjustment rate for a particular facility. In response to a specification of a new facility within facility field 704*c*, pricing tool 137 can be configured to dynamically access the cost adjustment data pertaining to facility services in cost adjustment information database 114*n* corresponding to the characteristics retrieved from the information included for affiliated facilities within the respective information record for the hospital system account within hospital system profile database 114*d* for the newly-specified facility entry within facility field 704*c* and apply to the corresponding facility cost adjustment data to derive a corresponding facility adjustment rate that is displayed as the current value within facility rate field 704*d*. In the present example, pricing tool 137 is also configured to allow the provider user to directly access facility rate field 704*d* and specify a desired value for the facility adjustment rate that will override the particular facility adjustment rate that is derived by pricing tool 137 based on the facility entry within facility field 704*c* and displayed as the current value within facility rate field 704*d*. The effect of such an entry being submitted within facility rate field 704*d* will be described below with reference to detailed pricing information section 708.

With continued reference to the example screen shot illustrated in FIG. 7A, pricing tool 137 has, in response to the user selection "Radiology" from medical specialty drop-down menu 702, configured the user interface options and populated the information displayed within rate adjustment section 706. More specifically, as shown in FIG. 7A, rate adjustment section 706 has been configured to include a physician rate adjustment field 706*a* and a facility rate adjustment field 706*b* in response to the selection of "Radiology" from drop-down menu 702. Physician rate adjustment field 706*a* is provided for making a general pricing adjustment to the pricing information included in detailed pricing information section 708 for physician fees for the services indicated as being commonly associated with radiology as desired by the provider user that may be based on any budgetary considerations specific to the provider and/or physician. Facility rate adjustment field 706*b* is included within rate adjustment section 706 in response to pricing tool 137 recognizing that the respective information records for services indicated as being commonly associated with the selected medical specialty of radiology within service pricing information database 114*m* include information records having an indication that the service is a primary service of a bundled set of services that is required to be performed at an outside facility and is provided for making a general pricing adjustment to the pricing information included in detailed pricing information section 708 for physician fees for the services indicated as being commonly associated with radiology as desired by the provider user that may be based on any budgetary considerations specific to the provider and/or facility.

More specifically, physician rate adjustment field 706*a* is provided to allow the provider user accessing the functionality provided by pricing tool 137 via provider portal 130 to enter a percentage value by which physician fees listed in detailed pricing information section for the services indicated as being commonly associated with radiology will be multiplied, and facility rate adjustment field 706*b* is likewise provided to allow the provider user to enter a percentage value by which outside facility fees listed in detailed pricing information section for the services indicated as being commonly associated with radiology will be multiplied. In exemplary embodiments, pricing tool 137 can be configured to initially specify and display default percentage values within physician rate adjustment field 706*a* and facility rate adjustment field 706*b*, which may be determined and set by a back end administrator of server system 110 based on budgetary considerations for typical providers. Such default percentages values can be used in the initial calculations used to generate the initial pricing information that is displayed in detailed pricing information section 708 for physician fees and outside facility fees for the services indicated as being commonly associated with radiology. Pricing tool 137 can be further configured to, in response to each instance of the provider user accessing rate adjustment section 706 to enter new percentage values within physician rate adjustment field 706*a* or facility rate adjustment field 706*b*, re-calculate and update the pricing information for physician fees and outside facility fees that is displayed in detailed pricing information section 708 for the services indicated as being commonly associated with radiology.

With continued reference to the example screen shot illustrated in FIG. 7A, as noted above, pricing tool 137 has, in response to the user selection "Radiology" from medical specialty drop-down menu 702, configured the user interface options and populated the information displayed within detailed pricing information section 708. In general, as shown in FIG. 7A, detailed pricing information section 708 is generated by pricing tool 137 as a table with various interactive user interface controls that includes a procedure column 711, a facility price column 712, a physician price column 713, an additional fee column 714, and a total amount column 715.

The information in procedure column 711 is generated by pricing tool 137 to include a row entry for each procedure category listed in the respective information records for services that are maintained in service pricing information database 114*m* and include an indication that the service is commonly associated with the medical specialty selected via drop-down menu 702, which is "Radiology" for the example screen shot depicted in FIG. 7A. For instance, the procedure categories listed in procedure column 711 in the present example include "Bone Density DXA Extremity" radiology procedures, "Bone Density DXA Scan" radiology procedures, and "Videofluoroscopic Swallowing Study" radiology procedures. As further illustrated in FIG. 7A for the example of the "Bone Density DXA Extremity" radiology procedures listing in procedure column 711, detailed pricing information section 708 is implemented to include user interface elements that are accessible by the user to expand the information listed for each procedure category to display information pertaining to the specific services for which the respective information records maintained in service pricing information database 114*m* indicate the service is categorized under that procedure category, as well as corresponding user interface elements that are accessible by the user to collapse any set of information listed for a procedure category that has been expanded in the user interface.

In the present example, the expanded information for the "Bone Density DXA Extremity" radiology procedures listing includes row entries for a "Dxa bone density/peripheral" service and a "Fracture assessment via dxa" service. As further illustrated in FIG. 7A, the expanded information for a particular procedure category further includes, for each service categorized as a sub-procedure of the procedure category, a medical code number used to identify the service (for example, a CPT code), a base facility rate, a base physician rate, an adjusted facility rate, and an adjusted physician rate. The base physician rate for each service listed in the expanded display is obtained by pricing tool 137 from standard national physician rate derived for the service as described above that is stored within the respective information record maintained for the service within service pricing information database 114*m* for display within detailed pricing information section 708, and the adjusted physician rate for each service listed in the expanded display is calculated by pricing tool 137 for display within detailed pricing information section 708 by multiplying the corresponding base physician rate by both the current value that is specified in physician location rate field 704*b* of locality adjustment section 704 and the current percentage value that is specified in physician rate adjustment field 706*a* of recommended rate adjustment section 706. Likewise, the base facility rate for each service listed in the expanded display is obtained by pricing tool 137 from the national or otherwise derived base facility rates for the use of an outside facility in conjunction with the service that is stored within the respective information record maintained for the service within service pricing information database 114*m* for display within detailed pricing information section 708, and the adjusted facility rate for each service listed in the expanded display is calculated by pricing tool 137 for display within detailed pricing information section 708 by multiplying the corresponding base facility rate by both the current value that is specified in facility location rate field 704*d* of locality adjustment section 704 and the current percentage value that is specified in facility rate adjustment field 706*b* of recommended rate adjustment section 706.

In the present example, as further illustrated in FIG. 7A, the expanded information for a particular procedure category further includes a physician price field 711*a* that specifies a price that will be set by the provider user for each of the services that have been categorized under the expanded procedure category and a facility price field 711*b* that specifies a price that will be applied by the provider user for the use of an outside facility for each of the services that have been categorized under the expanded procedure category. By providing a mechanism that enables the user to determine and utilize the same pricing values for each of the services that have been categorized under the same procedure category, pricing tool 137 can simplify the task of setting a fee schedule for a provider.

In exemplary embodiments, pricing tool 137 can be configured to derive and include initial, default price values within physician price field 711*a* and physician price field 711*a*. For example, pricing tool 137 can derive and set the default price value within physician price field 711*a* as the average of the adjusted physician rates for all services listed in the expanded display for a procedure category. Likewise, pricing tool 137 can derive and set the default price value within facility price field 711*b* as the average of the adjusted facility rates for all services listed in the expanded display for a procedure category. In exemplary embodiments, pricing tool 137 can be configured to provide an option via user interface controls for the user to select a particular method from a list of methods that can be employed by pricing tool 137 to derive and set the price values within each of physician price field 711*a* and facility price field 711*b*. For example, pricing tool 137 can be configured to enable the user select between using the average of the corresponding adjusted rates for all services listed in the expanded display for a procedure category for the price values within each of physician price field 711*a* and facility price field 711*b* or the highest of the corresponding adjusted rates for all services listed in the expanded display for a procedure category for the price values within each of physician price field 711*a* and facility price field 711*b*. A provider user may, for instance, be inclined to select the option to use the highest of the corresponding adjusted rates for all services listed in the expanded display for a procedure category for the price values within physician price field 711*a* or facility price field 711*b*, rather than the average, where the provider only offers services under that procedure category for which corresponding adjusted rates are on the higher end of the spectrum for the procedure category or where the provider expects that a majority of purchases of the services listed in the expanded display for that procedure category will be for the services for which corresponding adjusted rates are on the higher end of the spectrum for the procedure category. In exemplary embodiments, pricing tool 137 can be further configured to allow the provider user accessing service pricing page 700 to access each of physician price field 711a and facility price field 711b to input particular price values within these fields. For instance, based on a review of the pricing information provided within detailed pricing information section 708 for the services listed in the expanded display for a procedure category, a provider user may determine that, based on expected purchases of the services listed in the expanded display for that procedure category, certain price values will be more representative of the costs for providing the services listed in the expanded display.

As further indicated in the example screen shot illustrated in FIG. 7A, the row entry for a particular procedure category will include a pricing value under physician price column 713 that corresponds to the pricing value that is specified within physician price field 711a in the expanded display for the procedure category, and, likewise, the row entry for a particular procedure category will include a pricing value under facility price column 712 that corresponds to the pricing value that is specified within facility price field 711b in the expanded display for the procedure category. In this regard, pricing tool 137 can be configured to dynamically update the pricing values provided under physician price column 713 and facility price column 712 in response to changes to the price values within physician price field 711a and facility price field 711b respectively. As discussed above, in exemplary configurations of pricing tool 137, such changes to the price values within physician price field 711a and facility price field 711b in the expanded display for a particular procedure category may occur in response to changes to any of the current values that are specified in physician location rate field 704b and facility location rate field 704d of locality adjustment section 704, the current percentage values that are specified in physician rate adjustment field 706a and facility rate adjustment field 706b of recommended rate adjustment section 706, changes in the particular method employed by pricing tool 137 to derive and set the price values within each of physician price field 711a and facility price field 711b, and direct entries of particular price values by a provider user within physician price field 711a and facility price field 711b.

In exemplary embodiments, the row entry for a particular procedure category can include a pricing value under additional fee column 714 that lists an additional fee amount that would be included in the price for offering any service listed in the expanded display for a procedure category for purchase via marketplace system 100. For example, such a fee may correspond to a negotiated or contracted commission fee for offering a service for purchase via the system (for example, a fixed percentage of the price for a service and/or a flat fee). As further illustrated in FIG. 7A, the row entry for a particular procedure category can include a pricing value under total amount column 715 that is provided as a sum of the price values listed under facility price column 712, physician price column 713, and, if included, additional fee column 714 in the row entry for a particular procedure category. This represents the actual price at which each service listed in the expanded display for a procedure category would be offered for purchase via marketplace system 100 as a bundled set of services from the provider user accessing service pricing page 700 via provider portal 130.

In some exemplary embodiments, pricing tool 137 can be further configured to provide an option via user interface controls implemented within service pricing page 700 for a provider user that is accessing the service pricing page and has selected a medical specialty from drop-down menu 702 for which pricing tool 137 recognizes that the respective information records for services indicated as being commonly associated with the selected medical specialty within service pricing information database 114m include information records having an indication that the service is a primary service of a bundled set of services that is required to be performed at an outside facility to specify that the pricing information for the use of the outside facility included in service pricing page 700 should be populated based on the ASC pricing information maintained within service pricing information database 114m and cost adjustment information database 114n. For example, pricing tool 137 can be configured to, in response to a provider user making such a specification within service pricing page 700, such as by specifying a new facility within facility field 704c that is an ASC, dynamically repopulate the information displayed within locality adjustment section 704, recommended rate adjustment section 706, and detailed pricing information section 708 based on the ASC pricing information maintained within service pricing information database 114m and information maintained within cost adjustment information database 114n that corresponds to the location of the newly-specified ASC facility.

In exemplary embodiments, pricing tool 137 can be further configured to provide an option via user interface controls implemented within detailed pricing information section 708 for a provider user accessing service pricing page 700 to review and determine pricing for offering services via marketplace system 100 for a particular medical specialty selected from drop-down menu 702 to delete certain procedure categories and particular procedures from the detailed pricing information section of the service pricing page interface. Such an option may be useful for a provider user, for example, when the provider user is not planning to any of the services listed in the expanded display for a particular procedure category or any specific services that are listed as sub-procedures in the expanded display for a particular procedure category for purchase via marketplace system 100. In such exemplary embodiments, pricing tool 137 can be further configured to provide an option via user interface controls to review any procedure categories deleted by the provider user and reset detailed pricing information section 708 to revert to listing any deleted procedure categories.

As noted above and further illustrated in FIG. 7A, the user interface provided at service pricing page 700 in the present example also includes a set of accessible user interface controls 710a ("Email Prices"), 710b ("Save Changes"), and 710c ("Take Live"). For purposes of the present example, these user interface controls are provided within service pricing page 700 as selectable buttons. In the present exemplary embodiment, pricing tool 137 can be configured to, in response to a provider user selecting "Save Changes" button 710b, generate an information record that includes indications of all of the information currently specified within each of the various fields included within service pricing page 700 and each of the various options currently selected by the provider user within user interface of the service pricing page for the particular medical specialty selected by the user from drop-down menu 702 and store this generated information record within or otherwise in association with the respective account information record maintained within the corresponding profile database of data store 114 for the provider account in association with which the provider user is conducting the present session with provider portal 130 to access functionality provided by the pricing tool via the service pricing page. Upon such a corresponding information record being generated and stored by pricing tool 137 for the provider user in this manner and the provider user navigating away from service pricing page 700 or logging out of the provider account being used to access services provided by application server 116 via provider portal 130 in association with the respective account information record maintained within the corresponding profile database of data store 114 for the provider account, pricing tool 137 can be configured to, in response to the next time the provider user is logged in to the provider account, accesses the functionality provided by pricing tool 137 via the service pricing page, and selects the same particular medical specialty via drop-down menu 702, retrieve the information record that was stored in association with the respective account information record maintained within the corresponding profile database of data store 114 for the provider account and configure the initial information specified within each of the various fields included within and the initial settings for the service pricing page in accordance with the information included within this document when rendering the service pricing page.

In the present exemplary embodiment, pricing tool 137 can be configured to, in response to a provider user selecting "Email Prices" button 710a, provide user interface controls for allowing the user to specify an email address and send an electronic document that includes indications of the pricing information currently displayed within detailed pricing information section 708 of service pricing page 700 for the particular medical specialty presented selected by the user from drop-down menu 702 to the specified email address. Pricing tool 137 can be configured to, in response to the provider user specifying an email address and selecting the option to send a corresponding document via these user interface controls, generate such an electronic document (such as, for example, a Microsoft Excel document) and send the generated document to the specified email address. A provider user may wish to utilize this functionality, for example, to send the information currently displayed within detailed pricing information section 708 of service pricing page 700 to an email address utilized by the provider user or in association with the provider account for subsequently performing a review of this information without logging in to the provider account being used to access services provided by application server 116 via provider portal 130 or, alternatively, to send the information included in the document generated by pricing tool 137 to an email address utilized by a physician that would be performing services currently displayed within detailed pricing information section 708 of service pricing page 700 or an outside facility that would be used for performing such services for informational purposes and/or for approval of the relevant pricing information.

Finally, with reference to the present example, pricing tool 137 can be configured to, in response to a provider user selecting "Take Live" button 710c, automatically initiate, on behalf of the provider user, a service offering with procedure management service 133 to offer each of the services currently included within detailed pricing information section 708 of service pricing page 700 for the particular medical specialty presented selected by the user from drop-down menu 702 for purchase via server system 110 and establish the respective information record for the offered service within service offer database 114h in accordance with the information currently specified within the service pricing page for the service and any associated information maintained within data store 114 (such as, for example, the unique procedure identifier for the information record within available services database 114g for the service, the unique account identifier for the account information record within physician profile database 114b for the physician user will perform the service, a location at which the service will be performed, the unique account identifier for the account information record within the corresponding profile database 114d of the provider for which payment for the service when purchased through the system is to be directed, a price for purchasing the service within marketplace system 100, etc.). In this manner, pricing tool 137 can provide a mechanism for a provider to offer a large number of services for purchase via marketplace system 100 by customer users registered with the system without having to perform full set of operations described above for accessing functionality provided by procedure management service 133 to offer each of the services individually.

FIG. 7B is a screen shot illustrating a second example of a graphical user interface provided by service pricing page 700 for a user accessing provider portal 130 in association with a registered hospital system account. In the example illustrated in FIG. 7B, the user has selected "General Surgery" from medical specialty drop-down menu 702, and pricing tool 137 has, in response to this selection, configured the user interface options and populated the information displayed within locality adjustment section 704, rate adjustment section 706, and detailed pricing information section 708 in accordance with the selection of "General Surgery" from drop-down menu 702. More specifically, as shown in FIG. 7B, locality adjustment section 704 has been configured to include, in addition to the physician locality section and the facility section described above with reference to the example illustrated in FIG. 7C, an anesthesia locality section in response to the selection of "General Surgery" from drop-down menu 702. The anesthesia locality section is included within locality adjustment section 704 in response to pricing tool 137 recognizing that the respective information records for services indicated as being commonly associated with the selected medical specialty of general surgery within service pricing information database 114m include information records having an indication that the service is a primary service of a bundled set of services for which a secondary service associated with the primary service in the bundled set is an anesthesia procedure and is provided for making pricing adjustments based on the locality at which the general surgery services being priced (and, thus, the associated anesthesia procedure) would be performed.

In the present example, the anesthesia locality section includes an anesthesia location field 704e and an anesthesia location rate field 704f. The anesthesia location field 704e is for receiving and displaying an entry specifying the location at which the services indicated as being commonly associated with the selected medical specialty of general surgery within service pricing information database 114m would be performed, and the anesthesia location rate field 704f is configured to provide a rate adjustment factor for the pricing information included in detailed pricing information section 708 for the services indicated as being commonly associated with radiology. In exemplary embodiments, pricing tool 137 can be configured to derive an initial anesthesia location entry based on the location associated with physician affiliation(s) included in hospital system profile database 114d and include this derived physician location entry as a default value within anesthesia location field 704e. In other exemplary embodiments, and in the example screen shot illustrated in FIG. 7B, pricing tool 137 can be configured to specify that a standard, national anesthesia rate is being used as a default value within anesthesia location field 704*e* rather than a particular geographic location. Anesthesia location rate field 704*f* is provided for receiving and displaying a geographic adjustment rate for physician services that, by default, is derived and provided by pricing tool 137 in correspondence with the anesthesia location entry that is currently specified within anesthesia location field 704*e*. More particularly, in exemplary embodiments, pricing tool 137 can be configured to access the information pertaining to anesthesia rate adjustments in service pricing information database 114*n* corresponding to the anesthesia location entry that is currently specified within anesthesia location field 704*e* and derive a corresponding geographic adjustment rate that is displayed as a default value within anesthesia location rate field 704*e*. The corresponding geographic adjustment rate can be derived, for example, based on a ratio of the CMS anesthesia conversion factor to a standard, national anesthesia conversion factor.

In the present example, pricing tool 137 is further configured to allow the provider user accessing service pricing page 700 to proceed to enter text corresponding to a desired location within anesthesia location field 704*e* at which the services associated with the selected medical specialty would be performed. In this regard, pricing tool 137 may be configured to require that the text entered by the user in within anesthesia location field 704*e* correspond to a particular locality area for which corresponding anesthesia rate adjustments are maintained in cost adjustment information database 114*n*. In exemplary embodiments, pricing tool 137 can be configured to, in response to the provider user accessing within anesthesia location field 704*e* to specify a particular physician location, provide a list of suggested locations that correspond to designated locality areas for which anesthesia cost adjustment data is maintained in cost adjustment information database 114*n* and are determined to be similar to the text being entered by the user in anesthesia location field 704*e* from which the user can select a desired value for the location at which the services associated with the medical specialty selected from drop-down menu 702 would be performed. The list of suggested anesthesia locations provided by pricing tool 137 can further include an option for the user to select a standard, national anesthesia adjustment rate rather than a particular geographic location, which pricing can be configured to recognize as corresponding to a standard, national anesthesia conversion factor. In response to a specification of a new location within anesthesia location field 704*e*, pricing tool 137 can be configured to dynamically access the information pertaining to physician rate adjustments in geographic factors database 114*n* corresponding to the newly-specified physician location entry within anesthesia location field 704*e* and derive a corresponding geographic adjustment rate that is displayed as the current value within anesthesia location rate field 704*f*. In the present example, pricing tool 137 is also configured to allow the provider user to directly access anesthesia location rate field 704*f* and specify a desired value for the geographic adjustment rate that will override the particular geographic adjustment rate that is derived by pricing tool 137 based on the location entry within anesthesia location field 704*e* and displayed as the current value within anesthesia location rate field 704*f*. The effect of such an entry being submitted within anesthesia rate field 704*f* will be described below with reference to detailed pricing information section 708.

With continued reference to the example screen shot illustrated in FIG. 7B, as noted above, pricing tool 137 has, in response to the user selection "General Surgery" from medical specialty drop-down menu 702, configured the user interface options and populated the information displayed within rate adjustment section 706. More specifically, as shown in FIG. 7B, rate adjustment section 706 has been configured to include, in addition to a physician rate adjustment field 706*a* and a facility rate adjustment field 706*b* as described above with reference to the example screen shot shown in FIG. 7A, an anesthesia rate adjustment field 706*c* in response to the selection of "Radiology" from drop-down menu 702. Anesthesia rate adjustment field 706*c* is included within rate adjustment section 706 in response to pricing tool 137 recognizing that the respective information records for services indicated as being commonly associated with the selected medical specialty of general surgery within service pricing information database 114*m* include information records having an indication that the service is a primary service of a bundled set of services for which a secondary service associated with the primary service in the bundled set is an anesthesia procedure and is provided for making a general pricing adjustment to the pricing information included in detailed pricing information section 708 for anesthesia fees for the services indicated as being commonly associated with general surgery as desired by the provider user that may be based on any budgetary considerations specific to the provider or physician.

More specifically, anesthesia rate adjustment field 706*c* is provided to allow the provider user accessing the functionality provided by pricing tool 137 via provider portal 130 to enter a percentage value by which anesthesia fees listed in detailed pricing information section 708 for the services indicated as being commonly associated with general surgery will be multiplied. In exemplary embodiments, pricing tool 137 can be configured to initially specify and display a default percentage value within anesthesia rate adjustment field 706*c*, which may be determined and set by a back end administrator of server system 110 based on budgetary considerations for typical providers. Such a default percentages value can be used in the initial calculations used to generate the initial pricing information that is displayed in detailed pricing information section 708 for anesthesia fees for the services indicated as being commonly associated with general surgery. Pricing tool 137 can be further configured to, in response to each instance of the provider user accessing rate adjustment section 706 to enter a new percentage value within anesthesia rate adjustment field 706*c*, re-calculate and update the pricing information for anesthesia fees that is displayed in detailed pricing information section 708 for the services indicated as being commonly associated with general surgery.

With continued reference to the example screen shot illustrated in FIG. 7B, as noted above, pricing tool 137 has, in response to the user selection "General Surgery" from medical specialty drop-down menu 702, configured the user interface options and populated the information displayed within detailed pricing information section 708. In general, as shown in FIG. 7B, detailed pricing information section 708 is generated by pricing tool 137 as a table with various interactive user interface controls that includes, in addition to procedure column 711, facility price column 712, physician price column 713, additional fee column 714, and total amount column 715, an anesthesia price column 716. As illustrated in FIG. 7B, the expanded information for a particular procedure category further includes, for each service categorized as a sub-procedure of the procedure category, in addition to a medical code number used to identify the service, a base facility rate, a base physician rate, an adjusted facility rate, and an adjusted physician rate as described above with reference to FIG. 7A, a base anesthesia rate and an adjusted anesthesia rate. In exemplary embodiments, the base anesthesia rate for each service listed in the expanded display can be derived by pricing tool 137 for display within detailed pricing information section 708 by accessing service pricing information to obtain the corresponding anesthesia base rate, accessing cost adjustment information database 114m to obtain a standard, national anesthesia conversion factor, and multiplying the obtained anesthesia base rate by the obtained national anesthesia conversion factor, and the adjusted anesthesia rate for each service listed in the expanded display is calculated by pricing tool 137 for display within detailed pricing information section 708 by multiplying the corresponding base anesthesia rate for the service listed in the expanded display by both the current value that is specified in anesthesia location rate field 704e of locality adjustment section 704 and the current percentage value that is specified in anesthesia rate adjustment field 706f of recommended rate adjustment section 706.

In the present example, as further illustrated in FIG. 7B, the expanded information for a particular procedure category further includes, in addition to physician price field 711a and facility price field 711b, an anesthesia price field 711c that specifies a price that will be applied by the provider user for each anesthesia service performed in association with the services that have been categorized under the expanded procedure category. In exemplary embodiments, pricing tool 137 can be configured to derive and include an initial, default price value within anesthesia price field 711c. For example, pricing tool 137 can derive and set the default price value within anesthesia price field 711c as the average of the adjusted anesthesia rates for all services listed in the expanded display for a procedure category. In exemplary embodiments, pricing tool 137 can be configured to provide an option via user interface controls for the user to select a particular method from a list of methods that can be employed by pricing tool 137 to derive and set the price values within anesthesia price field 711c. For example, pricing tool 137 can be configured to enable the user select between using the average of the corresponding adjusted anesthesia rates for all services listed in the expanded display for a procedure category for the price values within anesthesia price field 711c or the highest of the corresponding adjusted anesthesia rates for all services listed in the expanded display for a procedure category for the price values within anesthesia price field 711c. In exemplary embodiments, pricing tool 137 can be further configured to allow the provider user accessing service pricing page 700 to access anesthesia price field 711c to input a particular price value within this field.

As further indicated in the example screen shot illustrated in FIG. 7B, the row entry for a particular procedure category will include a pricing value under anesthesia price column 716 that corresponds to the pricing value that is specified within anesthesia price field 711c in the expanded display for the procedure category. In this regard, pricing tool 137 can be configured to dynamically update the pricing value provided under anesthesia price column 716 in response to changes to the price value within anesthesia price field 711c. As discussed above, in exemplary configurations of pricing tool 137, such changes to the price value within anesthesia price field 711c in the expanded display for a particular procedure category may occur in response to changes to any of the current value that is specified in anesthesia location rate field 704f of locality adjustment section 704, the current percentage value that is specified in anesthesia rate adjustment field 706c of recommended rate adjustment section 706, changes in the particular method employed by pricing tool 137 to derive and set the price value within anesthesia price field 711c, and direct entries of a particular price value by a provider user within anesthesia price field 711c. As further illustrated in FIG. 7B, the row entry for a particular procedure category can include a pricing value under total amount column 715 that is provided as a sum of the price values listed under facility price column 712, physician price column 713, anesthesia price column 716, and, if included, additional fee column 714 in the row entry for a particular procedure category. This represents the actual price at which each service listed in the expanded display for a procedure category would be offered for purchase via marketplace system 100 as a bundled set of services from the provider user accessing service pricing page 700 via provider portal 130. In exemplary embodiments, pricing tool 137 can be further configured to provide an option via user interface controls implemented within service pricing page 700 for a provider user that is accessing the service pricing page 700 and has selected a medical specialty from drop-down menu 702 for which pricing tool 137 recognizes that the respective information records for services indicated as being commonly associated with the selected medical specialty within service pricing information database 114m include information records having an indication that the service is a primary service of a bundled set of services that a secondary service associated with the primary service in the bundled set is an anesthesia procedure to not include information and options pertaining to the associated anesthesia procedures and anesthesia pricing information within the service pricing page for the selected medical specialty. Pricing tool 137 can be configured to, in response to a provider user selecting this option within service pricing page 700 (for example, by de-selecting a checkbox), remove any information and options pertaining to the associated anesthesia procedures and anesthesia pricing information from the service pricing page for the selected medical specialty. For instance, upon a provider user selecting such an option within the example screen shot shown in FIG. 7B, pricing tool 137 can operate to reconfigure the user interface for service pricing page 700 to resemble the user interface illustrated in the example screen shot shown in FIG. 7A.

FIG. 7C is a screen shot illustrating a third example of a graphical user interface provided by service pricing page 700 for a user accessing provider portal 130 in association with a registered hospital system account. In the example illustrated in FIG. 7C, the user has selected "GI" (gastroenterology) from medical specialty drop-down menu 702, and pricing tool 137 has, in response to this selection, configured the user interface options and populated the information displayed within locality adjustment section 704, rate adjustment section 706, and detailed pricing information section 708 in accordance with the selection of "GI" from drop-down menu 702. In particular, pricing tool 137 has, in response to the user selection "GI" from medical specialty drop-down menu 702, recognized that the respective information records for services indicated as being commonly associated with the selected medical specialty of gastroenterology within service pricing information database 114m include information records having an indication that the service is a primary service of a bundled set of services that a secondary service associated with the primary service in the bundled set is a pathology service. In this regard, pricing tool 137 has configured the user interface options and populated the information displayed within detailed pricing information section 708 based on this recognition. In general, as shown in FIG. 7C, detailed pricing information section 708 is generated by pricing tool 137 as a table with various interactive user interface controls that includes, in addition to procedure column 711, facility price column 712, physician price column 713, additional fee column 714, and total amount column 715, a pathology price column 717.

As illustrated in FIG. 7C, the expanded information for a particular procedure category further includes, for each service categorized as a sub-procedure of the procedure category, in addition to a medical code number used to identify the service, a base facility rate, a base physician rate, an adjusted facility rate, and an adjusted physician rate as described above with reference to FIG. 7A, a base pathology rate. The base pathology rate for each service listed in the expanded display is obtained by pricing tool 137 from the pathology rate for the service that is stored within the respective information record maintained for the service within service pricing information database 114m for display within detailed pricing information section 708.

In the present example, as further illustrated in FIG. 7C, the expanded information for a particular procedure category further includes, in addition to physician price field 711a and facility price field 711b, a pathology price field 711d that specifies a price that will be applied by the provider user for each pathology service performed in association with the services that have been categorized under the expanded procedure category. In exemplary embodiments, pricing tool 137 can be configured to derive and include an initial, default price value within pathology price field 711d. For example, pricing tool 137 can derive and set the default price value within pathology price field 711d as the average of the base pathology rates for all services listed in the expanded display for a procedure category. In exemplary embodiments, pricing tool 137 can be further configured to allow the provider user accessing service pricing page 700 to access pathology price field 711d to input a particular price value within this field.

As further indicated in the example screen shot illustrated in FIG. 7C, the row entry for a particular procedure category will include a pricing value under pathology price column 717 that corresponds to the pricing value that is specified within pathology price field 711d in the expanded display for the procedure category. In this regard, pricing tool 137 can be configured to dynamically update the pricing value provided under pathology price column 717 in response to changes to the price value within pathology price field 711d. As further illustrated in FIG. 7B, the row entry for a particular procedure category can include a pricing value under total amount column 715 that is provided as a sum of the price values listed under facility price column 712, physician price column 713, pathology price column 717, and, if included, additional fee column 714 and anesthesia price column 716 in the row entry for a particular procedure category. This represents the actual price at which each service listed in the expanded display for a procedure category would be offered for purchase as a bundled set of services via marketplace system 100 from the provider user accessing service pricing page 700 via provider portal 130.

In exemplary embodiments, pricing tool 137 can be further configured to provide an option via user interface controls implemented within service pricing page 700 for a provider user that is accessing the service pricing page 700 and has selected a medical specialty from drop-down menu 702 for which pricing tool 137 recognizes that the respective information records for services indicated as being commonly associated with the selected medical specialty within service pricing information database 114m include information records having an indication that the service is a primary service of a bundled set of services that a secondary service associated with the primary service in the bundled set is a pathology service to not include information and options pertaining to the associated pathology services and pathology pricing information within the service pricing page for the selected medical specialty. Pricing tool 137 can be configured to, in response to a provider user selecting this option within service pricing page 700 (for example, by de-selecting a checkbox), remove any information and options pertaining to the associated pathology services and pathology pricing information from the service pricing page for the selected medical specialty. For instance, upon a provider user selecting such an option within the example screen shot shown in FIG. 7C, pricing tool 137 can operate to reconfigure the user interface for service pricing page 700 to resemble the user interface illustrated in the example screen shot shown in FIG. 7A or FIG. 7B.

In exemplary embodiments, the functionality that is provided within provider portal 130 for users of hospital system accounts can further include a set of user interface controls implemented by service selling service 135 that can be accessed by a user of a hospital system account to sell prepaid purchases of services to a customer in-person by operating a client system located at, for example, a medical clinic being visited by the customer to access application server 116. In this regard, service selling service 135 may provide functionality allowing a user of a hospital system account to sell, in addition to services that are offered for purchase by the hospital within server system 100, services that are constructed by a user of a hospital system account, including bundled sets of services, in accordance with treatments specifications for the customer and instructions received from the customer (such as a selection of a particular facility or a particular affiliated physician for performing a particular service) through operation of the client system. Service selling service 135 may provide such functionality in manner similar to the functionality provided by procedure management service 133 discussed above for allowing a user of a hospital system to establish a service offering to offer a healthcare service performed by affiliated physicians for purchase via server system 110. In this regard, service selling service 135 may also provide functionality for allowing the a user of a hospital system to perform such an in-person sale of a service to a customer in association with a customer account that is registered with server system 110 for the customer and, if the customer does not have a registered account, to perform registration session to register a customer account for the user with server system 110 based on information specified from the customer by providing functionality similar to the functionality provided by account management service 122 discussed above for customer registration sessions and perform the in-person sale of the service in association with the newly-registered customer account.

In addition, service selling service 135 may also provide functionality similar to the functionality provided by purchasing server 126 for processing payment for such an in-person sale of a service to a customer. For example, service selling service 135 can be implemented to, upon processing the customer payment for the purchase of such a constructed service, generate a voucher within the user interface for the in-person purchased service that can be utilized by the customer to redeem the purchase, which may be presented within the user interface at the client system in a form that allows the user of the hospital system to print a copy of the voucher to provide to the customer.

Referring again to FIG. 2, in exemplary embodiments, when a user operating a client system to access application server 116 via a corresponding client application executing on the client system initiates a registration with server system 110 and specifies an intention to register as a pharmacy administrator (for example, via a user interface element on any page implemented by navigation and search service 124), the user will be able to initiate a registration session with account management service 131 to register a pharmacy account with server system 110. Account management service 131 may be configured, for example, to implement a user interface that includes a series of pages with user interface controls accessible by the user to guide the user through the account registration process and prompt the user to input various types of information to be maintained by database server 112 within a respective account information record that is established for the user within pharmacy profile database 114e such as, for example, name, location(s) and hours, contact information (such as an email address and/or a telephone number), URLs or references to websites and social media profiles, compensation information (indicating a financial account for receiving payment for purchases of products offered by the pharmacy via the system), and any other suitable identifying information.

Account management service 131 can be configured to access database server 112 to create the respective account information record for the pharmacy within pharmacy profile database 114e based on the information input by the user during the registration process. Account management service 131 can be further configured to generate the unique pharmacy account identifier for the created account information record, which may be used, for example, to index and reference the created account information record within database server 112. The created account information record can also be identified with a unique user name and protected by a password, which can be used by the pharmacy administrator to log into the associated physician account when accessing application server 116.

In exemplary embodiments, the user interface implemented by account management service 131 may be further configured to provide user interface controls for requesting authorization for payment of a predetermined fee to gain access to the ability to offer healthcare products for purchase within marketplace system 100. Such a fee may be, for example, a onetime charge or a periodic charge (such as a monthly, biannual, or annual fee). Account management service 131 can be configured to, upon an authorization and appropriate payment information being provided by the user, access a corresponding third-party payment servicing system and utilize the payment information to direct the payment servicing system to transfer the amount for the payment authorized by the user from the account servicer of the user to a financial account maintained by the providers of marketplace system 100. Alternatively, the user interface implemented by account management service 131 may be configured to provide user interface controls for receiving an activation code to gain access to the ability to offer healthcare products for purchase within marketplace system 100. In this regard, the respective account information record established for the pharmacy administrator within pharmacy profile database 114e can further include an account status that is managed by account management service 131 for the user indicating whether the pharmacy is presently provided with the ability to offer healthcare products for purchase within marketplace system 100.

Upon a user registering a pharmacy account with server system 110 and logging into the pharmacy account (for example, by accessing a login user interface element or a login screen within the user interface implemented by navigation and search service 124 to provide the user name and password associated with the account), the user may be directed to a pharmacy account page implemented by provider portal 130 that provides a set of user interface controls that can be accessed by the user to access functionality provided by product management service 134 to offer healthcare products for purchase by customer users registered with the system and to access various account management functions provided by account management service 131.

Upon the user indicating an intention to offer a healthcare product for purchase (for example, by selecting a "Offer Service" tab within the pharmacy account page implemented by provider portal 130), the user will be able to initiate a product offering with product management service 134 to offer a healthcare product for purchase via server system 110. Product management service 134 may be configured, for example, to implement a user interface that includes a series of pages with user interface controls accessible by the user to guide the user through the product offering process and prompt the user to input various types of information to be maintained by database server 112 within a respective information record that is established in association with the unique pharmacy account identifier for the pharmacy within product offer database 114j. For example, the user may be provided with menu options providing access to an alphabetical list of selectable prescription drugs and an alphabetical list of selectable medical supplies and, upon selecting one of the lists, the user can select a particular product from the selected list.

Upon the user selecting a particular product, product management service 134 can assist the user with offering the product for purchase and establish the respective information record for the offered product within product offer database 114j by populating the information record with the unique product identifier for the information record within available products database 114i for the selected product, the unique account identifier for the account information record for the pharmacy within pharmacy profile database 114e as the provider that is offering the product through the system, a payment amount to be transferred to the pharmacy for a purchase of the product as specified by user input received from the pharmacy administrator, a discounted price for purchasing the product within marketplace system 100 (which may be calculated, for example, by adding a negotiated commission fee to the payment amount specified by the pharmacy administrator), a regular price for the product when the product is purchased outside of the system, additional descriptive information that may be provided via input received from the pharmacy administrator, a product offer identifier, and any other suitable information (such as an indication that the product is required to be purchased in association with a prescription from a medical specialist). As discussed above, when a payment for an offered product is processed by purchasing service 126, purchasing server 126 can be also be configured to generate a respective information record for the completed purchase with corresponding information within transaction information database 114k.

Upon the user indicating an intention within the pharmacy account page implemented by provider portal 130 to access various account management functions, the pharmacy administrator can access various user interface elements provided by account management service 131 to, for example, manage pharmacy and payment or compensation information, manage information pertaining to products offered for purchase by the pharmacy, and view a history of transactions performed for products offered for purchase by the pharmacy within server system 110.

In exemplary embodiments disclosed herein, because certain healthcare information may be considered highly confidential, marketplace system 100 can be implemented to provide for a high-level of security for information transferred between client applications executing on client systems 142 and application server 116. For illustration, whenever applicable, marketplace system 100 (for example, for operations and functionalities) may be implemented to comply with requirements under the Health Insurance Portability and Accountability Act (HIPAA). For example, if certain type of information should not be accessible to a specific party (for example, a prescription product manufacturer or service provider) according to HIPAA requirements or other confidentiality concerns, system 100 can implement information-control or information-protection measures that ensure the specific party cannot access that type of information. As another example, to protect patient privacy, information transmitted over a computer or communication network, such as information transmitted between application server 116 and any client system 140 and electronic messages transmitted by server system 110, can be encrypted. In exemplary embodiments, system 100 can be HIPAA-validated to ensure privacy and comply with all requirements.

Aspects of exemplary embodiments of the present invention described herein can be implemented using one or more program modules and data storage units. As used herein, the term "modules", "program modules", "components", "systems", "tools", "utilities", and the like include routines, programs, objects, components, data structures, and instructions, or instructions sets, and so forth that perform particular tasks or implement particular abstract data types. As can be appreciated, the modules refer to computer-related entities that can be implemented as software, hardware, firmware and/or other suitable components that provide the described functionality, and which may be loaded into memory of a machine embodying an exemplary embodiment of the present invention. Aspects of the modules may be written in a variety of programming languages, such as C, C++, Java, etc. The functionality provided by modules used for aspects of exemplary embodiments described herein can be combined and/or further partitioned.

As used herein, the terms "data storage unit," "data store", "storage unit", and the like can refer to any suitable memory device that may be used for storing data, including manual files, machine readable files, and databases. The modules and/or storage units can all be implemented and run on the same computing system (for example, the exemplary computer system illustrated in FIG. 5 and described below) or they can be implemented and run on different computing systems. For example, one or modules can be implemented on a personal computer operated by a user while other modules can be implemented on a remote server and accessed via a network.

In exemplary embodiments, the client applications utilized in exemplary embodiments of the present invention can be configured for incorporation within any suitable network computing environment as a plug-in, add-on, or extension. As used herein, the term "plug-in" can refer to a software application or module program, or one or more computer instructions, which may or may not be in communication with other software applications or modules, that interacts with a host application to provide specified functionality, and which may include any file, image, graphic, icon, audio, video, or any other attachment. In other exemplary embodiments, the client applications can be implemented as a standalone program that is run as a separate computer process, a portable application, a native component of an automated software testing tool, a part of a software bundle, or any other suitable implementation.

In the preceding description, for purposes of explanation, numerous specific details are set forth in order to provide a thorough understanding of the described exemplary embodiments. Nevertheless, one skilled in the art will appreciate that many other embodiments may be practiced without these specific details and structural, logical, and electrical changes may be made.

Some portions of the exemplary embodiments described above are presented in terms of algorithms and symbolic representations of operations on data bits within a processor-based system. The operations are those requiring physical manipulations of physical quantities. These quantities may take the form of electrical, magnetic, optical, or other physical signals capable of being stored, transferred, combined, compared, and otherwise manipulated, and are referred to, principally for reasons of common usage, as bits, values, elements, symbols, characters, terms, numbers, or the like. Nevertheless, it should be noted that all of these and similar terms are to be associated with the appropriate physical quantities and are merely convenient labels applied to these quantities. Unless specifically stated otherwise as apparent from the description, terms such as "executing" or "processing" or "computing" or "calculating" or "determining" or the like, may refer to the action and processes of a processor-based system, or similar electronic computing device, that manipulates and transforms data represented as physical quantities within the processor-based system's storage into other data similarly represented or other such information storage, transmission or display devices.

Exemplary embodiments of the present invention can be realized in hardware, software, or a combination of hardware and software. Exemplary embodiments can be realized in a centralized fashion in one computer system or in a distributed fashion where different elements are spread across several interconnected computer systems. Any kind of computer system—or other apparatus adapted for carrying out the methods described herein—is suited. A typical combination of hardware and software could be a general-purpose computer system with a computer program that, when being loaded and executed, controls the computer system such that it carries out the methods described herein.

Exemplary embodiments of the present invention can also be embedded in a computer program product, which comprises all the features enabling the implementation of the methods described herein, and which—when loaded in a computer system—is able to carry out these methods. Computer program means or computer program as used in the present invention indicates any expression, in any language, code or notation, of a set of instructions intended to cause a system having an information processing capability to perform a particular function either directly or after either or both of the following: (a) conversion to another language, code or, notation; and (b) reproduction in a different material form.

A computer system in which exemplary embodiments can be implemented may include, inter alia, one or more computers and at least a computer program product on a computer readable medium, allowing a computer system, to read data, instructions, messages or message packets, and other computer readable information from the computer readable medium. The computer readable medium may include non-volatile memory, such as ROM, Flash memory, Disk drive memory, CD-ROM, and other permanent storage. Additionally, a computer readable medium may include, for example, volatile storage such as RAM, buffers, cache memory, and network circuits. Furthermore, the computer readable medium may comprise computer readable information in a transitory state medium such as a network link and/or a network interface, including a wired network or a wireless network, that allow a computer system to read such computer readable information.

Figure 5:
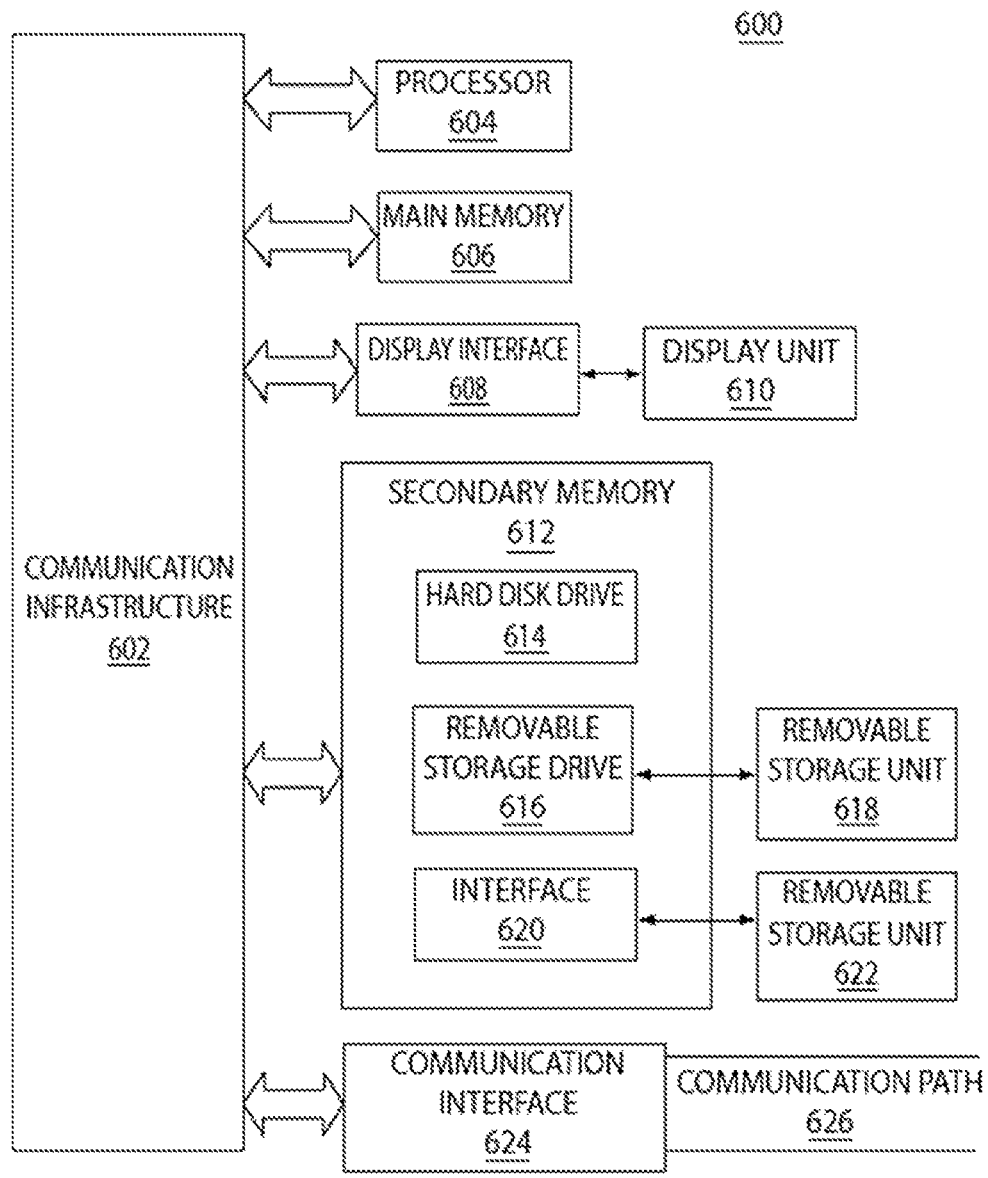
FIG. 5 is a block diagram of an exemplary computer system 600 that can be used for implementing exemplary embodiments of the present invention.

FIG. 5 is a block diagram of an exemplary computer system 600 that can be used for implementing exemplary embodiments of the present invention. Computer system 600 includes one or more processors, such as processor 604. Processor 604 is connected to a communication infrastructure 602 (for example, a communications bus, cross-over bar, or network). Various software embodiments are described in terms of this exemplary computer system. After reading this description, it will become apparent to a person of ordinary skill in the relevant art(s) how to implement the invention using other computer systems and/or computer architectures.

Exemplary computer system 600 can include a display interface 608 that forwards graphics, text, and other data from the communication infrastructure 602 (or from a frame buffer not shown) for display on a display unit 610. Computer system 600 also includes a main memory 606, which can be random access memory (RAM), and may also include a secondary memory 612. Secondary memory 612 may include, for example, a hard disk drive 614 and/or a removable storage drive 616, representing a floppy disk drive, a magnetic tape drive, an optical disk drive, etc. Removable storage drive 616 reads from and/or writes to a removable storage unit 618 in a manner well known to those having ordinary skill in the art. Removable storage unit 618, represents, for example, a floppy disk, magnetic tape, optical disk, etc. which is read by and written to by removable storage drive 616. As will be appreciated, removable storage unit 618 includes a computer usable storage medium having stored therein computer software and/or data.

In exemplary embodiments, secondary memory 612 may include other similar means for allowing computer programs or other instructions to be loaded into the computer system. Such means may include, for example, a removable storage unit 622 and an interface 620. Examples of such may include a program cartridge and cartridge interface (such as that found in video game devices), a removable memory chip (such as an EPROM, or PROM) and associated socket, and other removable storage units 622 and interfaces 620 which allow software and data to be transferred from the removable storage unit 622 to computer system 600.

Computer system 600 may also include a communications interface 624. Communications interface 624 allows software and data to be transferred between the computer system and external devices. Examples of communications interface 624 may include a modem, a network interface (such as an Ethernet card), a communications port, a PCM-CIA slot and card, etc. Software and data transferred via communications interface 624 are in the form of signals which may be, for example, electronic, electromagnetic, optical, or other signals capable of being received by communications interface 624. These signals are provided to communications interface 624 via a communications path (that is, channel) 626. Channel 626 carries signals and may be implemented using wire or cable, fiber optics, a phone line, a cellular phone link, an RF link, and/or other communications channels.

In this document, the terms "computer program medium," "computer usable medium," and "computer readable medium" are used to generally refer to media such as main memory 606 and secondary memory 612, removable storage drive 616, a hard disk installed in hard disk drive 614, and signals. These computer program products are means for providing software to the computer system. The computer readable medium allows the computer system to read data, instructions, messages or message packets, and other computer readable information from the computer readable medium. The computer readable medium, for example, may include non-volatile memory, such as Floppy, ROM, Flash memory, Disk drive memory, CD-ROM, and other permanent storage. It can be used, for example, to transport information, such as data and computer instructions, between computer systems. Furthermore, the computer readable medium may comprise computer readable information in a transitory state medium such as a network link and/or a network interface including a wired network or a wireless network that allow a computer to read such computer readable information.

Computer programs (also called computer control logic) are stored in main memory 606 and/or secondary memory 612. Computer programs may also be received via communications interface 624. Such computer programs, when executed, can enable the computer system to perform the features of exemplary embodiments of the present invention as discussed herein. In particular, the computer programs, when executed, enable processor 604 to perform the features of computer system 600. Accordingly, such computer programs represent controllers of the computer system.

While the invention has been described in detail with reference to exemplary embodiments, it will be understood by those skilled in the art that various changes and alternations may be made and equivalents may be substituted for elements thereof without departing from the scope of the invention as defined by the appended claims. In addition, many modifications may be made to adapt a particular application or material to the teachings of the invention without departing from the essential scope thereof.

Variations described for exemplary embodiments of the present invention can be realized in any combination desirable for each particular application. Thus particular limitations, and/or embodiment enhancements described herein, which may have particular limitations need be implemented in methods, systems, and/or apparatuses including one or more concepts describe with relation to exemplary embodiments of the present invention.

Therefore, it is intended that the invention not be limited to the particular embodiments disclosed as the best mode contemplated for carrying out this invention, but that the invention will include all embodiments falling within the scope of the present application as set forth in the following claims, wherein reference to an element in the singular, such as by use of the article "a" or "an" is not intended to mean "one and only one" unless specifically so stated, but rather "one or more." Moreover, no claim element is to be construed under the provisions of 35 U.S.C. § 112, sixth paragraph, unless the element is expressly recited using the phrase "means for" or "step for." These following claims should be construed to maintain the proper protection for the present invention.

What is claimed is:

1. An apparatus comprising:

an application server for pricing offers of healthcare services by healthcare service providers, that provides a network service, the network service including a pricing tool comprising an interactive pricing page with a set of accessible user interface controls to email prices, save changes and purchase healthcare services in which said pricing tool is accessible via a user interface on each of the client systems, the user interface rendering a common display structure to represent the network service provided by the application server for a user of a client;

a data storage system storing comprising a plurality of service detail information records associated with a plurality of healthcare service sets, each healthcare service set identifying a primary service, a set of base pricing metrics for the primary service, and a first set of cost adjustment metrics for each of a plurality of geographic zones and wherein, upon a user accessing the pricing tool, can determine a base physician fee for the primary service based on the set of base pricing metrics for the primary service included in the service detail information record, determine a location indication, based on the location stored in a session data object, that specifies a location for performing the primary service, dynamically perform a calculation of an adjusted physician fee for the primary service based on the first set of cost adjustment metrics that corresponds to the location specified by the location indication, determine a recommended price for the indicated healthcare service set based on the adjusted physician fee calculated for the primary service, and render respective indications of the adjusted physician fee and the recommended price determined for the indicated healthcare service set, wherein the user interface provided by the client application includes a graphical user interface element that is accessible by the user to submit a request to the pricing tool for the indicated healthcare service set to be offered for purchase, and the pricing tool is configured to generate an information record, store the information record in association with the respective account information record, update the session data object on the application server, and send an electronic document to the user in a printable form;

wherein, upon rendering the respective indications of the adjusted physician fee calculated for the primary service and the recommended price determined for the indicated healthcare service set, the pricing tool is operable to, in response to receiving a request submitted from the user, direct a service offer information record associated with a service offer for the indicated healthcare service set to be established that comprises a plurality of other service offer information records, wherein service offer information record that is established having an indication of the primary service, a purchase price based on the recommended price, and payment amount based on the adjusted physician fee calculated for the primary service, and wherein a service purchasing tool is accessible via the network to, based on the plurality of service offer information records and the session data object, facilitate purchases of service offers selected from the plurality of service offers; and wherein the network service operates to generate and transmit a voucher for the user that includes a description of the purchased service offer.

* * * * *